(12) United States Patent
Song et al.

(10) Patent No.: US 11,518,810 B2
(45) Date of Patent: Dec. 6, 2022

(54) BISPECIFIC RECOMBINANT PROTEIN AND USE THEREOF

(71) Applicant: SHANGHAI JMT-BIO TECHNOLOGY CO., LTD., Shanghai (CN)

(72) Inventors: Liping Song, Shanghai (CN); Xiaotian Cui, Shanghai (CN); Jian Wang, Shanghai (CN); Haixiang Wu, Shanghai (CN); Jiana Jia, Shanghai (CN); Yi Fan, Shanghai (CN); Ganliang Zhang, Shanghai (CN); Tao Li, Shanghai (CN); Hong Xu, Shanghai (CN); Yisha She, Shanghai (CN); Kai Long, Shanghai (CN)

(73) Assignee: SHANGHAI JMT-BIO TECHNOLOGY CO., LTD., Shanghai (CN)

( * ) Notice: Subject to any disclaimer, the term of this patent is extended or adjusted under 35 U.S.C. 154(b) by 308 days.

(21) Appl. No.: 16/610,902

(22) PCT Filed: May 8, 2018

(86) PCT No.: PCT/CN2018/086050
§ 371 (c)(1),
(2) Date: Nov. 4, 2019

(87) PCT Pub. No.: WO2018/205936
PCT Pub. Date: Nov. 15, 2018

(65) Prior Publication Data
US 2020/0157223 A1    May 21, 2020

(30) Foreign Application Priority Data

May 8, 2017  (CN) .......................... 201710317926.7
Dec. 5, 2017  (CN) .......................... 201711269620.5

(51) Int. Cl.
| | | |
|---|---|---|
| C07K 16/28 | (2006.01) | |
| A61P 35/00 | (2006.01) | |
| C07K 16/46 | (2006.01) | |
| C12N 15/85 | (2006.01) | |
| A61K 38/00 | (2006.01) | |
| A01K 67/027 | (2006.01) | |
| C07K 14/435 | (2006.01) | |

(52) U.S. Cl.
CPC ...... *C07K 16/2827* (2013.01); *A01K 67/0278* (2013.01); *A61P 35/00* (2018.01); *C07K 14/435* (2013.01); *C07K 16/2863* (2013.01); *C07K 16/2887* (2013.01); *C07K 16/46* (2013.01); *C12N 15/85* (2013.01); *A01K 2207/15* (2013.01); *A01K 2227/105* (2013.01); *A01K 2267/0331* (2013.01); *A61K 38/00* (2013.01)

(58) Field of Classification Search
CPC ................ C07K 16/30; C07K 16/2863; C07K 16/2896; C07K 2317/31; A61P 35/00
See application file for complete search history.

(56) References Cited

U.S. PATENT DOCUMENTS

2018/0141986 A1    5/2018  Tian et al.

FOREIGN PATENT DOCUMENTS

| CN | 104356236 A | 2/2015 |
|---|---|---|
| CN | 105121467 A | 12/2015 |
| CN | 103772504 B | 9/2016 |
| CN | 106146670 A | 11/2016 |
| CN | 106519036 A | 3/2017 |
| CN | 107459579 A | 12/2017 |
| CN | 108864290 B | 12/2021 |
| WO | 2007005874 A2 | 1/2007 |
| WO | 2014087248 A2 | 6/2014 |
| WO | 2016024021 A1 | 2/2016 |
| WO | 2016126781 A1 | 8/2016 |
| WO | 2016169261 A1 | 10/2016 |
| WO | 2017027422 A1 | 2/2017 |
| WO | 2018075857 A1 | 4/2018 |

OTHER PUBLICATIONS

Cao Rui et al., "Advances in antibody drugs for cancer targeted therapy", Chinese Journal of Biochemical Pharmaceutics, 2016, vol. 36, No. 6, p. 15-18 (with English abstract).
Barnhart BC et al., "The role of Fc-FcγR interactions in the antitumor activity of therapeutic antibodies", Immunology and Cell Biology, 2017, vol. 95, p. 340-346.
Willingham SB et al., "CD47-signal regulatory protein alpha (SIRPα) interaction is a therapeutic target for human solid tumors", Proceedings of the National Academy of Sciences of the United States of America, 2012, vol. 109, No. 17, p. 6662-6667.
Oldenborg PA et al., "Role of CD47 as a marker of self on red blood cells", Science, 2000, vol. 288, No. 5473, p. 2051-2054.

(Continued)

*Primary Examiner* — Ruixiang Li
(74) *Attorney, Agent, or Firm* — Seed IP Law Group LLP

(57) ABSTRACT

Provided is a bispecific recombinant protein, comprising a high affinity tumor-targeting arm and a low affinity fusion protein blocking the interaction of CD47 with SIRPα. The antibody corresponding to the high affinity tumor-targeting arm does not bind to CD47, and its binding affinity to the target antigen on the tumor cell is at least 6 times as great as the binding affinity of monomer fusion protein homodimer corresponding to the low affinity fusion protein blocking the interaction of CD47 with SIRPα, to a CD47 on the tumor cell, wherein the low affinity fusion protein blocking the interaction of CD47 with SIRPα comprises a SIRPα extracellular truncation. Also provided are nucleic acid molecules encoding recombinant proteins and the use of the recombinant proteins and nucleic acid molecules in the manufacture of a medicament for treating tumors.

12 Claims, 18 Drawing Sheets
Specification includes a Sequence Listing.

(56) References Cited

OTHER PUBLICATIONS

Vonderheide RH, "CD47 blockade as another immune checkpoint therapy for cancer", Nature Medicine, 2015, vol. 21, No. 10, p. 1122-1123.
Mccracken MN et al., "Molecular Pathways: Activating T Cells after Cancer Cell Phagocytosis from Blockade of CD47 "Don't Eat Me" Signals", Clinical Cancer Research, 2015, vol. 21, No. 16, p. 3597-3601.
Weiskopf K et al., "Engineered SIRPα variants as immunotherapeutic adjuvants to anti-cancer antibodies", Science, 2013, vol. 341, No. 6141, p. 88-91.
Chao MP et al., "Anti-CD47 antibody synergizes with rituximab to promote phagocytosis and eradicate non-Hodgkin lymphoma", Cell, 2010, vol. 142, No. 5, p. 699-713.
Zhao XW et al., "CD47-signal regulatory protein-α (SIRPα) interactions form a barrier for antibody-mediated tumor cell destruction", Proceedings of the National Academy of Sciences of the United States of America, 2011, vol. 108, No. 45, p. 18342-18347.
Lee WY et al., "The Role of cis Dimerization of Signal Regulatory Protein α (SIRPα) in Binding to CD47", J Biol Chem, 2010, vol. 285, No. 49, p. 37953-37963.
Lee WY et al., "Novel Structural Determinants on SIRP α that Mediate Binding to CD47", Journal of Immunology, 2007, vol. 179, No. 11, p. 7741-7750.
Petrova PS et al., "TTI-621 (SIRPαFc): A CD47-Blocking innate immune Checkpoint Inhibitor with Broad Antitumor-Activity and Minimal Erythrocyte Binding", Clin Cancer Res, 2017, vol. 23, No. 4, p. 1068-1079.
International Search Report and Written Opinion of PCT/CN2018/086050 dated Aug. 1, 2018.
Dec. 30, 2020 Chinese Office Action issued in Chinese Patent Application No. 201810430371.
Apr. 23, 2021 Chinese Office Action issued in Chinese Patent Application No. 201810430371.
Mar. 15, 2021 partial supplementary European search report in European Application No. 18798470.3.
"Targeting the 5T4 oncofetal glycoprotein with an antibody drug conjugate (A1mcmmaf) improves survival in patient-derived xenograft models of acute lymphoblastic leukemia", Owen J.McGinn et al., Mar. 24, 2017.
"Evolving Strategies for Target Selection for Antibody-Drug Conjugates". Pharmaceutical Research, Springer New Yorl LLC, US, Jan. 15, 2015.
"Structural Insights into the Inhibition of Wnt Signaling by Cancer Antigen 5T4/Wnt-Activated Inhibitory Factor 1", Zhao Yuguang et al, Apr. 8, 2014.
Jun. 1, 2021 Chinese Office Action issued in Chinese Patent Application No. 201810430371.
"Novel structural determinants on SIRP a that mediate binding to CD47" P7741-7750.
"2JJS_A, Hatherley et al NCBI Origin".
"2WNG_A, Hatherley et al NCBI Origin".
"AHH26692.1 Strausberg et al NCBI Origin".
Jul. 6, 2021 Extended supplementary European search report in European Application No. 18798470.3.
Jul. 22, 2021 First Office Action in Russian Application No. 2019138624.
CD20-targeting in B-cell malignancies: novel prospects for antibodies and combination therapies.
Nov. 30, 2021 the Second Office Action issued in Russian application No. 2019138624.
Colman P M., Effects of amino acid sequence changes on antibody-antigen interactions, Research in Immunology, 1994, V. 145, N. 1, pp. 33-36, p. 33.
Safdari Y. et al., Antibody humanization methods—a review and update, Biotechnology and Genetic Engineering Reviews, 2013, V. 29, N. 2, pp. 175-186, pp. 178, 180.
Torres M. et al.,The immunoglobulin constant region contributes to affinity and specificity, Trends in immunology, 2008, V. 29, N. 2, pp. 91-97, pp. 93-94.
Hatherley D. et al., Paired receptor specificity explained by structures of signal regulatory proteins alone and complexed with CD47, Molecular cell, 2008, V. 31, N. 2, pp. 266-277, Table 2.
Itzankov A. et al., Prognostic significance of CD20 expression in classical Hodgkin lymphoma: a clinicopathological study of 119 cases, Clinical cancer research, 2003, V. 9, N. 4, pp. 1381-1386, p. 1383.
Taiwan Office Action dated May 16, 2022, issued in Taiwan application No. 107115571, 9 pages.
Japanese Office Action dated May 17, 2022, issued in Japanese Patent Application No. 2020-513390, 11 pages.

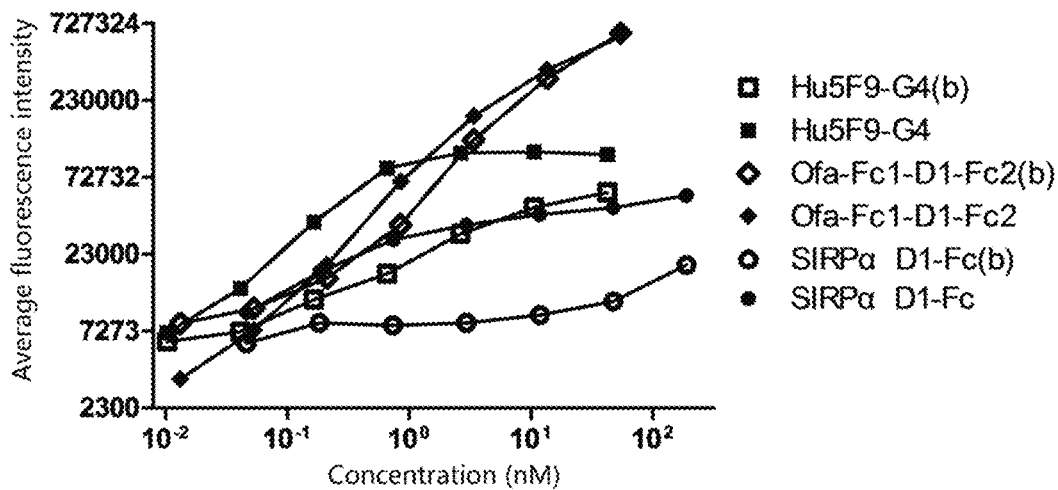
Fig. 7
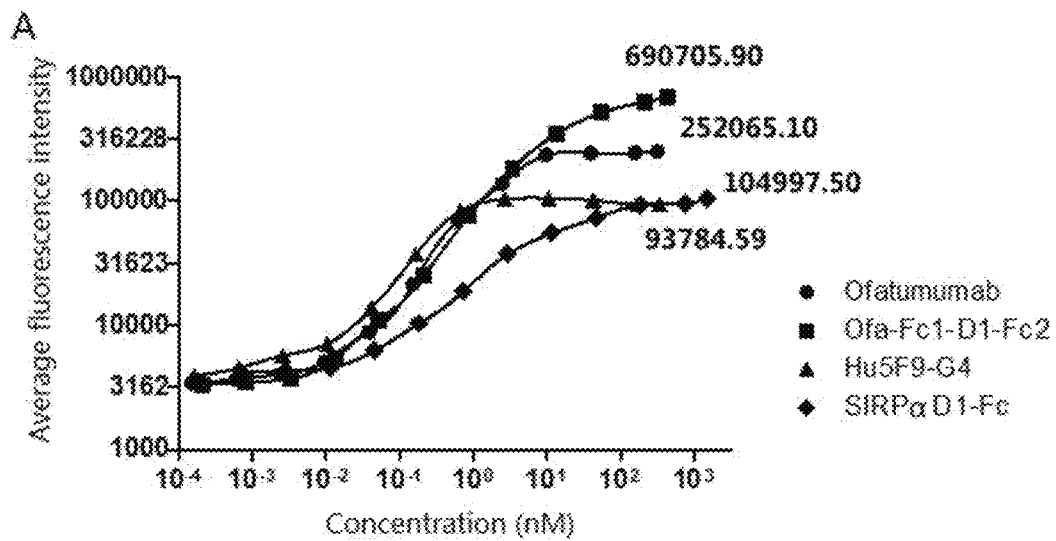

Cont'd

| No. | SEQ ID NOs: | Sequence name | Protein sequence |
|---|---|---|---|
| 1 | 1 | Ofatumumab heavy chain | MEWSWVFLFFLSVTTGVHSEVQLVESGGGLVQPGRSLRLSCAASGFTFNDYAMHWVRQAPGKGLEWVSTISWNSGSIGYA DSVKGRFTISRDNAKKSLYLQMNSLRAEDTALYYCAKDIQYGNYYYGMDVWGQGTTVTVSSASTKGPSVFPLAPSSKSTS GGTAALGCLVKDYFPEPVTVSWNSGALTSGVHTFPAVLQSSGLYSLSSVVTVPSSSLGTQTYICNVNHKPSNTKVDKKVE PKSCDKTHTCPPCPAPELLGGPSVFLFPPKPKDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREPQVYTLPPSRDELTKNQVSLTCLVKGFYPSD IAVEWESNGQPENNYKTTPPVLDSDGSFFLYSKLTVDKSRWQQGNVFSCSVMHEALHNHYTQKSLSLSPGK |
| 2 | 2 | Ofatumumab light chain | MSVPTQVLGLLLLWLTDARCEIVLTQSPATLSLSPGERATLSCRASQSVSSYLAWYQQKPGQAPRLLIYDASNRATGIPA RFSGSGSGTDFTLTISSLEPEDFAVYYCQQRSNWPITFGQGTRLEIKRTVAAPSVFIFPPSDEQLKSGTASVVCLLNNFY PREAKVQWKVDNALQSGNSQESVTEQDSKDSTYSLSSTLTLSKADYEKHKVYACEVTHQGLSSPVTKSFNRGEC |
| 3 | 3 | Obinutuzumab heavy chain | MEWSWVFLFFLSVTTGVHSQVQLVQSGAEVKKPGSSVKVSCKASGYAFSYSWINWVRQAPGQGLEWMGRIFPGDGDTDYN GKFKGRVTITADKSTSTAYMELSSLRSEDTAVYYCARNVFDGYWLVYWGQGTLVTVSSASTKGPSVFPLAPSSKSTSGGT AALGCLVKDYFPEPVTVSWNSGALTSGVHTFPAVLQSSGLYSLSSVVTVPSSSLGTQTYICNVNHKPSNTKVDKKVEPKS CDKTHTCPPCPAPELLGGPSVFLFPPKPKDTLMISRTPEVTCVVVDVSHEDPEVKFNWYVDGVEVHNAKTKPREEQYNST YRVVSVLTVLHQDWLNGKEYKCKVSNKALPAPIEKTISKAKGQPREPQVYTLPPSRDELTKNQVSLTCLVKGFYPSDIAV EWESNGQPENNYKTTPPVLDSDGSFFLYSKLTVDKSRWQQGNVFSCSVMHEALHNHYTQKSLSLSPGK |
| 4 | 4 | Obinutuzumab light chain | MSVPTQVLGLLLLWLTDARCDIVMTQTPLSLPVTPGEPASISCRSSKSLLHSNGITYLWYLQKPGQSPQLLIYQMSNLV SGVPDRFSGSGSGTDFTLKISRVEAEDVGVYYCAQNLELPYTFGGGTKVEIKRTVAAPSVFIFPPSDEQLKSGTASVVCL LNNFYPREAKVQWKVDNALQSGNSQESVTEQDSKDSTYSLSSTLTLSKADYEKHKVYACEVTHQGLSSPVTKSFNRGEC |
| 5 | 5 | Hu5F9-G4 heavy chain | MRAWIFFLLCLAGRALAQVQLVQSGAEVKKPGASVKVSCKASGYTFTNYNMHWVRQAPGQRLEWMGTIYPGNDDTSYNQK FKDRVTITADTSASTAYMELSSLRSEDTAVYYCARGGYRAMDYWGQGTLVTVSSASTKGPSVFPLAPCSRSTSESTAALG CLVKDYFPEPVTVSWNSGALTSGVHTFPAVLQSSGLYSLSSVVTVPSSSLGTKTYTCNVDHKPSNTKVDKRVESKYGPPC PPCPAPEFLGGPSVFLFPPKPKDTLMISRTPEVTCVVVDVSQEDPEVQFNWYVDGVEVHNAKTKPREEQFNSTYRVVSVL TVLHQDWLNGKEYKCKVSNKGLPSSIEKTISKAKGQPREPQVYTLPPSQEEMTKNQVSLTCLVKGFYPSDIAVEWESNGQ PENNYKTTPPVLDSDGSFFLYSRLTVDKSRWQEGNVFSCSVMHEALHNHYTQKSLSLSLGK |
| 6 | 6 | Hu5F9-G4 light chain | MRAWIFFLLCLAGRALADIVMTQSPLSLPVTPGEPASISCRSSQSIVYSNGNTYLGWYLQKPGQSPQLLIYKVSNRFSGV PDRFSGSGSGTDFTLKISRVEAEDVGVYYCFQGSHVPYTFGQGTKLEIKRTVAAPSVFIFPPSDEQLKSGTASVVCLLNN FYPREAKVQWKVDNALQSGNSQESVTEQDSKDSTYSLSSTLTLSKADYEKHKVYACEVTHQGLSSPVTKSFNRGEC |
| 7 | 7 | JMT101 heavy chain | MRAWIFFLLCLAGRALAQVQLQESGPGLVKPSETLSLTCTVSGFSLSNYDVHWVRQAPGKGLEWLGVIWSGGNTDYNTPF TSRLTISVDTSKNQFSLKLSSVTAADTAVYYCARALDYDYEFAYWGQGTLVTVSSASTKGPSVFPLAPSSKSTSGGTAA LGCLVKDYFPEPVTVSWNSGALTSGVHTFPAVLQSSGLYSLSSVVTVPSSSLGTQTYICNVNHKPSNTKVDKRVEPKSCD KTHTCPPCPAPELLGGPSVFLFPPKPKDTLMISRTPEVTCVVVDVSHEDPEVKFNWYVDGVEVHNAKTKPREEQYNSTYR VVSVLTVLHQDWLNGKEYKCKVSNKALPAPIEKTISKAKGQPREPQVYTLPPSREEMTKNQVSLTCLVKGFYPSDIAVEW ESNGQPENNYKTTPPVLDSDGSFFLYSKLTVDKSRWQQGNVFSCSVMHEALHNHYTQKSLSLSPGK |
| 8 | 8 | JMT101 light chain | MRAWIFFLLCLAGRALAEIVLTQSPDFQSVTPKEKVTITCRASQSIGTNIHWYQQKPDQSPKLLIKYASESISGIPSRFS GSGSGTDFTLTINSLEAEDAATYYCQQNNEWPTSFGQGTKLEIKRTVAAPSVFIFPPSDEQLKSGTASVVCLLNNFYPRE AKVQWKVDNALQSGNSQESVTEQDSKDSTYSLSSTLTLSKADYEKHKVYACEVTHQGLSSPVTKSFNRGEC |
| 9 | 9 | Trastuzumab heavy chain | MRAWIFFLLCLAGRALAEVQLVESGGGLVQPGGSLRLSCAASGFNIKDTYIHWVRQAPGKGLEWVARIYPTNGYTRYADSV KGRFTISADTSKNTAYLQMNSLRAEDTAVYYCSRWGGDGFYAMDYWGQGTLVTVSSASTKGPSVFPLAPSSKSTSGGTAAL GCLVKDYFPEPVTVSWNSGALTSGVHTFPAVLQSSGLYSLSSVVTVPSSSLGTQTYICNVNHKPSNTKVDKKVEPPKSCDK THTCPPCPAPELLGGPSVFLFPPKPKDTLMISRTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPSREEMTKNQVSLTCLVKGFYPSDIAVEWESN GQPENNYKTTPPVLDSDGSFFLYSKLTVDKSRWQQGNVFSCSVMHEALHNHYTQKSLSLSPGK |
| 10 | 10 | Trastuzumab light chain | MRAWIFFLLCLAGRALADIQMTQSPSSLSASVGDRVTITCRASQDVNTAVAWYQQKPGKAPKLLIYSASFLYSGVPS RFSGSRSGTDFTLTISSLQPEDFATYYCQQHYTTPPTFGQGTKVEIKRTVAAPSVFIFPP SDEQLKSGTASVVCLLNNFYPREAKVQWKVDNALQSGNSQESVTEQDSKDSTYSLSSTLT LSKADYEKHKVYACEVTHQGLSSPVTKSFNRGEC |
| 11 | 11 | SIRPα D1-Fc | MEWSWVFLFFLSVTTGVHSEEELQVIQPDKSVSVAAGESAILHCTVTSLIPVGPIQWFRGAGPARELIYNQKEGHFPRVT TVSESTKRENMDFSISISAITPADAGTYYCVKFRKGSPDTEFKSGAGTELSVDKTHTCPPCPAPELLGGPSVFLFPPKPK DTLMISRTPEVTCVVVDVSHEDPEVKFNWYVDGVEVHNAKTKPREEQYNSTYRVVSVLTVLHQDWLNGKEYKCKVSNKAL PAPIEKTISKAKGQPREPQVYTLPPSRDELTKNQVSLTCLVKGFYPSDIAVEWESNGQPENNYKTTPPVLDSDGSFFLYS KLTVDKSRWQQGNVFSCSVMHEALHNHYTQKSLSLSPGK |
| 12 | 12 | Atezolizumab heavy chain | MEFWLSWVFLVAILKGVQCEVQLVESGGGLVQPGGSLRLSCAASGFTFSDSWIHWVRQAPGKGLEWVAWISPYGGSTYYA DSVKGRFTISADTSKNTAYLQMNSLRAEDTAVYYCARRHWPGGFDYWGQGTLVTVSSASTKGPSVFPLAPSSKSTSGGTA ALGCLVKDYFPEPVTVSWNSGALTSGVHTFPAVLQSSGLYSLSSVVTVPSSSLGTQTYICNVNHKPSNTKVDKKVEPKSC DKTHTCPPCPAPELLGGPSVFLFPPKPKDTLMISRTPEVTCVVVDVSHEDPEVKFNWYVDGVEVHNAKTKPREEQYASTY RVVSVLTVLHQDWLNGKEYKCKVSNKALPAPIEKTISKAKGQPREPQVYTLPPSREEMTKNQVSLTCLVKGFYPSDIAVE WESNGQPENNYKTTPPVLDSDGSFFLYSKLTVDKSRWQQGNVFSCSVMHEALHNHYTQKSLSLSPGK |
| 13 | 13 | Atezolizumab light chain | MEFWLSWVFLVAILKGVQCDIQMTQSPSSLSASVGDRVTITCRASQDVSTAVAWYQQKPGKAPKLLIYSASFLYSGVPSR FSGSGSGTDFTLTISSLQPEDFATYYCQQYLYHPATFGQGTKVEIKRTVAAPSVFIFPPSDEQLKSGTASVVCLLNNFYP REAKVQWKVDNALQSGNSQESVTEQDSKDSTYSLSSTLTLSKADYEKHKVYACEVTHQGLSSPVTKSFNRGEC |

| No. | SEQ ID NOs: | Sequence name | Protein sequence | SEQ ID NOs: | DNA Sequence |
|---|---|---|---|---|---|
| 20 | 20 | Anti-Her2(T)-Fc1 heavy chain | MEWSWVFLFFLSVTTGVHSEVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK | 38 | ATGGAATGGAGCTGGGTGTTCCTGTTCTTTCTGTTCCTGTCACAGGCGTGCATTCTGAGGTGCAGTTGGTGGAGAGCGGGGGGGGCTGGTGCAGCCTGGAGGAAGTTTGAGGTTGAGCTGTGCCGCAAGCGGGTTCAACATTAAGGACACATACATTCACTGGGTGAGGCAGGCACCCGGAAAGGGACTGGAGTGGGTGGCTAGGATCTACCCCACCAACGGCTACACAAGGTACGCCGACAGTGTGAAGGGCCGGTTCACCATTTCCGCCGACACCTCCAAGAACACCGCCTACCTGCAGATGAACAGCCTGAGGGCCGAGGACACCGCCGTCTACTACTGCTCCAGGTGGGGAGGAGACGGATTCTATGCTATGGACTACTGGGGACAGGGCACCCTGGTGACCGTGTCATCTGCTTCTACCAAGGGCCCCTCCGTGTTTCCTCTGGCCCCTTCCAGCAAGTCCACCTCTGGCGGAACAGCCGCTCTGGGCTGCCTCGTGAAGGACTACTTCCCCGAGCCTGTGACCGTGTCCTGGAACTCTGGCGCTCTGACATCCGGCGTGCACACCTTCCCTGCTGTGCTGCAGTCTAGCGGCCTGTACTCCCTGTCCTCCGTCGTGACCGTGCCTTCCAGCTCTCTGGGCACCCAGACCTACATCTGCAACGTGAACCACAAGCCCTCCAACACCAAGGTGGACAAGAAGGTGGAACCCAAGTCCTGCGACAAGACCCACACCTGTCCCCCTTGTCCTGCCCCTGAACTGCTGGGCGGACCTTCCGTGTTCCTGTTCCCCCCAAAAGCCCAAGGACACCCTGATGATCTCCCGGACCCCCGAAGTGACCTGCGTGGTGGATGTGTCCCACGAGGACCCTGAAGTGAAGTTCAATTGGTACGTGGACGGCGTGGAAGTGCACAACGCCAAGACCAAGCCTAGAGAGGAACAGTACAACTCCACCTACCGGGTGGTGTCCGTGCTGACCGTGCTGCACCAGGATTGGCTGAACGGCAAAGAGTACAAGTGCAAGGTGTCCAACAAGGCCCTGCCTGCCCCCATCGAAAAGACCATCTCCAAGGCCAAGGGCCAGCCCCGGGAACCCCAGGTGTACACACTGCCCCCTAGCAGGGACGAGCTGACCAAGAACCAGGTGTCCCTGAGCTGTGCAGTGAAAGGCTTCTACCCCTCCGACATTGCCGTGGAATGGGAGTCCAACGGCCAGCCTGAGAACAACTACAAGACCACCCCCCCTGTGCTGGACTCCGACGGCTCATTCTTCCTGGTGAGCAAGCTGACAGTGGACAAGTCCCGGTGGCAGCAGGGCAACGTGTTCTCCTGCTCCGTGATGCACGAGGCCCTGCACAACCACTACACCCAGAAGTCCCTGTCCCTGAGCCCCGGCAAATGA |
| 21 | 21 | Anti-Her2(T)-Fc1 light chain | MSVPTQVLGLLLLWLTDARCDIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 39 | ATGTCTGTGCCTACCCAGGTGCTGGGACTGCTGCTGCTGTGGCTGACAGACGCCCGCTGTGACATTCAGATGACCCAGAGCCCCTCCTCCCTCTCCGCCTCCGTGGGAGACAGAGTTACCATCACCTGCAGGGCCTCCCAGGACGTGAACACCGCCGTGGCCTGGTACCAGCAGAAACCCGGCAAAGCCCCCAAACTGCTCATCTACTCCGCCTCATTTCTGTACAGCGGCGTGCCCTCCCGCTTCTCCGGTTCCAGATCCGGCACCGACTTCACCCTGACATATCTCCTCCCCTCCAGCCCGAAGACTTCGCCACCTACTACTGCCAGCAGCATACTACACCACCCCCCCCACCTTCGGCCAGGGCACAAAGGTCGAAATCAAGAGAACCGTGGCCGCTCCCTCCGTGTTCATCTTTCCCACCTTCCGACGAGCAGCTGAAGTCCGGCACCGCTTCTGTCGTGTGCCTGCTGAACAACTTCTACCCCGCGAGGCCAAGGTGCAGTGGAAGGTGGACAACGCCCTGCAGTCCGGCAACTCCCAGGAATCCGTGACCGAGCAGGACTCCAAGGACAGCACCTACTCCCTGTCCTCCACCCTGACCCTGTCCAAGGCCGACTACGAGAAGCACAAGGTGTACGCCTGCGAAGTGACCCACCAGGGCCTGTCAGCCCCGTGACCAAGTCTTTCAACCGGGGCGAGTGCTGA |
| 22 | 22 | Anti-Her2(P)-Fc1 heavy chain | MEWSWVFLFFLSVTTGVHSEVQLVESGGGLVQPGGSLRLSCAASGFTFTDYTMDWVRQAPGKGLEWVADVNPNSGGSIYNQRFKGRFTLSVDRSKNTLYLQMNSLRAEDTAVYYCARNLGPSFYFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK | 40 | ATGGAATGGAGCTGGGTGTTCCTGTTCTTTCTGTTCCTGTCACAGGCGTGCATTCTGAGGTGCAGTTGGTGGAGAGCGGGGGGGGCTGGTGCAGCCTGGAGGAAGTTTGAGGTTGAGCTGTGCCGCAAGCGGGTTCACATTTACAGACTACACAATGGACAGAGATTCAAGGGCCGGTTCACCTTGTCCGTGGACAGGAGCAAGAACACACTGTACCTGCAGATGAACAGCCTGAGGGCCGAGGATACCGCCGTCTACTATTGCGCCAGGAACCTCGGACCTTCCTTCTATTTTGACTACTGGGGCCAGGGAACCCTGGTGACCGTGTCATCTGCTTCTACCAAGGGCCCCTCCGTGTTTCCTCTGGCCCCTTCCAGCAAGTCCACCTCTGGCGGAACAGCCGCTCTGGGCTGCCTCGTGAAGGACTACTTCCCCGAGCCTGTGACCGTGTCCTGGAACTCTGGCGCTCTGACATCCGGCGTGCACACCTTCCCTGCTGTGCTGCAGTCTAGCGGCCTGTACTCCCTGTCCTCCGTCGTGACCGTGCCTTCCAGCTCTCTGGGCACCCAGACCTACATCTGCAACGTGAACCACAAGCCCTCCAACACCAAGGTGGACAAGAAGGTGGAACCCAAGTCCTGCGACAAGACCCACACCTGTCCCCCTTGTCCTGCCCCTGAACTGCTGGGCGGACCTTCCGTGTTCCTGTTCCCCCCAAAAGCCCAAGGACACCCTGATGATCTCCCGGACCCCCGAAGTGACCTGCGTGGTGGATGTGTCCCACGAGGACCCTGAAGTGAAGTTCAATTGGTACGTGGACGGCGTGGAAGTGCACAACGCCAAGACCAAGCCTAGAGAGGAACAGTACAACTCCACCTACCGGGTGGTGTCCGTGCTGACCGTGCTGCACCAGGATTGGCTGAACGGCAAAGAGTACAAGTGCAAGGTGTCCAACAAGGCCCTGCCTGCCCCCATCGAAAAGACCATCTCCAAGGCCAAGGGCCAGCCCCGGGAACCCCAGGTGTACACACTGCCCCCTAGCAGGGACGAGCTGACCAAGAACCAGGTGTCCCTGAGCTGTGCAGTGAAAGGCTTCTACCCCTCCGACATTGCCGTGGAATGGGAGTCCAACGGCCAGCCTGAGAACAACTACAAGACCACCCCCCCTGTGCTGGACTCCGACGGCTCATTCTTCCTGGTGAGCAAGCTGACAGTGGACAAGTCCCGGTGGCAGCAGGGCAACGTGTTCTCCTGCTCCGTGATGCACGAGGCCCTGCACAACCACTACACCCAGAAGTCCCTGTCCCTGAGCCCCGGCAAATGA |
| 23 | 23 | Anti-Her2(P)-Fc1 light chain | MSVPTQVLGLLLLWLTDARCDIQMTQSPSSLSASVGDRVTITCKASQDVSIGVAWYQQKPGKAPKLLIYSASYRYTGVPSRFSGSGSGTDFTLTISSLQPEDFATYYCQQYIYPYTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 41 | ATGTCTGTGCCTACCCAGGTGCTGGGACTGCTGCTGCTGTGGCTGACAGACGCCCGCTGTGACATTCAGATGACCCAGAGCCCCTCCTCCCTCTCCGCCTCCGTGGGAGACAGAGTTACCATCACCTGCAAAGCCAGCCAGGACGTGAGCATCGGCGTGGCCTGGTACCAGCAGAAACCCGGCAAAGCCCCCAAACTGCTCATTTACTCCGCCTCATACCGTTACACCGGCGTTCCCTCCCGCTTCAGCGGATCCGGCTCCGGAACCGACTTCACCCTGACATATCTCCTCCCCTCCAGCCCGAAGACTTCGCCACCTACTACTGCCAGCAGTACTACATTTACCCCTACACCTTCGGCCAGGGCACCAAGGTGGAAATCAAGAGAACCGTGGCCGCTCCCTCCGTGTTCATCTTTCCCACCTTCCGACGAGCAGCTGAAGTCCGGCACCGCTTCTGTCGTGTGCCTGCTGAACAACTTCTACCCCGCGAGGCCAAGGTGCAGTGGAAGGTGGACAACGCCCTGCAGTCCGGCAACTCCCAGGAATCCGTGACCGAGCAGGACTCCAAGGACAGCACCTACTCCCTGTCCTCCACCCTGACCCTGTCCAAGGCCGACTACGAGAAGCACAAGGTGTACGCCTGCGAAGTGACCCACCAGGGCCTGTCAGCCCCGTGACCAAGTCTTTCAACCGGGGCGAGTGCTGA |
| 24 | 24 | Anti-PD-L1(Ate)-Fc1 heavy chain | MEWSWVFLFFLSVTTGVHSEVQLVESGGGLVQPGGSLRLSCAASGFTFSDSWIHWVRQAPGKGLEWVAWISPYGGSTYYADSVKGRFTISADTSKNTAYLQMNSLRAEDTAVYYCARRHWPGGFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK | 42 | ATGGAATGGAGCTGGGTGTTCCTGTTCTTTCTGTTCCTGTCACAGGCGTGCATTCTGAAGTGCAGCTGGTGGAAAGCGGCGGCGGCCTGGTGCAGCCTGGCGGCAGCCTGCGCCTGAGCTGCGCCGCGAGCGGCTTTACCTTTAGCGATAGCTGGATTCATTGGGTGCGCCAGGCGCCGGGCAAAGGCCTGGAATGGGTGGCGTGGATTAGCCCGTATGGCGGCAGCACCTATTATGCGGATAGCGTGAAAGGCCGCTTTACCATTAGCGCGGATACCAGCAAAAACACCGCGTATCTGCAGATGAACAGCCTGCGCGCGGAAGATACCGCGGTGTATTATTGCGCGCGTCGCCATTGGCCGGGCGGCTTTGATTACTGGGGCCAGGGCACCCTGGTGACCGTGTCATCTGCTTCTACCAAGGGCCCCTCCGTGTTTCCTCTGGCCCCTTCCAGCAAGTCCACCTCTGGCGGAACAGCCGCTCTGGGCTGCCTCGTGAAGGACTACTTCCCCGAGCCTGTGACCGTGTCCTGGAACTCTGGCGCTCTGACATCCGGCGTGCACACCTTCCCTGCTGTGCTGCAGTCTAGCGGCCTGTACTCCCTGTCCTCCGTCGTGACCGTGCCTTCCAGCTCTCTGGGCACCCAGACCTACATCTGCAACGTGAACCACAAGCCCTCCAACACCAAGGTGGACAAGAAGGTGGAACCCAAGTCCTGCGACAAGACCCACACCTGTCCCCCTTGTCCTGCCCCTGAACTGCTGGGCGGACCTTCCGTGTTCCTGTTCCCCCCAAAAGCCCAAGGACACCCTGATGATCTCCCGGACCCCCGAAGTGACCTGCGTGGTGGATGTGTCCCACGAGGACCCTGAAGTGAAGTTCAATTGGTACGTGGACGGCGTGGAAGTGCACAACGCCAAGACCAAGCCTAGAGAGGAACAGTACAACTCCACCTACCGGGTGGTGTCCGTGCTGACCGTGCTGCACCAGGATTGGCTGAACGGCAAAGAGTACAAGTGCAAGGTGTCCAACAAGGCCCTGCCTGCCCCCATCGAAAAGACCATCTCCAAGGCCAAGGGCCAGCCCCGGGAACCCCAGGTGTACACACTGCCCCCTAGCAGGGACGAGCTGACCAAGAACCAGGTGTCCCTGAGCTGTGCAGTGAAAGGCTTCTACCCCTCCGACATTGCCGTGGAATGGGAGTCCAACGGCCAGCCTGAGAACAACTACAAGACCACCCCCCCTGTGCTGGACTCCGACGGCTCATTCTTCCTGGTGAGCAAGCTGACAGTGGACAAGTCCCGGTGGCAGCAGGGCAACGTGTTCTCCTGCTCCGTGATGCACGAGGCCCTGCACAACCACTACACCCAGAAGTCCCTGTCCCTGAGCCCCGGCAAATGA |
| 25 | 13 | Anti-PD-L1(Ate)-Fc1 light chain | MEFWLSWVFLVAILKGVQCDIQMTQSPSSLSASVGDRVTITCRASQDVSTAVAWYQQKPGKAPKLLIYSASFLYSGVPSRFSGSGSGTDFTLTISSLQPEDFATYYCQQYLYHPATFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | / | / |

Fig. 17C

| No. | SEQ ID NOs: | Sequence name | Protein sequence | SEQ ID NOs: | DNA Sequence |
|---|---|---|---|---|---|
| 26 | 26 | D1-Fc2 | MEWSWVFLFFLSVTTGVHSEEELQVIQPDKSVSVA AGESAILHCTVTSLIPVGPIQWFRGAGPARELIYN QKEGHFPRVTTVSESTKRENMDFSISISAITPADA GTYYCVKFRKGSPDTEFKSGAGTELSVRAKPDKTH TCPPCPAPELLGGPSVFLFPPKPKDTLMISRTPEV TCVVVDVSHEDPEVKFNWYVDGVEVHNAKTKPREE QYNSTYRVVSVLTVLHQDWLNGKEYKCKVSNKALP APIEKTISKAKGQPREPQVYTLPPSRDELTKNQVS LWCLVKGFYPSDIAVEWESNGQPENNYKTTPPVLD SDGSFFLYSKLTVDKSRWQQGNVFSCSVMHEALHN HYTQKSLSLSPGK | 14 | ATGGAATGGAGCTGGGTGTTCCTGTTCTTTCTGTCCGTGACCACAGGCGTGCATTCTGAAGAGGAGCTGC AGGTCATCCAGCCCGATAAGGAGCGTGTCCGTGGCCGCAGGAGAATCTGCCATCCTGCATTGCACCGTGAC CTCTCTGATCCCCGTGGGCCCAATCCAGTGGTTCAGAGGAGCCGGACCAGCTAGAGAGCTGATCTACAAC CAGAAGGAGGGCCACTTCCCCAGAGTGACAACCGTGTCCGAGTCTACCAAGCGGGAGAACATGGACTTCT CCATCTCCATCTCCGCCATCACACCAGCCGACGCCGGCACCTACTATTGCGTGAAGTTCCGGAAGGGCTC CCCAGATACCGAGTTTAAGAGCGGCGCCGGAACAGAGCTGAGCGTGCGGGCTAAGCCTGACAAGACCCAC ACCTGTCCCCCTTGTCCTGCCCCTGAACTGCTGGGCGGACCTTCCGTGTTCCTGTTCCCCCCAAAGCCCA AGGACACCCTGATGATCTCCCGGACCCCCGAAGTGACCTGCGTGGTGGTGGATGTGTCCCACGAGGACCC TGAAGTGAAGTTCAATTGGTACGTGGACGGCGTGGAAGTGCACAACGCCAAGACCAAGCCTAGAGAGGAA CAGTACAACTCCACCTACCGGGTGGTGTCCGTGCTGACCGTGCTGCACCAGGATTGGCTGAACGGCAAAG AGTACAAGTGCAAGGTGTCCAACAAGGCCCTGCCTGCCCCCATCGAAAAGACCATCTCCAAGGCCAAGGG CCAGCCCCGGGAACCCCAGGTGTACACACTGCCCCCTAGCAGGGACGAGCTGACCAAGAACCAGGTGTCC CTGTGGTGTCTCGTGAAAGGCTTCTACCCCTCCGACATTGCCGTGGAATGGGAGTCCAACGGCCAGCCTG AGAACAACTACAAGACCACCCCCCCTGTGCTGGACTCCGACGGCTCATTCTTCCTGTACAGCAAGCTGAC AGTGGACAAGTCCCGGTGGCAGCAGGGCAACGTGTTCTCCTGCTCCGTGATGCACGAGGCCCTGCACAAC CACTACACCCAGAAGTCCCTGTCCCTGAGCCCCGGCAAATGA |
| 27 | 27 | D1-D2-Fc2 | MEWSWVFLFFLSVTTGVHSEEELQVIQPDKSVSVA AGESAILHCTVTSLIPVGPIQWFRGAGPARELIYN QKEGHFPRVTTVSESTKRENMDFSISISAITPADA GTYYCVKFRKGSPDTEFKSGAGTELSVRAKPSAPV VSGPAARATPQHTVSFTCESHGFSPRDITLKWFKN GNELSDFQTNVDPVGESVSYSIHSTAKVVLTREDV HSQVICEVAHVTLQGDPLRGTANLSDKTHTCPPCP APELLGGPSVFLFPPKPKDTLMISRTPEVTCVVVD VSHEDPEVKFNWYVDGVEVHNAKTKPREEQYNSTY RVVSVLTVLHQDWLNGKEYKCKVSNKALPAPIEKT ISKAKGQPREPQVYTLPPSRDELTKNQVSLWCLVK GFYPSDIAVEWESNGQPENNYKTTPPVLDSDGSFF LYSKLTVDKSRWQQGNVFSCSVMHEALHNHYTQKS LSLSPGK | 15 | ATGGAATGGAGCTGGGTGTTCCTGTTCTTTCTGTCCGTGACCACAGGCGTGCATTCTGAAGAGGAGCTGC AGGTCATCCAGCCCGATAAGAGCGTGTCCGTGGCCGCAGGAGAATCTGCCATCCTGCATTGCACCGTGAC CTCTCTGATCCCCGTGGGCCCAATCCAGTGGTTCAGAGGAGCCGGACCAGCTAGAGAGCTGATCTACAAC CAGAAGGAGGGCCACTTCCCCAGAGTGACAACCGTGTCCGAGTCTACCAAGCGGGAGAACATGGACTTCT CCATCTCCATCTCCGCCATCACACCAGCCGACGCCGGCACCTACTATTGCGTGAAGTTCCGGAAGGGCTC CCCAGATACCGAGTTTAAGAGCGGCGCCGGAACAGAGCTGAGCGTGCGGGCTAAGCCTTCTGCTCCAGTG GTGTCAGGACCAGCAGCTAGAGCTACCCCTCAGCACACCGTGTCCTTCACCTGCGAGTCTCACGGCTTCT CCCCTAGAGACATCACCCTCAAGTGGTTCAAGAACGGCAACGAGCTGTCCGACTTCCAGACCAACGTGGA TCCAGTGGGCGAGAGCGTGTCTTACTCCATCCACTCCACCGCCAAGGTGGTGCTGACAAGGGAGGACGTG CACTCCCAGGTCATTTGCGAGGTGGCACACGTGACATTGCAGGGCGACCCCCTGAGGGGAACCGCCAACT TGAGTGACAAGACCCACACCTGTCCCCCTTGTCCTGCCCCTGAACTGCTGGGCGGACCTTCCGTGTTCCT GTTCCCCCCAAAGCCCAAGGACACCCTGATGATCTCCCGGACCCCCGAAGTGACCTGCGTGGTGGTGGAT GTGTCCCACGAGGACCCTGAAGTGAAGTTCAATTGGTACGTGGACGGCGTGGAAGTGCACAACGCCAAGA CCAAGCCTAGAGAGGAACAGTACAACTCCACCTACCGGGTGGTGTCCGTGCTGACCGTGCTGCACCAGGA TTGGCTGAACGGCAAAGAGTACAAGTGCAAGGTGTCCAACAAGGCCCTGCCTGCCCCCATCGAAAAGACC ATCTCCAAGGCCAAGGGCCAGCCCCGGGAACCCCAGGTGTACACACTGCCCCCTAGCAGGGACGAGCTGA CCAAGAACCAGGTGTCCCTGTGGTGTCTCGTGAAAGGCTTCTACCCCTCCGACATTGCCGTGGAATGGGA GTCCAACGGCCAGCCTGAGAACAACTACAAGACCACCCCCCCTGTGCTGGACTCCGACGGCTCATTCTTC CTGTACAGCAAGCTGACAGTGGACAAGTCCCGGTGGCAGCAGGGCAACGTGTTCTCCTGCTCCGTGATGC ACGAGGCCCTGCACAACCACTACACCCAGAAGTCCCTGTCCCTGAGCCCCGGCAAATGA |
| 28 | 28 | D1-D2-D3-Fc2 | MEWSWVFLFFLSVTTGVHSEEELQVIQPDKSVSVA AGESAILHCTVTSLIPVGPIQWFRGAGPARELIYN QKEGHFPRVTTVSESTKRENMDFSISISAITPADA GTYYCVKFRKGSPDTEFKSGAGTELSVRAKPSAPV VSGPAARATPQHTVSFTCESHGFSPRDITLKWFKN GNELSDFQTNVDPVGESVSYSIHSTAKVVLTREDV HSQVICEVAHVTLQGDPLRGTANLSETIRVPPTLE VTQQPVRAENQVNVTCQVRKFYPQRLQLTWLENGN VSRTETASTVTENKDGTYNWMSWLLVNVSAHRDDV KLTCDKTHTCPPCPAPELLGGPSVFLFPPKPKDTL MISRTPEVTCVVVDVSHEDPEVKFNWYVDGVEVHN AKTKPREEQYNSTYRVVSVLTVLHQDWLNGKEYKC KVSNKALPAPIEKTISKAKGQPREPQVYTLPPSRD ELTKNQVSLWCLVKGFYPSDIAVEWESNGQPENNY KTTPPVLDSDGSFFLYSKLTVDKSRWQQGNVFSCS VMHEALHNHYTQKSLSLSPGK | 25 | ATGGAATGGAGCTGGGTGTTCCTGTTCTTTCTGTCCGTGACCACAGGCGTGCATTCTGAAGAGGAGCTGC AGGTCATCCAGCCCGATAAGAGCGTGTCCGTGGCCGCAGGAGAATCTGCCATCCTGCATTGCACCGTGAC CTCTCTGATCCCCGTGGGCCCAATCCAGTGGTTCAGAGGAGCCGGACCAGCTAGAGAGCTGATCTACAAC CAGAAGGAGGGCCACTTCCCCAGAGTGACAACCGTGTCCGAGTCTACCAAGCGGGAGAACATGGACTTCT CCATCTCCATCTCCGCCATCACACCAGCCGACGCCGGCACCTACTATTGCGTGAAGTTCCGGAAGGGCTC CCCAGATACCGAGTTTAAGAGCGGCGCCGGAACAGAGCTGAGCGTGCGGGCTAAGCCTTCTGCTCCAGTG GTGTCAGGACCAGCAGCTAGAGCTACCCCTCAGCACACCGTGTCCTTCACCTGCGAGTCTCACGGCTTCT CCCCTAGAGACATCACCCTCAAGTGGTTCAAGAACGGCAACGAGCTGTCCGACTTCCAGACCAACGTGGA TCCAGTGGGCGAGAGCGTGTCTTACTCCATCCACTCCACCGCCAAGGTGGTGCTGACAAGGGAGGACGTG CACTCCCAGGTCATTTGCGAGGTGGCACACGTGACATTGCAGGGCGACCCCCTGAGAGGCACAGCAAACT TGAGCGAGACAATTAGAGTGCCCCCCACCCTGGAAGTTACACAGCAGCCCGTTAGAGCCGAGAACCAGGT CAACGTCACCTGCCAGGTACGAAAGTTTTATCCACAGAGACTGCAGCTGACCTGGCTCGAGAACGGAAAC GTGAGCAGAACAGAGACCGCCAGCACCGTGACAGAGAACAAGGACGGGAGCCTACAACTGATGAGTTGGC TGCTGGTGAACGTCAGCGCCCACAGAGACGACGTCAAGCTGACCTGCGACAAGACCCACACCTGTCCCCC TTGTCCTGCCCCTGAACTGCTGGGCGGACCTTCCGTGTTCCTGTTCCCCCCAAAGCCCAAGGACACCCTG ATGATCTCCCGGACCCCCGAAGTGACCTGCGTGGTGGTGGATGTGTCCCACGAGGACCCTGAAGTGAAGT TCAATTGGTACGTGGACGGCGTGGAAGTGCACAACGCCAAGACCAAGCCTAGAGAGGAACAGTACAACTC CACCTACCGGGTGGTGTCCGTGCTGACCGTGCTGCACCAGGATTGGCTGAACGGCAAAGAGTACAAGTGC AAGGTGTCCAACAAGGCCCTGCCTGCCCCCATCGAAAAGACCATCTCCAAGGCCAAGGGCCAGCCCCGGG AACCCCAGGTGTACACACTGCCCCCTAGCAGGGACGAGCTGACCAAGAACCAGGTGTCCCTGTGGTGTCT CGTGAAAGGCTTCTACCCCTCCGACATTGCCGTGGAATGGGAGTCCAACGGCCAGCCTGAGAACAACTAC AAGACCACCCCCCCTGTGCTGGACTCCGACGGCTCATTCTTCCTGTACAGCAAGCTGACAGTGGACAAGT CCCGGTGGCAGCAGGGCAACGTGTTCTCCTGCTCCGTGATGCACGAGGCCCTGCACAACCACTACACCCA GAAGTCCCTGTCCCTGAGCCCCGGCAAATGA |
| 29 | 29 | D1"-Fc2 | MEWSWVFLFFLSVTTGVHSEEELQIIQPDKSVSVA AGESAILHCTITSLFPVGPIQWFRGAGPARVLIYN QRQGPFPRVTTVSETTKRENMDFSISISNITPADA GTYYCIKFRKGSPDTEFKSGAGTELSVRAKPSEPK SSDKTHTCPPCPAPELLGGPSVFLFPPKPKDTLMI SRTPEVTCVVVDVSHEDPEVKFNWYVDGVEVHNAK TKPREEQYNSTYRVVSVLTVLHQDWLNGKEYKCKV SNKALPAPIEKTISKAKGQPREPQVYTLPPSRDEL TKNQVSLWCLVKGFYPSDIAVEWESNGQPENNYKT TPPVLDSDGSFFLYSKLTVDKSRWQQGNVFSCSVM HEALHNHYTQKSLSLSPGK | 43 | ATGGAGTGGAGCTGGGTGTTCTTGTTCTTTCTTGTCCGTGACCACCGGGGTGCACAGCGAGGAGGAGTTGC AGATCATCCAGCCTGACAAGAGCGTGAGCGTGGCCGCCGGGGAGAGCGCTATTCTGCACTGTACCATCAC CTCCCTCTTCCCCGTGGGCCCCATTCAGTGGTTCAGGGGAGCCGGGCCCGCCAGAGTTCTGATTTACAAC CAGAGGCAGGGCCCCTTTCCCCGGGTTACCACTGTCTCTGAGACCACCAAGCGGGAGAACATGGATTTCA GCATCTCCATCAGCAACATTACTCCCGCCGACGCCGGCACCTACTACTGCATCAAATTCAGAAAGGGCTC TCCCGACACCGAATTCAAAAGCGGCGCCGGCACCGAACTGTCCGTGCGAGCTAAGCCTTCCGAGCCCAAA TCCTCAGACAAGACCCACACCTGTCCCCCTTGTCCTGCCCCTGAACTGCTGGGCGGACCTTCCGTGTTCC TGTTCCCCCCAAAGCCCAAGGACACCCTGATGATCTCCCGGACCCCCGAAGTGACCTGCGTGGTGGTGGA TGTGTCCCACGAGGACCCTGAAGTGAAGTTCAATTGGTACGTGGACGGCGTGGAAGTGCACAACGCCAAG ACCAAGCCTAGAGAGGAACAGTACAACTCCACCTACCGGGTGGTGTCCGTGCTGACCGTGCTGCACCAGG ATTGGCTGAACGGCAAAGAGTACAAGTGCAAGGTGTCCAACAAGGCCCTGCCTGCCCCCATCGAAAAGAC CATCTCCAAGGCCAAGGGCCAGCCCCGGGAACCCCAGGTGTACACACTGCCCCCTAGCAGGGACGAGCTG ACCAAGAACCAGGTGTCCCTGTGGTGTCTCGTGAAAGGCTTCTACCCCTCCGACATTGCCGTGGAATGGG AGTCCAACGGCCAGCCTGAGAACAACTACAAGACCACCCCCCCTGTGCTGGACTCCGACGGCTCATTCTT CCTGTACAGCAAGCTGACAGTGGACAAGTCCCGGTGGCAGCAGGGCAACGTGTTCTCCTGCTCCGTGATG CACGAGGCCCTGCACAACCACTACACCCAGAAGTCCCTGTCCCTGAGCCCCGGCAAATGA |

Fig. 17D

| No. | SEQ ID NOs: | Sequence name | Protein sequence |
|---|---|---|---|
| 30 | 30 | D1 | EEELQVIQPDKSVSVAAGESAILHCTVTSLIPVGPIQWFRGAGPARELIYNQKEGHFPRVTTVSESTKRENMDFSISISAI TPADAGTYYCVKFRKGSPDTEFKSGAGTELSVRAKP |
| 31 | 31 | D1-D2 | EEELQVIQPDKSVSVAAGESAILHCTVTSLIPVGPIQWFRGAGPARELIYNQKEGHFPRVTTVSESTKRENMDFSISISAI TPADAGTYYCVKFRKGSPDTEFKSGAGTELSVRAKPSAPVVSGPAARATPQHTVSFTCESHGFSPRDITLKWFKNGNELSD FQTNVDPVGESVSYSIHSTAKVVLTREDVHSQVICEVAHVTLQGDPLRGTANLS |
| 32 | 32 | D1-D2-D3 | EEELQVIQPDKSVSVAAGESAILHCTVTSLIPVGPIQWFRGAGPARELIYNQKEGHFPRVTTVSESTKRENMDFSISISAI TPADAGTYYCVKFRKGSPDTEFKSGAGTELSVRAKPSAPVVSGPAARATPQHTVSFTCESHGFSPRDITLKWFKNGNELSD FQTNVDPVGESVSYSIHSTAKVVLTREDVHSQVICEVAHVTLQGDPLRGTANLSETIRVPPTLEVTQQPVRAENQVNVTCQ VRKFYPQRLQLTWLENGNVSRTETASTVTENKDGTYNWMSWLLVNVSAHRDDVKLTC |
| 33 | 33 | D1ᵐ | EEELQIIQPDKSVSVAAGESAILHCTITSLFPVGPIQWFRGAGPARVLIYNQRQGPFPRVTTVSETTKRENMDFSISISNI TPADAGTYYCIKFRKGSPDTEFKSGAGTELSVRAKPSEPKSS |
| 34 | 44 | D1ᵐ-D2-Fc2 | MEWSWVFLFFLSVTTGVHSEEELQIIQPDKSVSVAAGESAILHCTITSLFPVGPIQWFRGAGPARVLIYNQRQGPFPRVTT VSETTKRENMDFSISISNITPADAGTYYCIKFRKGSPDTEFKSGAGTELSVRAKPSEPKSSGPAARATPQHTVSFTCESHG FSPRDITLKWFKNGNELSDFQTNVDPVGESVSYSIHSTAKVVLTREDVHSQVICEVAHVTLQGDPLRGTANLSDKTHTCPP CPAPELLGGPSVFLFPPKPKDTLMISRTPEVTCVVVDVSHEDPEVKFNWYVDGVEVHNAKTKPREEQYNSTYRVVSVLTVL HQDWLNGKEYKCKVSNKALPAPIEKTISKAKGQPREPQVYTLPPSRDELTKNQVSLWCLVKGFYPSDIAVEWESNGQPENN YKTTPPVLDSDGSFFLYSKLTVDKSRWQQGNVFSCSVMHEALHNHYTQKSLSLSPGK |

BISPECIFIC RECOMBINANT PROTEIN AND USE THEREOF

The present application is a National Stage of International Application No. PCT/CN2018/086050, filed on May 8, 2018, which claims priority of the Chinese Patent Application No. CN201710317926.7 filed on May 8, 2017 and the Chinese Patent Application No. CN201711269620.5 filed on Dec. 5, 2017, the contents of which are incorporated herein by reference in their entireties.

FIELD OF INVENTION

The present disclosure belongs to the field of biomedicine, particularly relates to a recombinant protein and a use thereof.

PRIOR ARTS

With the deepening research in the field of cancer therapy, the research, development and application of molecular targeted therapeutic drugs for cancer have received more and more attention. Owing to the advantages of strong targetability, minimal side effects and remarkable therapeutic effects, antibody drugs have rapidly become hot spot of targeted cancer therapy. There are already dozens of tumor-targeting antibody drugs approved for clinical use, which have achieved significant therapeutic effects. The antibody drugs includes, for example, the antibodies targeting CD20, such as Rituxan® (rituximab, which is developed by Roche, is the first monoclonal antibody approved for treating cancer in the United States, and originally used to treat non-Hodgkin's lymphoma), Zevalin® (ibritumomab tiuxetan, which is developed by IDEC Pharmaceuticals, is originally approved for treating low-differentiated non-Hodgkin's lymphoma with resistance to Rituxan® by the FDA), Bexxar® (tositumomab and iodine I$^{131}$ tositurnotnab, GSK), Arzerra® (ofatumutnab, GSK); the antibodies targeting Her2; such as Herceptin® (trastuzumab, which is developed by Genentech, is a well-known drug for treating breast cancer), Perjeta® (pertuzumab, Roche), Kadcyla® (ado-trastuzumabemtansine, Roche); the antibodies targeting VEGF or its receptor, such as Avastin® (bevacizumab, Genentech/Roche), Cyramaza® (ramucirumab, Eli Lilly); the antibodies targeting EGFR, such as Erbitux® (cetuximab, which is developed by Eli Lilly, is one of the top 10 best-selling anticancer drugs in the world, and originally approved for treating rectal cancer), Vectibix® (panitumumab, which is developed by Amgen for treating colorectal cancer); the antibodies targeting PD-L1, such as Tecentriq® (atezolizumab, Roche) (Cao Rui et al., Advances in antibody drugs for cancer targeted therapy, *Chinese Journal of Biochemical Pharmaceutics*, 2016, 36(6): 15-18).

Clinically applied anti-tumor antibody drugs that target tumor cells (unconjugated naked antibodies) achieve anti-tumor effect mainly by two functions of antibodies. The first function of antibodies is affinity, i.e., specifically binding to the target antigen on the surface of tumor cells and exerting its effector function to kill the tumor cells. Antibody molecules can block the tumor growth factor signaling pathway, induce apoptosis, or inhibit the neovascularization in the tumor microenvironment by binding to the target antigen. The second function of antibodies is achieved through the immune system, i.e., relying on the immune system to mediate cell death to achieve the effect of killing tumor cells, such as antibody-dependent cell-mediated cytotoxicity (ADCC) mediated by constant region of antibodies, complement dependent cytotoxicity (CDC) and antibody dependent cellular phagocytosis (ADCC). More and more researches show the cytotoxicity of antibody-mediated immune response is an important mechanism of the anti-tumor activity of antibodies (for review, see Barnhart B C, et al. Role of Fc-FcγR interactions in the antitumor activity of therapeutic antibodies. *Immunology and Cell Biology*, 2017, 95: 340-346).

In recent years, studies have confirmed that tumor cells can continually divide and grow by modifying their own surface antigens and changing the microenvironment around the tumor tissue to escape the surveillance, recognition and attack of the innate immune system, i.e., the so-called tumor immune escape. For example, tumor cells inhibit the immune function of macrophages and significantly inhibit the activity of immune cells by highly expressing CD47 which binds to the inhibitory receptor signal-regulatory protein α (SIRPα) on the surface of macrophages. Meanwhile, high expression of CD47 on tumor cells inhibits Fc receptor-mediated phagocytosis, ultimately affecting the targeted cancer therapeutic effects of antibody drugs (Willingham S B, et al. The CD47-signal regulatory protein Alpha (SIRPα) interaction is a therapeutic target for human solid tumors. *Proceedings of the National Academy of Sciences of the united States of America*. 2012, 109(17): 6662-6667).

CD47 is a widely expressed membrane glycoprotein, which interacts with SIRPα as mutual receptor and ligand and forms a CD47-SIRPα, signal complex, thus triggering a series of reactions such as apoptosis, proliferation and immunity. In 2000, Oldenborg et al. demonstrated that CD47 is an important signal marker on cell surface for regulating macrophage phagocytosis (Oldenborg P A, et al. Role of CD47 as a marker of self on red blood cells. *Science*, 2000, 288 (5473): 2051-2054). CD47 releases a "don't eat me" signal, by binding to SIRPα on the surface of macrophages, phosphorylating its immune receptor tyrosine-based inhibitory motif (ITIM), subsequently recruiting SH2-containing protein tyrosine phosphatase 1 protein, and triggering a series of cascades to inhibit the phagocytosis of macrophages. The younger red blood cells (RBCs) highly express CD47 and release a signal of "I am your ally, don't eat me" to macrophages, while the aged RBCs down-regulate the expression of CD47 and are eventually eliminated by macrophages.

CD47 can be a target for treating various cancers because it is widely expressed on the surface of various cancer cells. The mouse allogeneic tumor transplantation model has demonstrated the effectiveness of CD47 blockade, so CD47 has become a novel target of immune checkpoint therapy for cancer (Vonderhei de R H. CD47 blockade as another immune checkpoint therapy for cancer. *Nature Medicine*, 2015, 21(10): 1122-1123). The anti-CD47 antibody, SIRPα-Fc fusion protein and the like can relieve the inhibitory effect of CD47 on immune cells by blocking the CD47-SIRPα signaling pathway, and exhibit certain anti-tumor activity. However, since RBCs also highly express CD47 protein, the treatment with anti-CD47 antibody which binds to CD47 protein with high affinity may cause toxic side effects such as RBC agglutination and anemia (Mccracken M N, et al. Molecular Pathways: Activating T Cells after Cancer Cell Phagocytosis from Blockade of CD47 "Don't Eat Me" Signals. *Clinical Cancer Research*, 2015, 21(16): 3597-3601), which makes the clinical development of anti-CD47 antibody drugs very difficult. There is no anti-CD47 antibody drugs entering phase III clinical trials so far. The wild-type SIRPα-Fc fusion protein does not have potent efficacy due to its low affinity to CD47. Some researchers obtain SIRPα mutants with a thousand-fold affinity enhancement and better anti-tumor efficacy by high affinity mutations in wild-type SIRPα (Weiskopf K., et al. Engineered SIRPα variants as immunotherapeutic adjuvants to anticancer antibodies. *Science*, 2013, 341 (6141): 88-91). However, it remains to be clinically proved whether multiple point mutations affect the safety, immunogenicity, stability and even target specificity of the fusion proteins in humans.

On the other hand, studies have shown that the anti-tumor efficacy of anti-CD47 antibodies can be significantly improved by combining with other tumor-targeting therapeutic antibodies, such as a combination therapy with CD47+CD20, CD47+Her2 (Chao M P, et al. Anti-CD47 antibody synergizes with rituximab to promote phagocytosis and eradicate non-Hodgkin lymphoma. *Cell*, 2010, 142(5): 699-713; Zhao X W, et al. CD47-signal regulatory protein-α (SIRPα) interactions form a barrier for antibody-mediated tumor cell destruction. *Proceedings of the National Academy of Sciences of the United States of America*. 2011, 108(45): 18342-18347). However, there is great uncertainty that whether and when the anti-CD47 antibody can be launched. Furthermore, even if the anti-CD47 antibody is available on the market, it is still difficult for patients to bear the combination therapy with tumor-targeting antibody drugs due to the high cost thereof.

Therefore, there is a need to develop a novel tumor-targeting drug, which can specifically target the tumor, activate and enhance immune function in patients, significantly improve the efficacy while ensuring safety, and reduce the cost of the medication in the meantime.

In addition, in view of the potential safety risks of monovalent or multivalent antibodies or recombinant proteins targeting CD47 (such as anemia, RBC agglutination, cytotoxicity of CD47-positive non-tumor target cells), the binding of human SIRPα to human CD47 is species-specific, while the application of human blood is restricted by ethics and the availability of genetic resources etc., an early immunological safety evaluation method for evaluating the immunological safety of antibodies or recombinant proteins targeting CD47 in vivo/in vitro is urgently needed.

Content of the Present Invention

The present disclosure provides a bispecific recombinant protein and a use thereof, which can significantly enhance the tumor-targeting saturation binding abundance of a recombinant protein with an effect of modulating the function of macrophages and reduce non-tumor-target side effects.

In one aspect, the present disclosure provides a bispecific recombinant protein, wherein the bispecific recombinant protein comprises a 'high affinity tumor-targeting arm' and a 'fusion protein with low affinity for blocking the interaction between CD47 and SIRPα'.

In one embodiment, the 'high affinity tumor-targeting arm' does not bind to CD47, and the ratio of the binding affinity of the antibody corresponding to the 'high affinity tumor-targeting arm' to the target antigen on tumor cell(s) to the binding affinity of the homodimer of a monomer fusion protein corresponding to the 'fusion protein with low affinity for blocking the interaction between CD47 and SIRPα' to CD47 on tumor cell(s) is at least 6, optionally 6, 7, 8, 9, 10, 11, 12, 13, 14, 15 or more, or any value between them;

The binding affinity of the 'fusion protein with low affinity for blocking the interaction between CD47 and SIRPα' to CD47 is not higher than the binding affinity of the homodimer of a 'monomer fusion protein comprising an extracellular truncated variant of SIRPα' to CD47. The 'fusion protein with low affinity for blocking the interaction between CD47 and SIRPα' comprises an extracellular truncated variant of SIRPα.

In one embodiment, the extracellular truncated variant of SIRPα comprises a part or full of the amino acid sequence of the extracellular domain of human SIRPα (wild-type or a variant with non-high affinity to CD47).

In one embodiment, the extracellular truncated variant of SIRPα is an extracellular truncated variant of human SIRPα. In a specific embodiment, the extracellular truncated variant of SIRPα comprises an amino acid sequence selected from the group consisting of a1), a2), a3) and a4): a1) SEQ ID No: 30; a2) SEQ ID No: 31; a3) SEQ ID No: 32; a4) an amino acid sequence obtained by inserting, deleting, modifying and/or conservatively substituting at least one amino acid residue such as 1-5 amino acid residue(s) of any one of the amino acid sequences described above, wherein the binding affinity of monomer thereof to a CD47 is not higher than the binding affinity of monomer of a1), a2) or a3) to a CD47.

In one embodiment, the bispecific recombinant protein has a configuration comprising a left arm and a right arm which are symmetrically arranged, wherein the 'high affinity tumor-targeting arm' is arranged in the left arm, and the 'fusion protein with low affinity for blocking the interaction between CD47 and SIRPα' is arranged in the right arm; preferably, the left arm is in the form of Fab or Fab' of immunoglobulin, and the right arm is an extracellular truncated variant of SIRPα. Wherein, the term 'a left arm and a right arm which are symmetrically arranged' herein is described with reference to the conventional 'Y' configuration of immunoglobulin, in this case, the left and right sides of the bispecific recombinant protein of the present disclosure have specific functional proteins targeting different targets respectively; this structural description mainly distinguish from the case that two specific functional proteins form an 'up-and-down' structure by linking the C-terminus and the N-terminus. Therefore, the spatial positions of the left and right arms described in the present disclosure are not specific limitations to the structure of the bispecific recombinant protein, only for distinguishing two arms structure of the recombinant protein from the "up-and-down" structure formed by linking the C-terminus and the N-terminus described above. It could be understand that when one arm is arranged in one side, the other arm is arranged on the other side; obviously, the left and right positions of the two arms are interchangeable.

In one embodiment, the length of the right arm is configured for the distance from the epitope to which the left arm binds to the membrane surface of the target cell. Preferably, when the 'high affinity tumor-targeting arm' is configured for binding a membrane-proximal epitope of the target cell, the extracellular truncated variant of SIRPα is selected from the shorter amino acid sequence among a1), a2), a3) and a4).

In one embodiment, the 'high affinity tumor-targeting arm' is specific to a target selected from the group consisting of 5T4, AGS-16, ALK1, ANG-2, B7-H3, B7-H4, c-fms, c-Met, CA6, CD123, CD19, CD20, CD22, EpCAM, CD30, CD32b, CD37, CD38, CD40, CD52, CD70, CD74, CD79b, CD98, CEA, CEACAM5, CLDN18.2, CLDN6, CS1, CXCR4, DLL-4, EGFR, EGP-1, ENPP3, EphA3, ETBR, FGFR2, FN, FR-α, GCC, GD2, GPC-3, GPNMB, HER2, HER3, HLA-DR, ICAM-1, IGF-1R, IL-3R, MSLN, MUC16, MUC1, NaPi2b, nectin-4, Notch 1, Notch 2, PD-L1, PD-L2, PDGFR-α, PS, PSMA, SLTRK6, STEAP1, TEM1, VEGFR, CD25, CD27L, DKK-1, CSF-1R, MSB0010718C, BCMA and CD138.

Preferably, when the target is CD20, EGFR or PD-L1, the extracellular truncated variant of SIRPα is a1); when the target is HER2, the extracellular truncated variant of SIRPα is a1) or a2).

In one embodiment, the 'high affinity tumor-targeting arm' and the 'fusion protein with low affinity for blocking the interaction between CD47 and SIRPα' are combined via two or three of the following bindings: intermolecular force, covalent bond (such as interchain disulfide bond) and salt bond.

In one embodiment, the 'high affinity tumor-targeting arm' and the 'fusion protein with low affinity for blocking the interaction between CD47 and SIRPα' further comprise an Fc region. Generally, the Fc region of the present disclosure comprises a natural sequence of Fc region. However, the Fc region of the present disclosure may have one or more change(s) or modification(s) of amino acid sequence on the natural sequence of Fc region, such as change(s) or modification(s) of amino acid sequence altering the binding activity of C1q of the Fc region.

In one embodiment, the 'fusion protein with low affinity for blocking the interaction between CD47 and SIRPα' is a fusion protein comprising an extracellular truncated variant of SIRPα and a binding sequence for binding the arm, wherein, the extracellular truncated variant of SIRPα and the binding sequence for binding the arm are optionally linked by an adaptor sequence, and the binding sequence for binding the arm optionally comprises an Fc region.

In one embodiment, the Fc region of the present disclosure is conceptual, i.e., although it may not be present actually, antibody engineering can be performed according to the amino acid sequence of a desired Fc region variant to produce a polypeptide or a fusion protein comprising the sequence, or a DNA encoding the amino acid sequence of the desired Fc region variant.

In one embodiment, the Fc region can be an Fc region variant. The "Fc region variant" used herein refers to an Fc region with one or more amino acid residue modification(s) on the natural amino acid sequence of Fc. Methods for these modifications are well known to those skilled in the art, include but are not limited to, site-directed mutagenesis of the DNA sequence encoding the Fc region, such as using PCR mutagenesis and cassette mutagenesis to prepare the Fc region variant. For example, one or more amino acid residue(s) of the Fc region can be deleted to increase FcR binding. For example, in one embodiment, an insertion type of Fc region variant may be prepared to alter the effector function of the Fc region.

In one embodiment, for example, at least one amino acid residue (such as 1-2 amino acid residue(s), generally no more than 10 amino acid residues) can be inserted adjacent to one or more site(s) of the Fc region identified to affect FcR binding. 'Adjacent' means within 1-2 amino acid residue(s) distant from the site of the Fc region identified to affect the binding of FcR. Such Fc region variants may exhibit increased or decreased FcR binding and/or ADCC activity. In order to prepare such insertion type of variants, a co-crystal structure of a polypeptide comprising the FcR binding region (such as the extracellular domain of the target FCR) and an Fc region to which an amino acid residue is to be inserted can be assessed, to involve an Fc region variant having, such as increased FcR binding ability. Such insertions are generally located in the loop of the Fc region.

In one embodiment, an Fc region variant which mediates antibody-dependent cell-mediated cytotoxicity (ADCC) more efficiently and/or binds to Fcγ receptor (FcγR) with a higher affinity compared to the recombinant protein comprising a natural Fc region in the presence of human effector cells, can be prepared by introducing an appropriate amino acid sequence modification to the natural Fc region. The Fc region variant of the present disclosure generally comprises at least one amino acid modification in the Fc region. Preferably, a plurality of amino acid modifications are combined. For example, the Fc region variant may comprise 2, 3, 4, 5 or more amino acid residue substitutions, such as in the identified specific FcR binding site.

The natural Fc region is preferably a human Fc region, such as the natural sequence of the Fc region of human IgG1 (A or non-A isotype), IgG2, IgG3 or IgG4.

In one embodiment, the 'high affinity tumor-targeting arm' and the 'fusion protein with low affinity for blocking the interaction between CD47 and SIRPα' are heterodimerized by knobs-into-holes. For example, the knobs-into-holes is a protruding "knobs" formed by the T366W mutation, and a hollow "holes" formed by one amino acid mutation (Y407V) or three amino acid mutations (T366S, L368A and Y407V). The mutation follows Kabat numbering scheme [Eu numbering scheme of Kabat et al. (1991)], indicating the original amino acid residue, the mutation site and the substitution amino acid residue respectively from left to right, for example, in T366W, T is the original amino acid residue, 366 is the mutation site and W is the amino acid residue for substituting T.

In one embodiment, the 'high affinity tumor-targeting arm' is a half antibody specific to a target selected from the group consisting of 5T4, AGS-16, ALK1, ANG-2, B7-H3, B7-H4, c-Met, CA6, CD123, CD19, CD20, CD22, EpCAM, CD30, CD32b, CD37, CD38, CD40, CD52, CD70, CD74, CD79b, CD98, CEA, CEACAM5, CLDN18.2, CLDN6, CS1, CXCR4, DLL-4, EGFR, EGP-1, ENPP3, EphA3, ETBR, FGFR2, FN, FR-α, GCC, GD2, GPC-3, GPNMB, HER2, HER3, HLA-DR, ICAM-1, IGF-1R, IL-3R, MSLN, MUC16, MUC1, NaPi2b, nectin-4, Notch 2, Notch 1, PD-L1, PD-L2, PDGFR-α, PS, PSMA, SLTRK6, STEAP1, TEM1, VEGFR, CD25, CD27L, DKK-1, CSF-1R, MSB0010718C, BCMA and CD138, preferably a half antibody of IgG1 antibody, optionally a human-mouse chimeric half antibody, a humanized half antibody, a fully human half antibody; more preferably a humanized or fully human half antibody of IgG1 antibody.

In one embodiment, the 'fusion protein with low affinity for blocking the interaction between CD47 and SIRPα' comprises an amino acid sequence selected from the group consisting of b1), b2), b3) and b4): b1) SEQ ID No: 26; b2) SEQ ID No: 27; b3) SEQ ID No: 28; b4) an amino acid sequence obtained by inserting, deleting, modifying and/or conservatively substituting at least one amino acid residue such as 1-5 amino acid residue(s) of any one of the amino acid sequences described above, wherein the binding affinity of homodimer thereof to a CD47 is not higher than the binding affinity of homodimer of b1), b2) or b3) to a CD47. The signal peptide region sequence, adaptor sequence, hinge region sequence, region sequence and/or binding sequence contained in the above sequences may be arbitrarily replaced according to the methods well known to those skilled in the art or with common signal peptide region sequences, adaptor sequences, hinge region sequences, Fc region sequences and/or binding sequences.

In one embodiment, the bispecific recombinant protein comprises the following sequence:

when the high affinity tumor-targeting arm targets CD20, the high affinity tumor-targeting arm comprises SEQ ID No: 16 and SEQ ID No: 17, the 'fusion protein with low affinity for blocking the interaction between CD47 and SIRPα' comprises SEQ ID No: 26, SEQ ID No: 27 or SEQ II) No: 28;

when the high affinity tumor-targeting arm targets EGFR, the high affinity tumor-targeting arm comprises SEQ ID No: 19 and SEQ ID No: 8, the 'fusion protein with low affinity for blocking the interaction between CD47 and SIRPα' comprises SEQ ID No: 26, SEQ ID No: 27 or SEQ ID No: 28;

when the high affinity tumor-targeting arm targets Her2, the high affinity tumor-targeting arm comprises SEQ ID No: 20 and SEQ ID No: 21, or SEQ ID No: 22 and SEQ ID No: 23, the 'fusion protein with low affinity for blocking the interaction between CD47 and SIRPα' comprises SEQ ID No: 26, SEQ ID No: 27 or SEQ ID No: 28; or when the high affinity tumor-targeting arm targets PD-L1, the high affinity tumor-targeting arm comprises SEQ ID No: 24 and SEQ ID No: 13, the 'fusion protein with low affinity for blocking the interaction between CD47 and SIRPα' comprises SEQ ID No: 26, SEQ D No: 27 or SEQ D No: 28.

In one aspect, the present disclosure provides a nucleic acid molecule encoding a bispecific recombinant protein. Preferably, the nucleic acid molecule encoding the 'high affinity tumor-targeting arm' and the nucleic acid molecule encoding the 'fusion protein with low affinity for blocking the interaction between CD47 and SIRPα' are presented together in a same DNA strand, or the nucleic acid molecule encoding the 'high affinity tumor-targeting arm' and the nucleic acid molecule encoding the 'fusion protein with low affinity for blocking the interaction between CD47 and SIRPα' are presented in separate DNA strands.

In another aspect, the present disclosure provides an expression vector comprising a nucleic acid molecule.

In another aspect, the present disclosure provides a cell comprising an expression vector.

In another aspect, the present disclosure provides a method for preparing a bispecific recombinant protein comprising: 1) providing a 'high affinity tumor-targeting arm'; 2) providing a 'fusion protein with low affinity for blocking the interaction between CD47 and SIRPα'; 3) contacting the 'high affinity tumor-targeting arm' and the 'fusion protein with low affinity for blocking the interaction between CD47 and SIRPα' to form the recombinant protein.

In one embodiment, a method for producing a recombinant protein comprises expressing the recombinant protein in a host cell comprising an expression vector, wherein the expression vector comprises a nucleic acid molecule encoding the recombinant protein.

In another aspect, the present disclosure also provides a method of tumor targeted therapy.

In one embodiment, the tumor is a hematological tumor or a solid tumor selected from the group consisting of breast cancer, colorectal cancer, lung cancer, pancreatic cancer, esophageal cancer, endometrial cancer, ovarian cancer, gastric cancer, prostate cancer, kidney cancer, cervical cancer, myeloma, lymphoma, leukemia, thyroid cancer, uterine cancer, bladder cancer, neuroendocrine cancer, head and neck cancer, liver cancer, nasopharyngeal carcinoma, testicular cancer, small cell lung cancer, non-small cell lung cancer, melanoma, basal cell skin cancer, squamous cell skin cancer, dermatofi-brosarcoma protuberan, merkel cell carcinoma, glioblastoma, glioma, sarcoma, mesothelioma, myelodysplastic syndrome and the like.

In another aspect, the present disclosure also provides a pharmaceutical composition comprising the recombinant protein or the fusion protein of the present disclosure, and an optional adjuvant, excipient or pharmaceutically acceptable carrier. The composition may comprise a pharmaceutically acceptable carrier. The composition may be present in any form of pharmaceutical preparation, including but not limited to, injections, powder, lyophilized powder, etc. The pharmaceutical composition in the form of the pharmaceutical preparation can be prepared according to the conventional techniques of pharmaceutics, including fusing a mixture of the pharmaceutically active ingredient such as the recombinant protein or the fusion protein of the present disclosure and a pharmaceutical carrier to form the desired dosage form according to the conventional techniques of pharmaceutics.

In one embodiment, the present disclosure also provides a pharmaceutical composition comprising an expression vector comprising a nucleic acid molecule encoding the recombinant protein or the fusion protein of the present disclosure, and an optional pharmaceutically acceptable carrier.

In another aspect, the present disclosure also provides a method for treating a tumor comprising administering to a patient or subject a therapeutically effective amount of the pharmaceutical composition of the present disclosure. The tumor expresses an additional target molecule, which includes, but is not limited to 5T4, AGS-16, ALK1, ANG-2, B7-H3, B7-H4, c-fms, c-Met, CA6, CD123, CD19, CD20, CD22, EpCAM, CD30, CD32b, CD37, CD38, CD40, CD52, CD70, CD74, CD79b, CD98, CEA, CEACAM5, CLDN18.2, CLDN6, CS1, CXCR4, DLL-4, EGFR, EGP-1, ENPP3, EphA3, ETBR, FGFR2, FN, FR-α, GCC, GD2, GPC-3, GPNMB, HER2, HER3, HLA-DR, ICAM-1, IGF-1R, IL-3R, LIV-1, MSLN, MUC16, MUC1, NaPi2b, nectin-4, Notch 2, Notch 1, PD-L1, PD-L2, PDGFR-α, PS, PSMA, SLTRK6, STEAP1, TEM1, VEGFR, CD25, CD27L, DKK-1, CSF-1R, MSB0010718C, BCMA, CD138.

In another aspect, the present disclosure also provides a method of gene therapy in vivo, comprising introducing a therapeutically effective amount of a nucleic acid molecule or a derivative thereof encoding the recombinant protein or the fusion protein of the present disclosure into a patient or subject.

In another aspect, the present disclosure also provides a method for evaluating the early immunological safety of a recombinant protein/antibody which targets CD47 and has ADCC activity in vitro, wherein the method comprises: a) providing a recombinant protein/antibody (including monovalent or multivalent) which targets and has ADCC activity; b) detecting the ADCC activity of the recombinant protein/antibody; and c) evaluating the early immunological safety of the recombinant protein/antibody (including monovalent or multivalent).

In one embodiment, the present disclosure provides a method for evaluating the early immunological safety of a recombinant protein/antibody which targets CD47 and has ADCC activity in vitro, wherein the method comprises: a) preparing an effector cell (such as human NK92MI-CD16a effector cell); b) contacting the effector cell and the recombinant protein/antibody; c) detecting the ADCC activity of the recombinant protein/antibody; and d) evaluating the early immunological safety of the recombinant protein/ antibody based on the ADCC activity.

In another embodiment, the present disclosure provides a method for evaluating the early immunological safety of a recombinant protein/antibody which targets CD47 and has ADCC activity in vitro, wherein the method comprises: a) harvesting well-growth human NK92MI-CD16a effector cells, resuspending the harvested effector cells to a cell density of $1 \times 10^5$ cells/mL to $5 \times 10^6$ cells/mL; b) incubating the recombinant protein/antibody with a gradient concentration and the effector cells prepared in step a) for 0.5-5h; c) determining the LDH activity and calculating the rate of cell lysis after the completion of incubation; and d) evaluating the early immunological safety of the recombinant protein/antibody based on the rate of cell lysis, wherein the recombinant protein/antibody with a lower rate of cell lysis rate has a higher immunological safety.

In another aspect, the present disclosure provides a method for evaluating the early immunological safety of a recombinant protein/antibody (including monovalent or multivalent) targeting CD47 in vivo, wherein the method comprises: a) providing the protein/antibody (including monovalent or multivalent) targeting CD47; b) providing a Hu-NSG mouse; c) contacting the recombinant protein/antibody and the Hu-NSG mouse; and d) evaluating the early immunological safety of the recombinant protein/antibody in the Hu-NSG mouse.

In another embodiment, the present disclosure provides a method for evaluating the early immunological safety of a recombinant protein/antibody (including monovalent or multivalent) targeting CD47 in vivo, wherein the method comprises: a) providing a Hu-NSG mouse; b) administrating the recombinant protein/antibody (including monovalent or multivalent); c) at 24-96 h after administration, taking venous blood from the mouse, lysing RBCs, incubating the remaining cells and fluorescently labeled anti-human CD45 antibody, anti-human CD19 antibody or anti-human CD3 antibody for 15-60 min, and detecting by flow cytometry; and d) evaluating the early immunological safety of the recombinant protein/antibody based on the clearance rate of cells, wherein the recombinant proteins/antibody with a lower clearance rate of cells (except the target cells) has a higher immunological safety.

The beneficial effects of the present disclosure are as follows:

The recombinant proteins of the present disclosure can achieve a higher safety (such as avoiding anemia, RBC agglutination, cytotoxicity of CD47-positive non-tumor target cells caused by anti-CD47 antibodies/recombinant proteins (such asHu5F9-G4), reducing the risk of potential safety, immunogenicity, stability and other uncertainties brought by high affinity mutants of SIRPα-Fc fusion protein, etc.) by the 'fusion protein with low affinity for blocking the interaction between CD47 and SIRPα', which reduces the binding of the recombinant proteins of the present disclosure to the CD47 on non-tumor cells (such as RBCs, NIC cells, T cells, etc.).

It has been surprisingly by the present disclosure that the binding affinity of the recombinant proteins of the present disclosure to tumor cells can be significantly enhanced by the 'high affinity tumor-targeting arm' and the 'fusion protein with low affinity for blocking the interaction between CD47 and SIRPα', thereby mediating efficient killing of the tumor cells (including but not limited to the effector function of antibodies upon specifically binding to the target antigen on the surface of tumor cells, targeted phagocytosis of macrophages).

The recombinant proteins of the present disclosure can achieve a dual targets effect by the 'high affinity tumor-targeting arm' (such as but not limited to half antibody) and the 'fusion protein with low affinity for blocking the interaction between CD47 and SIRPα', and the results of the present disclosure show that the recombinant proteins of the present disclosure exert anti-tumor effects through a variety of mechanisms with the multiple functions of the 'high affinity tumor-targeting arm' and the 'fusion protein with low affinity for blocking the interaction between CD47 and SIRPα', thereby achieving a higher efficacy.

Compared to a combination therapy of two separate targeting antibodies, the recombinant proteins of the present disclosure have the advantages such as a lower cost and more convenient use, and thus can solve the problems of low patient compliance and high cost accompanied by the combination therapy with antibodies.

The recombinant proteins of the present disclosure have a higher tissue permeability and efficacy than classical bispecific antibodies (consisted of two half antibodies), since the 'fusion protein with low affinity for blocking the interaction between CD47 and SIRPα' has a smaller molecular weight than the single arm of the classical bispecific antibodies (half antibody).

The 'fusion protein with low affinity for blocking the interaction between CD47 and SIRPα' of the present disclosure comprises different lengths of extracellular truncated variants of SIRPα, which can be quickly optimized to pair with the 'high affinity tumor-targeting arm' (such as half antibody), thereby avoiding the situation where the simultaneous binding of conventional bifunctional antibodies to the two target antigens may be affected by the spatial structure of the two target antigens (in particular, when the antibody recognition sites of the two target antigens differ greatly in the distance to the cell membrane, it is difficult to simultaneously bind to both the tumor-targeting antigen and the CD47 antigen), and providing an improved binding of the obtained recombinant proteins to tumor cells and a better killing of tumor cells.

The present disclosure provides a novel method for evaluating the safety of immunotherapeutic drugs targeting CD47 in vitro. Conventional early safety evaluation of anti-CD47 antibodies is generally performed by determining the effect of the drugs on RBC agglutination. In view of the species-specific binding of human SIRPα to human CD47, human blood must be used when evaluating whether a recombinant protein/antibody targeting CD47 has a safety problem of RBC agglutination in the human body, however, the application of human blood is restricted by ethics and the availability of genetic resources. In addition, experiments of RBC agglutination cannot be used to evaluate the early immunological safety of drugs. The present disclosure uses an optimized method for detecting ADCC activity (early in vitro immunological safety evaluation experiments), in place of the traditional human RBC agglutination experiment, to evaluate the early immunological safety of the recombinant proteins/antibodies (including monovalent or multivalent) which target CD47 and have ADCC activity. The method is simple, fast and not limited by blood resources.

The present disclosure provides a novel in vivo method for evaluating the safety of immunotherapeutic dugs targeting CD47. Pre-clinical in vivo evaluation on the immunological safety of drugs generally uses non-human primates, which requires a larger amount of the sample and thus increases the difficulty and cost of early sample preparation. There is yet no mature early immunological safety evaluation method on other species in vivo, leading to big safety risks in future clinical research and wastes in research and development investment. The present disclosure provides a Hu-NSG mouse, wherein the early safety evaluation experiment performed on the Flu-NSG can simulate the safety condition of the drug in the human immune system, reduce the preparation difficulty and cost, gain the advantages of low detection cost and high detection efficiency, and lower the risk in research and development of immune therapeutic drugs for cancer, compared to preclinical or clinical studies.

The present disclosure provides recombinant proteins, which achieves a high affinity and specific targetability to the tumor via a 'high affinity tumor-targeting arm' and the blocking of CD47-SIRPα interactions via a 'fusion protein with low affinity for blocking the interaction between CD47 and SIRPα'.

The recombinant proteins of the present disclosure overcome the technical problems of low yield and the difficulty in purifying the product accompanied with conventional bifunctional antibodies. In one embodiment of the present disclosure, for the recombinant proteins having a single-chain protein as the right arm (Fc knob mutation), when a light chain of the left arm, a heavy chain of the left arm (Fc hole mutation) and the right arm (Fc knob mutation) are all expressed in cells, more than 80% of the expressed products are the target proteins upon purification by protein A, the yield of expressed product is effectually increased. Although there are a small amount of left arm dimers, right arm dimers, left arm monomer and right arm monomer, they differ greatly from the desired product in properties such as molecular weight, charge distribution, and thus can be easily removed by conventional purification methods such as ion-exchange chromatography, hydrophobic interaction chromatography, size exclusion chromatography, affinity chromatography, salting out method (such as ammonium sulfate precipitation method), so the method of the present disclosure is suitable for industrial scale production.

The 'fusion protein with low affinity for blocking the interaction between CD47 and SIRPα' of the present disclosure and the 'high affinity tumor-targeting arm' (such as but not limited to half antibody) are generally capable of forming a recombinant protein which is capable of antagonizing the immunosuppressive effect of CD47.

The present disclosure overcomes the defects of the low pharmacological efficiency of the SIRPα-Fc fusion proteins in the prior art due to their low affinity to CD47, and avoid the adverse effects due to the high immunogenicity and high specificity for non-tumor targets of the high affinity variants of SIRPα. Meanwhile, the recombinant protein of the present disclosure has a weak binding affinity to CD47 expressed on the surface of normal cells (such as RBCs), therefore the side effects such as RBC agglutination and anemia caused by the treatment with conventional anti-CD47 antibodies can be reduced or avoided.

It should be understood by those skilled in the art that the scope of the present disclosure is not to be unduly limited due to one certain technical solution of the present disclosure which can achieve one certain express or implied beneficial effect of the present disclosure but cannot achieve or fully achieve another beneficial effect. It should be understood by those skilled in the art that any product, method, or use within the scope of the present disclosure is considered to have solved the technical problem of the present disclosure and achieved the corresponding technical effect, as long as it achieves any one of the explicit or implied beneficial effects of the present disclosure or an arbitrary combination thereof.

Specifically, the present disclosure relates to the following embodiments:

Embodiment 1: A bispecific recombinant protein, wherein the bispecific recombinant protein comprises a 'tumor-targeting arm' and a 'fusion protein for blocking the interaction between CD47 and SIRPα'.

Embodiment 2: The bispecific recombinant protein of embodiment 1, wherein the 'fusion protein for blocking the interaction between CD47 and SIRPα' comprises an extracellular truncated variant of SIRPα (including an extracellular truncated variant of human wild-type SIRPα or its variant with non-high affinity to CD47).

Embodiment 3: The bispecific recombinant protein of embodiment 2, wherein the extracellular truncated variant of SIRPα comprises a part or full of the amino acid sequence of the extracellular domain of SIRPα.

Embodiment 4: The bispecific recombinant protein of any one of embodiments 1-3, wherein a 'high affinity tumor-targeting arm' does not bind to a CD47, and the ratio of the binding affinity of the antibody corresponding to the 'high affinity tumor-targeting arm' to the target antigen on a tumor cell to the binding affinity of the homodimer of the monomer fusion protein corresponding to the 'fusion protein with low affinity for blocking the interaction between CD47 and SIRPα' to a CD47 on a tumor cell is at least 6.

Embodiment 5: The bispecific recombinant protein of any one of embodiments 1-4, wherein the extracellular truncated variant of SIRPα comprises an amino acid sequence selected from the group consisting of a1), a2), a3) and a4):
  a1) SEQ ID No: 30;
  a2) SEQ ID No: 31;
  a3) SEQ ID No: 32;
  a4) an amino acid sequence Obtained by inserting, deleting, modifying and/or conservatively substituting at least one amino acid residue such as 1-5 amino acid residue(s) of any one of the amino acid sequence described above, wherein the binding affinity of monomer thereof to a CD47 is not higher than the binding affinity of monomer of a1), a2) or a3) to a CD47.

Embodiment 6: The bispecific recombinant protein of any one of embodiments 1-5, wherein the bispecific recombinant protein has a configuration comprising a left arm and a right arm which are symmetrically arranged, wherein the 'high affinity tumor-targeting arm' is arranged in the left arm, the 'fusion protein with low affinity for blocking the interaction between CD47 and SIRPα' is arranged in the right arm.

Embodiment 7: The bispecific recombinant protein of embodiment 6, wherein the left arm is in the form of Fab or Fab' of immunoglobulin, the right arm is an extracellular truncated variant of SIRPα.

Embodiment 8: The bispecific recombinant protein of embodiment 7, wherein the length of the right arm is configured for the distance from the epitope to which the left arm binds to the membrane surface of the target cell.

Embodiment 9: The bispecific recombinant protein of embodiment 8, when the 'high affinity tumor-targeting arm' is configured for binding a membrane-proximal epitope of the target cell, the extracellular truncated variant of SIRPα is selected from the shorter amino acid sequence among a1), a2), a3) and a4).

Embodiment 10: The bispecific recombinant protein of any one of embodiments 1-9, wherein the tumor-targeting arm is specific to a target selected from the group consisting of 5T4, AGS-16, ALK1, ANG-2, B7-H3, B7-H4, c-fms, c-Met, CA6, CD123, CD19, CD20, CD22, EpCAM, CD30, CD32b, CD37, CD38, CD40, CD52, CD70, CD74, CD79b, CD98, CEA, CEACAM5, CLDN18.2, CLDN6, CS1, CXCR4, DLL-4, EGFR, EGP-1, ENPP3, EphA3, ETBR, FGFR2, FN, FR-α, GCC, GD2, GPC-3, GPNMB, HER2, HER3, HLA-DR, ICAM-1, IGF-1R, IL-3R, LIV-1, MSLN, MUC16, MUC1, NaPi2b, nectin-4, Notch 2, Notch 1, PD-L1, PD-L2, PDGFR-α, PS, PSMA, SLTRK6, STEAP1, TEM1, VEGFR, CD25, CD27L, DKK-1, CSF-1R, MSB0010718C, BCMA and CD138.

Embodiment 11: The bispecific recombinant protein of embodiment 10, wherein, when the target is CD20, EGFR or PD-L1, the extracellular truncated variant of SIRPα is a1); when the target is HER2, the extracellular truncated variant of SIRPα is a1) and a2).

Embodiment 12: The bispecific recombinant protein of any one of embodiments 1-11, wherein, the 'tumor-targeting arm' binds to the 'fusion protein blocking the interaction between CD47 and SIRP' via two or three of the following bindings: intermolecular force, covalent bond (such as interchain disulfide bond) and salt bond.

Embodiment 13: The bispecific recombinant protein of any one of embodiments 1-12, wherein, the 'tumor-targeting arm' and/or the 'fusion protein for blocking the interaction between CD47 and SIRPα' further comprise an Fc region.

Embodiment 14: The bispecific recombinant protein of embodiment 13, wherein, the Fc region comprises a natural sequence of the Fc region or an unnatural sequence of the Fc region.

Embodiment 15: The bispecific recombinant protein of embodiment 14, wherein the Fc region is human Fc region.

Embodiment 16: The bispecific recombinant protein of embodiment 15, wherein the 'high affinity tumor-targeting arm' and the 'fusion protein with low affinity for blocking the interaction between CD47 and SIRPα' are heterodimerized by knobs-into-holes.

Embodiment 17: The bispecific recombinant protein of any one of embodiments 1-16, wherein the 'tumor-targeting arm' is a half antibody specific to a target selected from the group consisting of 5T4, AGS-16, ALK1, ANG-2, B7-H3, B7-H4, c-Met, CA6, CD123, CD19, CD20, CD22, EpCAM, CD30, CD32b, CD37, CD38, CD40, CD52, CD70, CD74, CD79b, CD98, CEA; CEACAM5, CLDN18.2, CLDN6, CS1, CXCR4, DLL-4, EGFR, EGP-1, ENPP3, EphA3, ETBR, FGFR2, FN, FR-α, GCC, GD2, GPC-3, GPNMB, HER2, HER3, HLA-DR, ICAM-1, IGF-1R, IL-3R, LIV-1, MSLN, MUC16, MUC1, NaPi2b, ectin-4, Notch 2, Notch 1, PD-L1, PD-L2, PDGFR-α, PS, PSMA, SLTRK6, STEAP1, TEM1, VEGFR, CD25, CD27L, DKK-1, CSF-1R, MSB0010718C, BCMA and CD138; preferably a half antibody of IgG1 antibody, optionally a human-mouse chimeric half antibody, a humanized half antibody, a fully human half antibody; more preferably a humanized or fully human half antibody of IgG1 antibody.

Embodiment 18: The bispecific recombinant protein of any one of embodiments 1-17, wherein the 'fusion protein for blocking the interaction between CD47 and SIRPα' is a fusion protein comprising an extracellular truncated variant of SIRPα and a binding sequence for binding the arm, the extracellular truncated variant of SIRPα and the binding sequence for binding the arm are optionally linked by an adaptor sequence, the binding sequence for binding the arm optionally comprises an Fc region.

Embodiment 19: The bispecific recombinant protein of any one of embodiments 1-18, wherein the 'fusion protein for blocking the interaction between CD47 and SIRPα' comprises an amino acid sequence selected from the group consisting of b1), b2), b3) and b4):
b1) SEQ ID No: 26;
b2) SEQ ID No: 27;
b3) SEQ ID No: 28;
b4) an amino acid sequence obtained by inserting, deleting, modifying and/or conservatively substituting at least one amino acid residue such as 1-5 amino acid residue(s) of any one of the amino acid sequence described above, wherein the binding affinity of homodimer thereof to a CD47 is not higher than the binding affinity of homodimer of b1), b2) or b3) to a CD47.

Embodiment 20: The bispecific recombinant protein of embodiment 19, wherein, when the 'high affinity tumor-targeting arm' targets CD20, then the 'high affinity tumor-targeting arm' comprises SEQ ID No: 16 and SEQ ID No: 17, the 'low affinity fusion protein for blocking the interaction between CD47 and SIRPα' comprises SEQ ID No: 26; when the 'high affinity tumor-targeting arm' targets EGFR, then the 'high affinity tumor-targeting arm' comprises SEQ ID No: 19 and SEQ ID No: 8, the 'fusion protein with low affinity for blocking the interaction between CD47 and SIRPα' comprises SEQ ID No: 26, SEQ ID No: 27 or SEQ ID No: 28; when the 'high affinity tumor-targeting arm' targets Her2, then the 'high affinity tumor-targeting arm' comprises SEQ ID No: 20 and SEQ ID No: 21, or SEQ ID No: 22 and SEQ ID No: 23, the 'fusion protein with low affinity for blocking the interaction between CD47 and SIRPα' comprises SEQ ID No: 26 or SEQ ID No: 27; or, when the 'high affinity tumor-targeting arm' targets PD-L1, then the 'high affinity tumor-targeting arm' comprises SEQ ID No: 24 and SEQ ID No: 13, and the 'fusion protein with low affinity for blocking the interaction between CD47 and SIRPα' comprises SEQ ID No: 26.

Embodiment 21: A nucleic acid molecule encoding the bispecific recombinant protein of any one of embodiments 1-20.

Embodiment 22: The nucleic acid molecule of embodiment 21, wherein the nucleic acid molecule encoding the 'high affinity tumor-targeting arm' and the nucleic acid molecule encoding the 'fusion protein with low affinity for blocking the interaction between CD47 and SIRPα' are presented in a same DNA strand, or presented in separate DNA strands.

Embodiment 23: An expression vector comprising the nucleic acid molecule of embodiment 21 or 22.

Embodiment 24: A cell comprising the expression vector of embodiment 23.

Embodiment 25: A method for preparing the bispecific recombinant protein comprising:
1) providing a 'tumor-targeting arm';
2) providing a 'fusion protein for blocking the interaction between CD47 and SIRPα';
3) contacting the 'tumor-targeting arm' and the 'fusion protein for blocking the interaction between CD47 and SIRPα' to form the recombinant protein.

Embodiment 26: The method of embodiment 25, wherein expressing the recombinant protein in the cell of embodiment 24.

Embodiment 27: The method of embodiment 25, wherein the contacting comprises binding via two or three of the following bindings: intermolecular force, covalent bond (such as interchain disulfide bond) and salt bond.

Embodiment 28: The method of any one of embodiments 25-27, wherein the contacting comprises binding via knobs-into-holes technique.

Embodiment 29: A fusion protein, wherein the fusion protein comprises an extracellular truncated variant of SIRPα and a binding sequence for binding another polypeptide.

Embodiment 30: The fusion protein of embodiment 29, wherein the binding sequence for binding another polypeptide optionally is an Fc region; optionally, the Fc region comprises holes mutation(s) and/or knobs mutation(s).

Embodiment 31: The fusion protein of embodiment 29 or 30, wherein the extracellular truncated variant of SIRPα comprises a part or full of the amino acid sequence of the extracellular domain of human wild-type SIRPα or its high affinity variant.

Embodiment 32: The fusion protein of embodiment 31, wherein the extracellular truncated variant of SIRPα comprises an amino acid sequence selected from the group consisting of a1), a2), a3) and a4):
 a1) SEQ ID No: 30;
 a2) SEQ ID No: 31;
 a3) SEQ ID No: 32;
 a4) an amino acid sequence Obtained by inserting, deleting, modifying and/or conservatively substituting at least one amino acid residue such as 1-5 amino acid residue(s) of any one of the amino acid sequence described above, wherein the binding affinity of monomer thereof to a CD47 is not higher than the binding affinity of monomer of a1), a2) or a3) to a CD47.

Embodiment 33: The fusion protein of any one of embodiments 29-31, wherein the fusion protein is selected from the group consisting of b1), b2), b3) and b4):
 b1) SEQ ID No: 26;
 b2) SEQ ID No: 27;
 b3) SEQ ID No: 28;
 b4) an amino acid sequence obtained by inserting, deleting, modifying and/or conservatively substituting at least one amino acid residue such as 1-5 amino acid residue(s) of any one of the amino acid sequence described above, wherein the binding affinity of homodimer thereof to a CD47 is not higher than the binding affinity of homodimer of b1), b2) or b3) to a CD47.

Embodiment 34: A nucleic acid molecule encoding the bispecific recombinant protein of any one of embodiments 29-33.

Embodiment 35: An expression vector comprising the nucleic acid molecule of embodiment 34.

Embodiment 36: A cell comprising the expression vector of embodiment 35.

Embodiment 37: A method for preparing the bispecific recombinant protein of any one of embodiments 29-33, wherein the method comprises:
 1) providing an extracellular truncated variant of SIRPα;
 2) providing a binding sequence for binding another polypeptide;
 3) contacting the extracellular truncated variant of SIRPα and the binding sequence for binding another polypeptide to form the bispecific recombinant protein.

Embodiment 38: A method for preparing the bispecific recombinant protein of any one of embodiments 29-33, wherein the method comprises expressing the bispecific recombinant protein in the cell of embodiment 32.

Embodiment 39: A pharmaceutical composition comprising the recombinant protein of any one of embodiments 1-20 or the fusion protein of any one of embodiments 29-33, and an optional adjuvant, excipient or pharmaceutically acceptable carrier.

Embodiment 40: The pharmaceutical composition of embodiment 39, which is in the form of injection or lyophilized powder.

Embodiment 41: A pharmaceutical composition comprising a nucleic acid molecule encoding the recombinant protein of any one of embodiments 1-20 or the fusion protein of any one of embodiments 29-33, and an optional pharmaceutically acceptable carrier.

Embodiment 42: A use of the fusion protein of any one of embodiments 29-33 in preparing the recombinant protein of any one of embodiments 1-20.

Embodiment 43: A use of the recombinant protein of any one of embodiments 1-20 or the fusion protein of any one of embodiments 29-33 in manufacturing a medicament for treating a tumor.

Embodiment 44: The use of embodiment 43, wherein the tumor is a hematological tumor or a solid tumor selected from the group consisting of breast cancer, colorectal cancer, lung cancer, pancreatic cancer, esophageal cancer, endometrial cancer, ovarian cancer, gastric cancer, prostate cancer, kidney cancer, cervical cancer, myeloma, lymphoma, leukemia, thyroid cancer, uterine cancer, bladder cancer, neuroendocrine cancer, head and neck cancer, liver cancer, nasopharyngeal carcinoma, testicular cancer, small cell lung cancer, non-small cell lung cancer, melanoma, basal cell skin cancer, squamous cell skin cancer, dermatofi-brosarcoma protuberan, merkel cell carcinoma, glioblastoma, glioma, sarcoma, mesothelioma, myelodysplastic syndrome and the like.

Embodiment 45: A use of the recombinant protein of any one of embodiments 1-20 or the fusion protein of any one of embodiments 29-33 in manufacturing a medicament for in vivo gene therapy.

Embodiment 46: A method for evaluating the early immunological safety of a recombinant protein/antibody which targets CD47 and has ADCC activity in vitro, wherein the method comprises:
 a) providing a recombinant protein/antibody (including monovalent or multivalent) which targets and has ADCC activity;
 b) detecting the ADCC activity of the recombinant protein/antibody; and
 c) evaluating the early immunological safety of the recombinant protein/antibody.

Embodiment 47: A method for evaluating the early immunological safety of a recombinant protein/antibody which targets CD47 and has ADCC activity in vitro, wherein the method comprises:
 a) preparing an effector cell, for example, it not limited to human NK92MI-D16a effector cell;
 b) contacting the effector cell and the recombinant protein/antibody;
 c) detecting the ADCC activity of the recombinant protein/antibody; and
 d) evaluating the early immunological safety of the recombinant protein/antibody based on the ADCC activity.

Embodiment 48: The method of embodiment 47, comprising:
 a) harvesting well-grown human NK92MI-CD16a effector cells, resuspending the harvested effector cells to a cell density of $1\times10^5$ cells/mL to $5\times10^6$ cells/mL;
 b) incubating the recombinant protein/antibody with a gradient concentration and the effector cells prepared in step a) for 0.5-5 h;
 c) determining the activity and calculating the rate of cell lysis after the completion of incubation; and
 d) evaluating the early immunological safety of the recombinant protein/antibody based on the rate of cell lysis, wherein the recombinant protein/antibody with a lower rate of cell lysis has a higher immunological safety.

Embodiment 49: A method for evaluating the early immunological safety of a recombinant protein/antibody (including monovalent or multivalent) targeting CD47 in vivo, wherein the method comprises:
 a) providing the protein/antibody (including monovalent or multivalent) targeting CD47;
 b) providing a Hu-NSG mouse;

c) contacting the recombinant protein/antibody and the Hu-NSG mouse; and d) evaluating the early immunological safety of the recombinant protein/antibody in the Hu-NSG mouse.

Embodiment 50: A method for evaluating the early immunological safety of a recombinant protein/antibody (including monovalent or multivalent) targeting CD47 in vivo, wherein the method comprises:

a) providing a Hu-NSG mouse;

b) administrating the recombinant protein/antibody (including monovalent or multivalent);

c) at 24-96 h after administration, taking venous blood from the mouse, lysing the RBCs, incubating the remaining cells and fluorescently labeled anti-human CD45 antibody, anti-human CD19 antibody or anti-human CD3 antibody for 15-60 min, and detecting by flow cytometry; and d) evaluating the early immunological safety of the recombinant protein/antibody based on the clearance rate of cells, wherein the recombinant proteins/antibody with a lower clearance rate of cells (except the target cells) has a higher immunological safety.

BRIEF DESCRIPTION OF THE DRAWINGS

FIG. 7 shows the flow cytometry results of the binding affinity of the recombinant proteins of the present disclosure to the target corresponding to the left arm. Hu5F9-G4, Ofa-Fc1-D1-Fc2 and SIRPα D1-Fc refer to the average fluorescence intensity after the binding of the samples Hu5F9-G4, Ofa-Fc1-D1-Fc2 and SIRPα D1-Fc to the Raji cells which are not blocked by anti-CD47 antibody Hu5F9-G4(Fab)2, Hu5F9-G4 (b), Ofa-Fc1-D1-Fc2(b) and SIRPα D1-Fc(b) refer to the average fluorescence intensity after the binding of Hu5F9-G4, Ofa-Fc1-D1-Fc2 and SIRPα D1-Fc to Raji cells which are blocked with anti-CD47 antibody Hu5F9-G4(Fab)2.

FIG. 8A corresponds to Raji cells (CD20+CD47); FIG. 8B corresponds to SKBR-3 cells (Her2+CD47); FIG. 8C corresponds to A431 cells (EGFR+CD47); FIG. 8D corresponds to NCI-H441 cells (PD-L1+CD47).

FIG. 13B corresponds to Hu5F9-G4 (6.7 µg/mouse); FIG. 13C corresponds to Ofa-Fc1-D1-Fc2 (5 µg/mouse).

FIG. 14A-D correspond to Ofa-Fc1-D1-Fc2 (1 µg/mouse), wherein FIGS. 14A and 14B show the detection results before administration, and FIGS. 14C and 14D show the detection results at 72 hours after administration. FIG. 14E-H correspond to Ofa-Fc1-DP1$^m$-Fc2 (1 µg/mouse), wherein FIG. 14E and FIG. 14F show the detection results before administration, FIG. 14G and FIG. 14H show the detection results at 72 hours after administration.

FIG. 15A-B show the results at 96 hours after administration, wherein Fig. A corresponds to Hu5F9-G4 (200 µg/mouse) and FIG. 15B corresponds to Ofa-Fc1-D1-Fc2 at a high dose (150 µg/mouse). FIG. 15C-D show the results at 14 days after administration, wherein FIG. 15C corresponds to Hu5F9-G4 (200 µg/mouse) and FIG. 15D corresponds to Ofa-Fc1-D1-Fc2 at a high dose (150 µg/mouse).

FIG. 16A shows the detection results of Anti-Her2(T)-Fc1-D1-Fc2 and Anti-Her2(T)-Fc1-D1-D2-Fc2; and FIG. 16B shows the detection results of Anti-Her2(P)-Fc1-D1-Fc2 and Anti-Her2(P)-Fc1-D1-D2-Fc2.

FIG. 17A-E show the amino acid sequences and DNA sequences corresponding to the exemplary proteins of the present disclosure.

DETAILED DESCRIPTION OF THE PREFERRED EMBODIMENT

Figure 1:
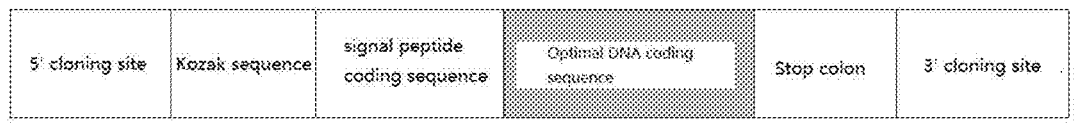
FIG. 1 shows the structure of the insert of the present disclosure to be inserted into the expression vector.

In order to promote an understanding of the present disclosure, the present disclosure will be illustrated with reference to certain examples and some specific terms described below. However, it should be understood that these specific examples are not intended to limit the scope of the present disclosure, any alterations and further modifications to the described examples, as well as any further applications of the disclosure, will all be obvious to those skilled in the art.

Recombinant Protein

As used herein, the term "recombinant protein" refers to a protein that is artificially engineered/constructed, rather than a naturally occurring protein. "Recombinant" contained in the term "recombinant protein" of the present disclosure does not denote a mode of production, and is merely used to indicate that "recombinant protein" does not naturally occur. The recombinant protein of the present disclosure may be an expressed protein and may be an assembled protein.

Optionally, the bispecific recombinant protein of the present disclosure comprises a 'high affinity tumor-targeting arm' and a 'fusion protein with low affinity for blocking the interaction between CD47 and SIRPα'.

As used herein, "high affinity tumor-targeting" refers to that the binding affinity of the recombinant protein of the present disclosure to a tumor is higher than or substantially equivalent to the binding affinity of tumor-binding antibody drugs in the prior art to the tumor, wherein the binding affinity of tumor-binding antibody drugs in the prior art to the tumor generally has anEC50 at nM or pM level. Preferably, the ratio of the binding affinity of the antibody corresponding to the 'high affinity tumor-targeting arm' to the target antigen on a tumor cell to the binding affinity of the homodimer of the monomer fusion protein corresponding to the 'fusion protein with low affinity for blocking the interaction between CD47 and SIRPα' to CD47 on a tumor cell is at least 6, optionally 6, 7, 8, 9, 10, 11, 12, 13, 14, 15 or more, or any value between them. Optionally, in the recombinant protein of the present disclosure, the ratio of the binding affinity of the antibody corresponding to the 'high affinity tumor-targeting arm' to the target antigen on a tumor cell to the binding affinity of the homodimer of SIRPa-Fc corresponding to the 'fusion protein with low affinity for blocking the interaction between CD47 and SIRPα' to CD47 on a tumor cell is at least 6, optionally 6, 7, 8, 9, 10, 11, 12, 13, 14, 15 or more, or any value between them.

As used herein, "low affinity for blocking the interaction between CD47 and SIRPα" refers to that the recombinant protein of the present disclosure is capable of blocking the interaction between CD47 and SIRPα with a low affinity. Preferably, the binding affinity of the 'fusion protein with low affinity for blocking the interaction between CD47 and SIRPα' to CD47 is not higher than the binding affinity of 'the homodimer of a monomer fusion protein comprising an extracellular truncated valiant of SIRPα' to CD47. More preferably, the binding affinity of which is not higher than the binding affinity of humanized SIRPα-Fc fusion protein to CD47.

The bispecific recombinant protein described herein can significantly enhance the tumor-targeting saturation binding abundance of a recombinant protein with an effect of modulating the function of macrophages and reduce non-tumor target side effects, as long as the ratio of the binding affinity of the antibody corresponding to the 'high affinity tumor-targeting arm' to the target antigen on tumor cell to the binding affinity of the homodimer of the monomer fusion protein corresponding to the 'fusion protein with low affinity for blocking the interaction between CD47 and SIRPα to CD47' on tumor cell is at least 6.

The method for detecting the binding affinity used herein is well known to those skilled in the art, including but is not limited to, ELISA and/or flow cytometry.

Optionally, the fusion protein of a extracellular truncated variant of signal regulatory protein alpha α (including a wild-type truncated variant and its non-high affinity variant) and a Fc described in the present disclosure and a half antibody can form a heterodimer by modifying the heavy chain of antibody, specifically, can be heterodimerized by Knobs-into-holes and/or mediated by interchain disulfide bond and/or salt bond to forma recombinant protein.

Figure 3:
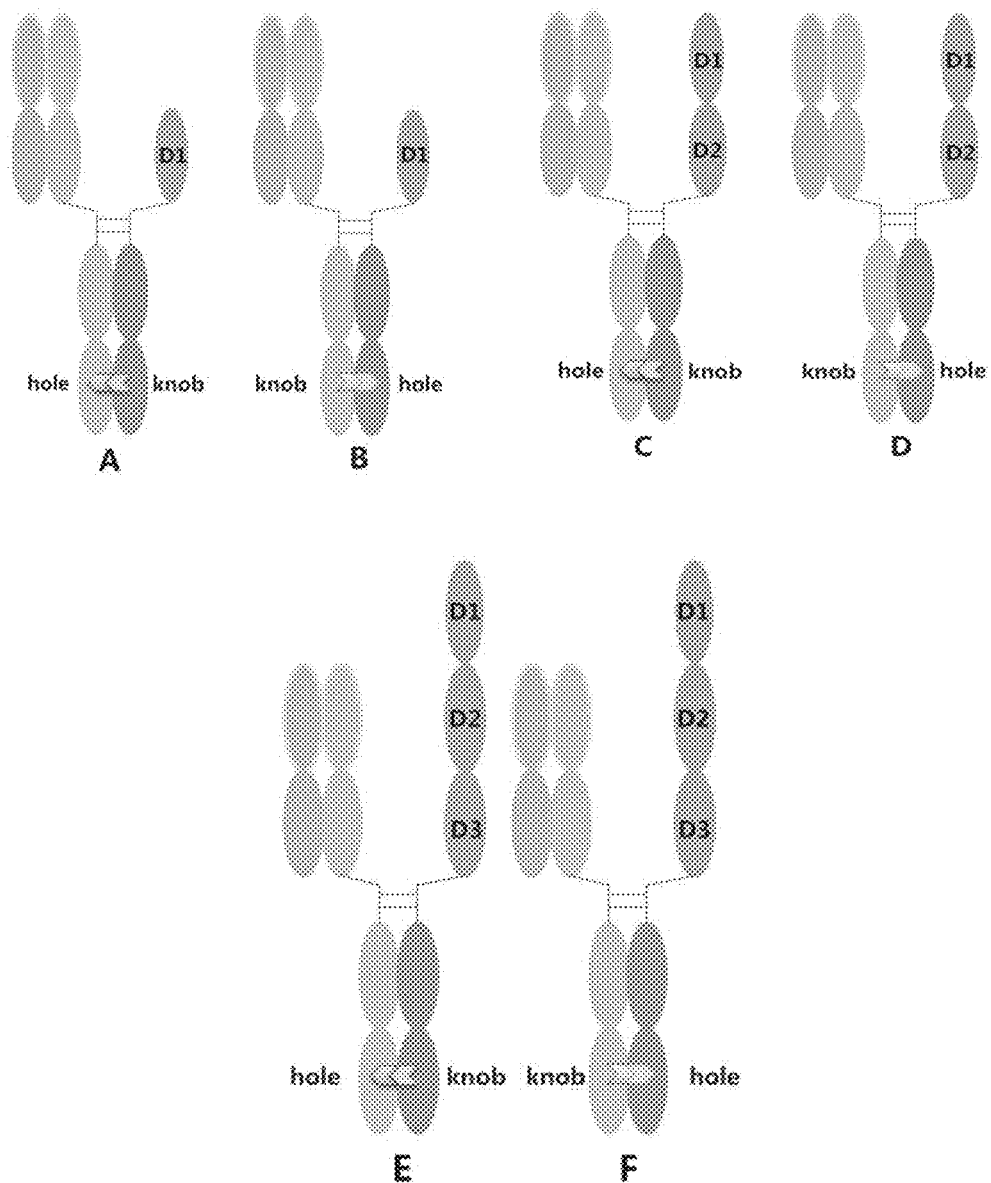
FIG. 3 shows the structure of an exemplary embodiment of the recombinant proteins of the present disclosure.

Optionally, when "tumor-targeting arm" or "half antibody" or "left arm" or "half antibody structure" or "Ig molecular monomer" and "CD47-targeting arm" or "right arm" or "fusion protein of a truncated variant of signal regulatory protein a and Fc" or "SIRPα-Fc" are heterodimerized by knobs-into-holes to forma recombinant protein, the structure of the obtained recombinant protein is as shown in FIG. 3. Wherein, the left arm is a tumor-targeting half antibody, including but is not limited to anti-5T4 half antibody, anti-AGS-16 half antibody, anti-ALK1 half antibody, anti-ANG-2 half antibody, anti-B7-H3 half antibody, anti-B7-H4 half antibody, anti-c-fms half antibody, anti-c-Met half antibody, anti-CA6 half antibody, anti-CD123 half antibody, anti-CD19 half antibody, anti-CD20 half antibody, anti-CD22 half antibody, anti-EpCAM half antibody, anti-CD30 half antibody, anti-CD32b half antibody, anti-CD37 half antibody, anti-CD38 half antibody, anti-CD40 half antibody, anti-CD52 half antibody, anti-CD70 half antibody, anti-CD74 half antibody, anti-CD79b half antibody, anti-CD98 half antibody, anti-CEA half antibody, anti-CEACAM5 half antibody, anti-CEDN18.2 half antibody, anti-CLDN6 half antibody, anti-CS1 half antibody, anti-CXCR4 half antibody, anti-DLL-4 half antibody, anti-EGFR half antibody, anti-EGP-1 half antibody, anti-ENPP3 half antibody, anti-EphA3 half antibody, anti-ETBR half antibody, anti-FGER2 half antibody, anti-EN half antibody, anti-FR-α half antibody, anti-GCC half antibody, anti-GD2 half antibody, anti-GPC-3 half antibody, anti-GPNMB half antibody, anti-HER2 half antibody, anti-HER3 half antibody, anti-HLA-DR half antibody, anti-ICAM-1 half antibody, anti-IGF-1R half antibody, anti-IL-3R half antibody, anti-LIV-1 half antibody, anti-MSLN half antibody, anti-MUC16 half antibody, anti-MUC1 half antibody, anti-NaPi2b half antibody, anti-nectin-4 half antibody, anti-Notch 2 half antibody, anti-Notch 1 half antibody, anti-PD-L1 half antibody, anti-PD-L2 half antibody, anti-PDGFR-α half antibody, anti-PS half antibody, anti-PSMA half antibody, anti-SLTRK6 half antibody, anti-STEAP1 half antibody, anti-TEM1 half antibody, anti-VEGFR half antibody, anti-CD25 half antibody, anti-CD27L half antibody, anti-DKK-1 half antibody, anti-CSF-1R half antibody, anti-MSB0010718C half antibody, anti-BCMA half antibody, anti-CD138 half antibody. The right arm is a fusion protein formed by linking an extracellular truncated variant of SIRPα (including human wild-type SIRPα and its non-high affinity mutant) and hinge region and Fc region of IgG antibody. Wherein the Fc region of the right arm is a hole mutant, the corresponding Fc region of the left arm is a knob mutant; or the right arm is a knob mutant, the corresponding Fc region of the left arm is a hole mutant. As known to those skilled in the art, the Fc region can also contain multiple mutations of holes and/or knobs simultaneously.

Table 1 shows the configuration of exemplary recombinant protein molecules.

TABLE 1

Exemplary recombinant protein molecules

| No. | Left arm | Right arm |
|---|---|---|
| 1 | Anti-CD20-Fc | D1-Fc2 |
| 2 | Anti-CD20-Fc1 | D1-D2-Fc2 |
| 3 | Anti-CD20-Fc1 | D1-D2-D3-Fc2 |
| 4 | Anti-CD20-Fc1 | D1$^m$-Fc2 |
| 5 | Anti-CD20-Fc1 | D1$^m$-D2-Fc2 |
| 6 | Anti-PD-L1-Fc1 | D1-Fc2 |
| 7 | Anti-PD-L1-Fc1 | D1-D2-Fc2 |
| 8 | Anti-PD-L1-Fc1 | D1-D2-D3-Fc2 |
| 9 | Anti-PD-L1-Fc1 | D1$^m$-Fc2 |
| 10 | Anti-PD-L1-Fc1 | D1$^m$-D2-Fc2 |
| 11 | Anti-EGFR-Fc1 | D1-Fc2 |
| 12 | Anti-EGFR-Fc1 | D1-D2-Fc2 |
| 13 | Anti-EGFR-Fc1 | D1-D2-D3-Fc2 |
| 14 | Anti-EGFR-Fc1 | D1$^m$-Fc2 |
| 15 | Anti-EGFR-Fc1 | D1$^m$-D2-Fc2 |
| 16 | Anti-Her2-Fc1 | D1-Fc2 |
| 17 | Anti-Her2-Fc1 | D1-D2-Fc2 |
| 18 | Anti-Her2-Fc1 | D1-D2-D3-Fc2 |
| 19 | Anti-Her2-Fc1 | D1$^m$-Fc2 |
| 20 | Anti-Her2-Fc1 | D1$^m$-D2-Fc2 |

Notes:
D1$^m$ represents a high affinity mutant of SIRPα extracellular truncated variant D1; D1 represents the extracellular D1 domain of human wild-type SIRPα or its non-high affinity mutant; Fc represents a wild-type Fc region; Fc1 represents an Fc region having a hole or holes mutation, Fc2 represents an Fc region having a knob or knobs mutation.

The corresponding amino acid sequence and DNA sequence of the recombinant proteins of the present disclosure are shown in FIG. 17A-E and the sequence listing file of the present disclosure.

Antibody

As used herein, the term "antibody" or "immunoglobulin" is a heterotetrameric glycoprotein of about 150,000 Daltons having a same structural feature, composing of two identical light chains (L) and two identical heavy chains (H). Each light chain is linked to a heavy chain by covalent disulfide bond(s), while the number of interchain disulfide bonds of the heavy chains varies between different immunoglobulin isotypes. Each heavy and light chain also has regularly spaced intrachain disulfide bonds. Each heavy chain has, at one end, a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains.

Tumor-Targeting Arm

As used herein, the term "tumor-targeting arm" or "half antibody" or "left arm" or "half antibody structure" or "Ig molecule monomer" refers to a heterodimeric glycoprotein composed of a light chain (L) and a heavy chain (H) of the antibody, which is the basic structure of the immunoglobulin molecule, and these terms can be used interchangeably herein. Its molecular weight is half of the molecular weight of the corresponding antibody, about 75,000 Daltons, wherein the light chain is linked to the heavy chain by a covalent disulfide bond. The heavy and light chain also has regularly spaced intrachain disulfide bonds. Each heavy chain has, at one end, a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains.

As used herein, the term "tumor-targeting arm", "half antibody" or "left arm" or "half antibody structure" or "Ig molecular monomer" may be an IgG protein targeting various tumors. The target molecules include, but are not limited to 5T4, AGS-16, ALK1, ANG-2, B7-H3, B7-H4, c-fms, c-Met, CA6, CD123, CD19, CD20, CD22, EpCAM, CD30, CD32b, CD37, CD38, CD40, CD52, CD70, CD74, CD79b, CD98, CEA, CEACAM5, CLDN18.2, CLDN6, CS1, CXCR4, DLL-4, EGFR, EGP-1, ENPP3, EphA3, ETBR, FGFR2, FN, FR-α, GCC, GD2, GPC-3, GPNMB, HER2, HER3, HLA-DR, ICAM-1, IGF-1R, IL-3R, LW-1, MSLN, MUC16, MUC1, NaPi2b, nectin-4, Notch 2, Notch 1, PD-L1, PD-L2, PDGFR-α, PS, PSMA, SLTRK6, STEAP1, TEM1, VEGFR, CD25, CD27L, DKK-1, CSF-1R, MSB0010718C, BCMA and CD138.

The Fc sequence of "tumor-targeting arm", "half antibody" or "left arm" or "half antibody structure" or "Ig molecular monomer" can employ a hole or holes mutant and/or a knob or knobs mutant.

CD47-Targeting Arm

As used herein, the term "CD47-targeting arm" or "right arm" or "fusion protein of a truncated variant of signal regulatory protein α and Fc" or "SIRPα-Fc" or 'fusion protein for blocking the interaction between CD47 and SIRPα' can be used interchangeably herein. As known to those skilled in the art, the "CD47-targeting arm" or "right arm" or "fusion protein of a truncated variant of signal regulatory protein a and Fc" or "SIRPα-Fc" or "fusion protein blocking the interaction between CD47 and SIRPα" has a variable molecular length. Optionally, the "CD47-targeting arm" or "right arm" or "fusion protein of a truncation of signal regulatory protein α and Fc" or "SIRPα-Fc" or "fusion protein blocking the interaction between CD47 and SIRPα" with a plurality of different molecular lengths can be formed by linking an extracellular truncated variant of SIRPα (including a human wild type SIRPα and its non-high affinity mutant) to the hinge region and Fc region of the IgG1 antibody. The IgG1 can be human IgG1.

The Fc of the "CD47-targeting arm" or "right arm" or "fusion protein of a truncation of signal regulatory protein α and Fc" or "SIRPα-Fc" or "fusion protein for blocking the interaction between CD47 and SIRPα" can employ a hole or holes mutant and/or a knob or knobs mutant.

As known to those skilled in the art, "tumor-targeting arm" or "half antibody" or "left arm" or "half antibody structure" or "Ig molecular monomer" and "CD47-targeting arm" or "right arm" or "signal regulatory protein atruncated variant-Fc fusion protein" or "SIRPα-Fc" or "fusion protein for blocking the interaction between CD47 and SIRPα" can form a heterodimeric recombinant protein by modifying the Fc fragment (region). Specifically, the recombinant proteins of the present disclosure can be obtained via two or three of the following bindings: intermolecular force, covalent bond (such as interchain disulfide bond) and salt bond. Optionally, the recombinant proteins of the present disclosure are obtained by the knobs-into-holes technique.

Knobs-into-Holes Technique

As used herein, the term "knobs-into-holes technology" or "knobs-into-holes" is using genetic engineering techniques to induce different mutations in two CH3 domains of the heavy chain, thereby promoting the heteroditnerization of the heavy chain. In this technology, a knob is made on one heavy chain and a hole is made on the other heavy chain, then the two heavy chains preferentially couple together to form an asymmetric antibody (Ridgway J B, et al. 'Knobs-into-holes' engineering of antibody CH3 domains for heavy chain heterodimerization. *Protein Engineering*, 1996, 9(7): 617-621). As known to those skilled in the art, a plurality of knobs and/or holes can be made on one heavy chain, and correspondingly, a plurality of holes and/or holes can also be made on the other heavy chain.

SIRPα

As used herein, the term "SIRPα" is signal regulatory protein α, also known as CD172a. Signal regulatory protein (SIRP) is a transmembrane glycoprotein including three family members, SIRPα (CD172a), SIRPβ (CD172b) and SIRPγ (CD172g). These three members have similar extramembranous region and different intramembranous region. The extramembranous region contains three immunoglobulin (Ig)-like regions, of which the first region belongs to Isk/region and the second and third regions belong to IgC region. The intramembranous region of SIRPα (CD172a) contains two inhibitory signal domains that transmit an inhibitory signal and inhibit the corresponding function of the cell. The intramembranous region of SIRPβ (CD172b) and SIRPγ (CD172g) is short and has no signal transduction region, but SIRPβ (CD172b) can transmit an activation signal via an adaptor protein (such asDAP12). SIRP proteins are mainly expressed in macrophages (Mφ), dendritic cells (DC) and neuronal cells. It specifically refers to human wild type SIRPα and its mutant with non-high affinity to CD47.

Extracellular Truncated Variant of SIRPα

"Extracellular truncated variant" is used in relation to a protein that has a transmembrane function. As used herein, "extracellular truncated variant of SIRPα" refers to a part or full of the amino acid sequence of the extrarnembranous region of human wild type SIRPα and its mutant with non-high affinity to CD47 that was selectively truncated.

As used herein, the terms "D1", "D2" and "D3" refer to the three Ig-like extracellular domains of SIRPα, which are successively D1 domain (Ig variable region-like domain, IgV region), D2 domain (Ig constant region-like domain, IgC region) and D3 domain (Ig constant region-like domain, IgC region) starting from N-terminus of the protein (Lee W Y, et al. The Role of cis Dimerization of Signal Regulatory Protein α (SIRPα) in Binding to CD47. *J Biol Chem,* 2010, 285 (49): 37953-37963).

SIRPα-Fc Fusion Protein

As used herein, the term "SIRPα-Fc fusion protein" refers to a fusion protein comprising an extracellular truncated variant of SIRPα, an adaptor sequence and an Fc region. The adaptor sequence and/or Fc region contained in the above sequences can be arbitrarily replaced according to the methods well known to those skilled in the art or with common adaptor sequences and/or Fc regions.

In order to avoid the influence of glycosylation, the present disclosure mutates asparagine to alanine on D1 (Reference: Lee W Y, et al, Novel Structural Determinants on SIRPα, that Mediate Binding to CD47. *Journal of Immunology,* 2007, 179(11): 7741-7750).

D1, D2 and D3 of the present disclosure also include corresponding adaptor sequence.

Adaptor Sequence

As used herein, the term "adaptor sequence" refers to an amino acid sequence linking an extracellular truncated variant of SIRPα and a binding sequence, optionally, the adaptor sequence is a hinge region of IgG antibody, optionally optionally comprising a hinge region and a heavy chain CH1 domain of IgG. The adaptor sequence or hinge region sequence contained in the above sequences may be arbitrarily replaced according to the methods well known to those skilled in the art or with common adaptor sequences or hinge region sequences.

Binding Sequence

As used herein, the term "binding sequence" refers to a sequence that binds a 'high affinity tumor-targeting arm' to a 'fusion protein with low affinity for blocking the interaction between CD47 and SIRPα', optionally, the binding sequence comprises a hinge region and an Fc region; more optionally, the Fc region comprises a knob or knobs mutation(s) and/or a hole or holes mutation(s). The binding sequence, hinge region sequence or Fc region sequence contained in the above sequences may be arbitrarily replaced according to the methods well known to those skilled in the art or with common binding sequences, hinge region sequences or Fc region sequences.

CD47

CD47 is a transmembrane glycoprotein belonging to the immunoglobulin superfamily and is expressed on the cell surface of almost all cells including RBCs. Ligands for CD47 include integrin, throinbospondin-1 and signal regulatory protein (SIRP). CD47 has a variety of biological functions, including cell migration, T cell activation, dendritic cell activation, axonal development, and the like. In addition, CD47 can inhibit phagocytosis of macrophages by interacting with SIRPα. In this way, CD47 transmits a so-called "don't eat me" signal that protects normal cells such as RBCs, B cells, and T cells from being phagocytosed by macrophages.

Ofa

As used herein, the terms "Ofa", "Ofatumumab" and "Anti-CD20 (Ofatumumab)" are used interchangeably herein and refer to the anti-CD20 antibody Ofatumumab.

Obi

As used herein, the terms "Obi", "Obinutuzumab" and "Anti-CD20 (Obinutuzumab)" are used interchangeably herein and refer to the anti-CD20 antibody Obinutuzumab.

Hu5F9-G4

As used herein, the terms "Anti-CD47 mAb", "anti-CD47 antibody" and "Hu5F9-G4" are used interchangeably herein and refer to the anti-CD47 antibody Hu5F9-G4.

Anti-EGFR mAb

As used herein, the terms "Anti-EGFR mAb" and "JMT101" are used interchangeably herein and refer to the anti-EGFR antibody JMT101. JMT101 is a humanized anti-EGFR monoclonal antibody, see BA03 of the patent ZL201210406288.3.

Trastuzumab

As used herein, the terms "trastuzumab", "Trastuzumab", "Anti-Her2(T) mAb" and "Herceptin" are used interchangeably herein and refer to the anti-Her2 antibody Trastuzumab.

Pertuzumab

As used herein, the terms "patezumab", "Pertuzumab", "Anti-Her2(P) mAb" and "Perjeta" are used interchangeably herein and refer to the anti-Her2 antibody Pertuzumab.

Atezolizumab

As used herein, the terms "Tecentriq" and "Atezolizumab" are used interchangeably herein and refer to the anti-PD-L1 antibody Atezolizumab.

SIRPα D1-Fc

As used herein, the terms "SIRPα D1-Fc" and "D1-Fc" are used interchangeably herein and refer to a dimer of the single-chain fusion protein SIRPα, D1-Fc.

Ofa-Fc1

Ofa-Fc1 refers to Ofatumumab half antibody having an Fc region with a hole mutation.

Anti-Her2(T)-Fc1

Anti-Her2(T)-Fc1 refers to Transtuzumab half antibody having an Fc region with a hole mutation.

Anti-Her2(P)-Fc1

Anti-Her2(P)-Fc1 refers to Pertuzumab half antibody having an Fc region with a hole mutation.

Anti-EGFR-Fc1

Anti-EGFR-Fc1 refers to anti-EGFR half antibody having an Fc region with a hole mutation.

D1-Fc2

D1-Fc2 refers to a fusion protein comprising D1 domain truncated from the extracellular domain of SIRPα and an Fc region having a knob mutation.

D1-D2-Fc2

D1-D2-Fc2 refers to a fusion protein comprising D1 and D2 domains truncated from the extracellular domain of SIRPα and an Fc region with a knob mutation.

D1-D2-D3-Fc2

D1-D2-D3-Fc2 refers to a fusion protein comprising D1, D2 and D3 domains truncated from the extracellular domain of SIRPα and an Fc region with a knob mutation.

Treatment

As used herein, the terms "treating" "therapy" and "treatment" are used interchangeably. The term "treating" includes controlling the progression of a disease, a disorder and a condition and related symptoms, preferably reducing or alleviating the influence of one or more symptoms of a disease, a disorder and a condition. This term includes cure of the disease or complete elimination of the symptom. This term includes remission of the symptom. This term also includes, but is not limited to, non-cure palliative treatment. The term "treating" includes administering to a subject a therapeutically effective amount of a pharmaceutical composition comprising the recombinant protein or the fusion protein of the present disclosure to prevent or delay, alleviate or relieve the progression of a disease, a disorder, a condition, or the influence of one or more symptoms of a disease, a disorder and a condition.

Administration

As used herein, the term "administration" refers to the delivery of a therapeutically effective amount of a pharmaceutical composition comprising the recombinant protein or the fusion protein of the present disclosure to a subject. The administration can be systemic or topical. The administration can be performed with a delivery device, such as a syringe. Mode of administration include, but is not limited to, embedding, snorting, spraying, injecting, and the like. Route of administration include inhalation, intranasal, oral, intravenous, subcutaneous or intramuscular administration and the like.

TABLE 2-1

Correspondence between sequence name and sequence number

| Sequence number | Sequence name |
| --- | --- |
| SEQ ID NO: 1 | Ofa heavy chain amino acid sequence |
| SEQ ID NO: 2 | Ofa light chain amino acid sequence |
| SEQ ID NO: 3 | Obi heavy chain amino acid sequence |
| SEQ ID NO: 4 | Obi/Obi-Fc1 light chain amino acid sequence |
| SEQ ID NO: 5 | Hu5F9-G4 heavy chain amino acid sequence |
| SEQ ID NO: 6 | Hu5F9-G4 light chain amino acid sequence |
| SEQ ID NO: 7 | JMT101 heavy chain amino acid sequence |
| SEQ ID NO: 8 | JMT101/Anti-EGFR-Fc1 light chain amino acid sequence |
| SEQ ID NO: 9 | Trastuzumab heavy chain amino acid sequence |
| SEQ ID NO: 10 | Trastuzumab light chain amino acid sequence |
| SEQ ID NO: 11 | SIRPα D1-Fc amino acid sequence |
| SEQ ID NO: 12 | Atezolizumab heavy chain amino acid sequence |
| SEQ ID NO: 13 | Atezolizumab/Anti-PD-L1(Ate)-Fc1 light chain amino acid sequence |
| SEQ ID NO: 14 | D1-Fc2 DNA sequence |
| SEQ ID NO: 15 | D1-D2-Fc2 DNA sequence |
| SEQ ID NO: 16 | Ofa-Fc1 heavy chain amino acid sequence |
| SEQ ID NO: 17 | Ofa-Fc1 light chain amino acid sequence |
| SEQ ID NO: 18 | Obi-Fc1 heavy chain amino acid sequence |
| SEQ ID NO: 19 | Anti-EGFR-Fc1 heavy chain amino acid sequence |
| SEQ ID NO: 20 | Anti-Her2(T)-Fc1 heavy chain amino acid sequence |
| SEQ ID NO: 21 | Anti-Her2(T)-Fc1 light chain amino acid sequence |
| SEQ ID NO: 22 | Anti-Her2(P)-Fc1 heavy chain amino acid sequence |
| SEQ ID NO: 23 | Anti-Her2(P)-Fc1 light chain amino acid sequence |
| SEQ ID NO: 24 | Anti-PD-L1(Ate)-Fc1 heavy chain amino acid sequence |
| SEQ ID NO: 25 | D1-D2-D3-Fc2 DNA sequence |
| SEQ ID NO: 26 | D1-Fc2 amino acid sequence |
| SEQ ID NO: 27 | D1-D2-Fc2 amino acid sequence |
| SEQ ID NO: 28 | D1-D2-D3-Fc2 amino acid sequence |
| SEQ ID NO: 29 | D1'''-Fc2 amino acid sequence |
| SEQ ID NO: 30 | D1 amino acid sequence |
| SEQ ID NO: 31 | D1-D2 amino acid sequence |
| SEQ ID NO: 32 | D1-D2-D3 amino acid sequence |
| SEQ ID NO: 33 | D1''' amino acid sequence |
| SEQ ID NO: 34 | Ofa-Fc1 heavy chain DNA sequence |
| SEQ ID NO: 35 | Ofa-Fc1 light chain DNA sequence |
| SEQ ID NO: 36 | Obi-Fc1 heavy chain DNA sequence |
| SEQ ID NO: 37 | Anti-EGFR-Fc1 heavy chain DNA sequence |
| SEQ ID NO: 38 | Anti-Her2(T)-Fc1 heavy chain DNA sequence |
| SEQ ID NO: 39 | Anti-Her2(T)-Fc1 light chain DNA sequence |
| SEQ ID NO: 40 | Anti-Her2(P)-Fc1 heavy chain DNA sequence |
| SEQ ID NO: 41 | Anti-Her2(P)-Fc1 light chain DNA sequence |
| SEQ ID NO: 42 | Anti-PD-L1(Ate)-Fc1 heavy chain DNA sequence |
| SEQ ID NO: 43 | D1'''-Fc2 DNA sequence |
| SEQ ID NO: 44 | D1'''-D2-Fc2 amino acid sequence |

TABLE 2

Correspondence between the recombinant proteins and the sequences

| Protein name | Sequence number in the sequence listing |
| --- | --- |
| SIRPα D1-Fc | SEQ ID NO: 11 |
| Ofa-Fc1-D1-Fc2 | SEQ ID NO: 16 (Ofa-Fc1 heavy chain) + SEQ ID NO: 17 (Ofa-Fc1 light chain) + SEQ ID NO: 26 (D1-Fc2) |
| Ofa-Fc1-D1'''-Fc2 | SEQ ID NO: 16 (Ofa-Fc1 heavy chain) + SEQ ID NO: 17 (Ofa-Fc1 light chain) + SEQ ID NO: 29 (D1'''-Fc2) |

TABLE 2-continued

Correspondence between the recombinant proteins and the sequences

| Protein name | Sequence number in the sequence listing |
| --- | --- |
| Ofa-Fc1-D1-D2-Fc2 | SEQ ID NO: 16 (Ofa-Fc1 heavy chain) + SEQ ID NO: 17 (Ofa-Fc1 light chain) + SEQ ID NO: 27 (D1-D2-Fc2) |
| Ofa-Fc1-D1'''-D2-Fc2 | SEQ ID NO: 16 (Ofa-Fc1 heavy chain) + SEQ ID NO: 17 (Ofa-Fc1 light chain) + SEQ ID NO: 44 (D1'''-D2-Fc2) |
| Ofa-Fc1-D1-D2-D3-Fc2 | SEQ ID NO: 16 (Ofa-Fc1 heavy chain) + SEQ ID NO: 17 (Ofa-Fc1 light chain) + SEQ ID NO: 28 (D1-D2-D3-Fc2) |
| Obi-Fc1-D1-Fc2 | SEQ ID NO: 18 (Obi-Fc1 heavy chain) + SEQ ID NO: 4 (Obi-Fc1 light chain) + SEQ ID NO: 26 (D1-Fc2) |
| Anti-PD-L1(Ate)-Fc1-D1-Fc2 | SEQ ID NO: 24 (Anti-PD-L1(Ate)-Fc1 heavy chain + SEQ ID NO: 10 (Anti-PD-L1(Ate)-Fc1 light chain) + SEQ ID NO: 26 (D1-Fc2) |
| Anti-PD-L1(13G4)-Fc1-D1-Fc2 | CN104356236A SEQ ID NO: 10 (Anti-PD-L1(13G4)-Fc1 heavy chain) + CN104356236A SEQ ID NO: 20 (Anti-PD-L1(13G4)-Fc1 light chain) + SEQ ID NO: 26 (D1-Fc2) |
| Anti-PD-L1(12A4)-Fc1-D1-Fc2 | CN104356236A SEQ ID NO: 2 (Anti-PD-L1(12A4)-Fc1 heavy chain) + CN104356236A SEQ ID NO: 12 (Anti-PD-L1(12A4)-Fc1 light chain) + SEQ ID NO: 26 (D1-Fc2) |
| Anti-EGFR-Fc1-D1-Fc2 | SEQ ID NO: 19 (Anti-EGFR-Fc1 heavy chain) + SEQ ID NO: 8 (Anti-EGFR-Fc1 light chain) + SEQ ID NO: 26 (D1-Fc2) |
| Anti-Her2(T)-Fc1-D1-Fc2 | SEQ ID NO: 20 (Anti-Her-2(T)-Fc1 heavy chain) + SEQ ID NO: 21 (Anti-Her2(T)-Fc1 light chain) + SEQ ID NO: 26 (D1-Fc2) |
| Anti-Her2(P)-Fc1-D1-Fc2 | SEQ ID NO: 22 (Anti-Her2(P)-Fc1 heavy chain) + SEQ ID NO: 23 (Anti-Her2(P)-Fc1 light chain) + SEQ ID NO: 26 (D1-Fc2) |
| Obi-Fc1-D1'''-Fc2 | SEQ ID NO: 18 (Obi-Fc1 heavy chain) + SEQ ID NO: 4 (Obi-Fc1 light chain) + SEQ ID NO: 29 (D1'''-Fc2) |
| Anti-PD-L1(Ate)-Fc1-D1'''-Fc2 | SEQ ID NO: 24 (Anti-PD-L1(Ate)-Fc1 heavy chain) + SEQ ID NO: 10 (Anti-PD-L1(Ate)-Fc1 light chain) + SEQ ID NO: 29 (D1'''-Fc2) |
| Anti-PD-L1(13G4)-Fc1-D1'''-Fc2 | CN104356236A SEQ ID NO: 10 (Anti-PD-L1(13G4)-Fc1 heavy chain) + CN104356236A SEQ ID NO: 20 (Anti-PD-L1(13G4)-Fc1 light chain) + SEQ ID NO: 29 (D1'''-Fc2) |
| Anti-PD-L1(12A4)-Fc1-D1'''-Fc2 | CN104356236A SEQ ID NO: 2 (Anti-PD-L1(12A4)-Fc1 heavy chain) + CN104356236A SEQ ID NO: 12 (Anti-PD-L1(12A4)-Fc1 light chain) + SEQ ID NO: 29 (D1'''-Fc2) |
| Anti-EGFR-Fc1-D1'''-Fc2 | SEQ ID NO: 19 (Anti-EGFR-Fc1 heavy chain) + SEQ ID NO: 8 (Anti-EGFR-Fc1 light chain) + SEQ ID NO: 29 (D1'''-Fc2) |
| Anti-Her2(T)-Fc1-D1'''-Fc2 | SEQ ID NO: 20 (Anti-Her2(T)-Fc1 heavy chain) + SEQ ID NO: 21 (Anti-Her2(T)-Fc1 light chain) + SEQ ID NO: 29 (D1'''-Fc2) |
| Anti-Her2(P)-Fc1-D1'''-Fc2 | SEQ ID NO: 22 (Anti-Her2(P)-Fc1 heavy chain) + SEQ ID NO: 23 (Anti-Her2(P)-Fc1 light chain) + SEQ ID NO: 29 (D1'''-Fc2) |
| Obi-Fc1-D1-D2-Fc2 | SEQ ID NO: 18 (Obi-Fc1 heavy chain) + SEQ ID NO: 4 (Obi-Fc1 light chain) + SEQ ID NO: 27 (D1-D2-Fc2) |
| Anti-PD-L1(Ate)-Fc1-D1-D2-Fc2 | SEQ ID NO: 24 (Anti-PD-L1(Ate)-Fc1 heavy chain) + SEQ ID NO: 10 (Anti-PD-L1(Ate)-Fc1 light chain) + SEQ ID NO: 27 (D1-D2-Fc2) |
| Anti-PD-L1(13G4)-Fc1-D1-D2-Fc2 | CN104356236A SEQ ID NO: 10 (Anti-PD-L1(13G4)-Fc1 heavy chain) + CN104356236A SEQ ID NO: 20 (Anti-PD-L1(13G4)-Fc1 light chain) + SEQ ID NO: 27 (D1-D2-Fc2) |
| Anti-PD-L1(12A4)-Fc1-D1-D2-Fc2 | CN104356236A SEQ ID NO: 2 (Anti-PD-L1(12A4)-Fc1 heavy chain) + CN104356236A SEQ ID NO: 12 (Anti-PD-L1(12A4)-Fc1 light chain) + SEQ ID NO: 27 (D1-D2-Fc2) |

TABLE 2-continued

Correspondence between the recombinant proteins and the sequences

| Protein name | Sequence number in the sequence listing |
|---|---|
| Anti-EGFR-Fc1-D1-D2-Fc2 | SEQ ID NO: 19 (Anti-EGFR-Fc1 heavy chain) + SEQ ID NO: 8 (Anti-EGFR-Fc1 light chain) + SEQ ID NO: 27 (D1-D2-Fc2) |
| Anti-Her2(T)-Fc1-D1-D2-Fc2 | SEQ ID NO: 20 (Anti-Her2(T)-Fc1 heavy chain) + SEQ ID NO: 21 (Anti-Her2(T)-Fc1 light chain) + SEQ ID NO: 27 (D1-D2-Fc2) |
| Anti-Her2(P)-Fc1-D1-D2-Fc2 | SEQ ID NO: 22 (Anti-Her2(P)-Fc1 heavy chain) + SEQ ID NO: 23 (Anti-Her2(P)-Fc1 light chain) + SEQ ID NO: 27 (D1-D2-Fc2) |
| Obi-Fc1-D1'''-D2-Fc2 | SEQ ID NO: 18 (Obi-Fc1 heavy chain) + SEQ ID NO: 4 (Obi-Fc1 light chain) + SEQ ID NO: 44 (D1'''-D2-Fc2) |
| Anti-PD-L1(Ate)-Fc1-D1'''-D2-Fc2 | SEQ ID NO: 24 (Anti-PD-L1(Ate)-Fc1 heavy chain) + SEQ ID NO: 10 (Anti-PD-L1(Ate)-Fc1 light chain) + SEQ ID NO: 44 (D1'''-D2-Fc2) |
| Anti-PD-L1(13G4)-Fc1-D1'''-D2-Fc2 | CN104356236A SEQ ID NO: 10 (Anti-PD-L1(13G4)-Fc1 heavy chain) + CN104356236A SEQ ID NO: 20 (Anti-PD-L1(13G4)-Fc1 light chain) + SEQ ID NO: 44 (D1'''-D2-Fc2) |
| Anti-PD-L1(12A4)-Fc1-D1'''-D2-Fc2 | CN104356236A SEQ ID NO: 2 (Anti-PD-L1(12A4)-Fc1 heavy chain) + CN104356236A SEQ ID NO: 12 (Anti-PD-L1(12A4)-Fc1 light chain) + SEQ ID NO: 44 (D1'''-D2-Fc2) |
| Anti-EGFR-Fc1-D1'''-D2-Fc2 | SEQ ID NO: 19 (Anti-EGFR-Fc1 heavy chain) + SEQ ID NO: 8 (Anti-EGFR-Fc1 light chain) + SEQ ID NO: 44 (D1'''-D2-Fc2) |
| Anti-Her2(T)-Fc1-D1'''-D2-Fc2 | SEQ ID NO: 20 (Anti-Her2(T)-Fc1 heavy chain) + SEQ ID NO: 21(Anti-Her2(T)-Fc1 light chain) + SEQ ID NO: 44 (D1'''-D2-Fc2) |
| Anti-Her2(P)-Fc1-D1'''-D2-Fc2 | SEQ ID NO: 22 (Anti-Her2(P)-Fc1 heavy chain) + SEQ ID NO: 23 (Anti-Her2(P)-Fc1 light chain) + SEQ ID 44 (D1'''-D2-Fc2) |
| Obi-Fc1-D1-D2-D3-Fc2 | SEQ ID NO: 18 (Obi-Fc1 heavy chain) + SEQ ID NO: 4 (Obi-Fc1 light chain) + SEQ ID NO: 28 (D1-D2-D3-Fc2) |
| Anti-PD-L1(Ate)-Fc1-D1-D2-D3-Fc2 | SEQ ID NO: 24 (Anti-PD-L1(Ate)-Fc1 heavy chain) + SEQ ID NO: 10 (Anti-PD-L1(Ate)-Fc1 light chain) + SEQ ID NO: 28 (D1-D2-D3-Fc2) |
| Anti-PD-L1(13G4)-Fc1-D1-D2-D3-Fc2 | CN104356236A SEQ ID NO: 10 (Anti-PD-L1(13G4)-Fc1 heavy chain) + CN104356236A SEQ ID NO: 20 (Anti-PD-L1(13G4)-Fc1 light chain) + SEQ ID NO: 28 (D1-D2-D3-Fc2) |
| Anti-PD-L1(12A4)-Fc1-D1-D2-D3-Fc2 | CN104356236A SEQ ID NO: 2 (Anti-PD-L1(12A4)-Fc1 heavy chain) + CN104356236A SEQ ID NO: 12 (Anti-PD-L1(12A4)-Fc1 light chain) + SEQ ID NO: 28 (D1-D2-D3-Fc2) |
| Anti-EGFR-Fc1-D1-D2-D3-Fc2 | SEQ ID NO: 19 (Anti-EGFR-Fc1 heavy chain) + SEQ ID NO: 8 (Anti-EGFR-Fc1 light chain) + SEQ ID NO: 28 (D1-D2-D3-Fc2) |
| Anti-Her2(T)-Fc1-D1-D2-D3-Fc2 | SEQ ID NO: 20 (Anti-Her2(T)-Fc1 heavy chain) + SEQ ID NO: 21 (Anti-Her2(T)-Fc1 light chain) + SEQ ID NO: 28 (D1-D2-D3-Fc2) |
| Anti-Her2(P)-Fc1-D1-D2-D3-Fc2 | SEQ ID NO: 22 (Anti-Her2(P)-Fc1 heavy chain) + SEQ ID NO: 23 (Anti-Her2(P)-Fc1 light chain) + SEQ ID NO: 28 (D1-D2-D3-Fc2) |

EXAMPLE 1

Construction of Expression Vector

Basing on the designed molecular structure, the amino acid sequences of each component were spliced together. According to the preference of Chinese hamsters (Cricetulus griseus) for codons, an optimal DNA coding sequence was designed and endonuclease restriction recognition sites for later use in gene cloning operation were excluded. Then a cloning site, Kozak sequence and a signal peptide coding sequence were added successively at the 5' end of the sequence, and a stop codon and a cloning site were added successively at the 3' end of the sequence, as shown in FIG. 1.

Figure 2:
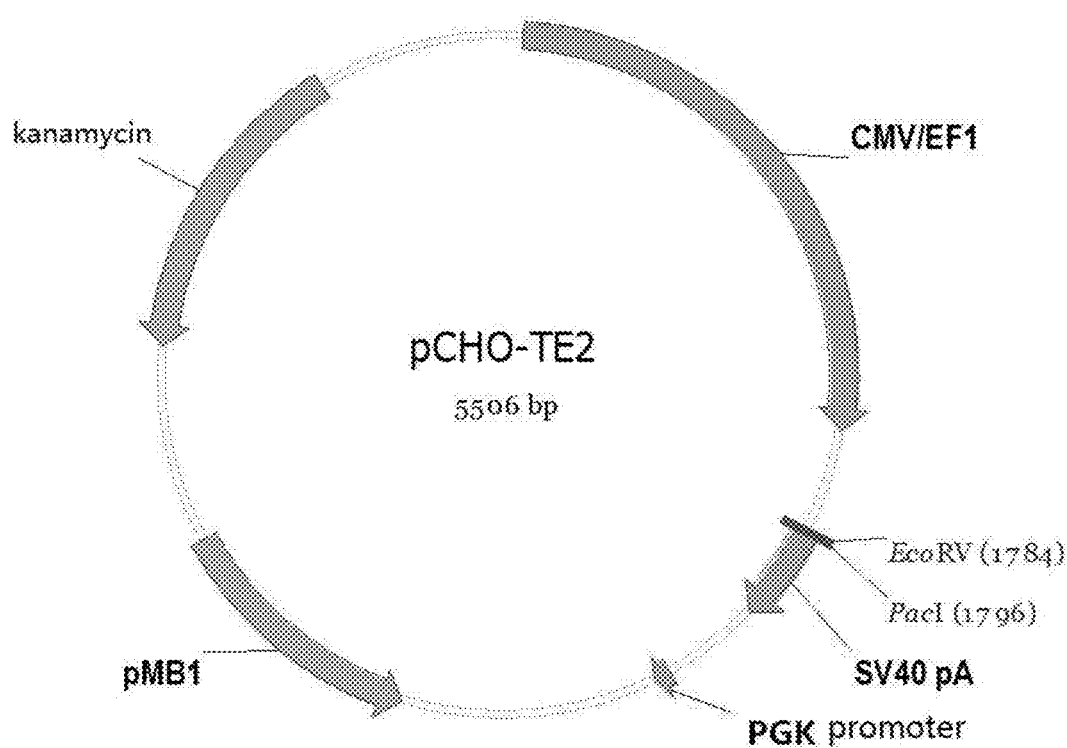
FIG. 2 shows the plasmid map of an exemplary expression vector pCHO-TE2 of the present disclosure.

Whole gene synthesis was performed, and the whole gene was directionally cloned between the corresponding cloning sites of expression vector pCHO-TE2 (purchased from Thermo Fisher) using the 5' end and 3' end cloning sites. After the correctness of the sequence was verified, the expression plasmid was obtained. All the cloning sites used at 5' end and 3' end are EcoRV and PacI sites respectively. FIG. 2 was a plasmid map of the expression vector pCHO-TE2.

EXAMPLE 2

Preparation of Expression Plasmid, Cell Transfection, and Expression and Purification of Target Protein Preparation of Expression Plasmid A bacterial glycerol stock containing the expression plasmid (1 mL of a solution of *Eseherichia coil* containing the expression plasmid was thoroughly mixed with 0.5 mL of 60% sterilized glycerin solution) was inoculated into a liquid LB medium at a ratio of 1:1000. After 16 hours of culture in a shaker at 37° C., 22.0 rpm, the bacteria were collected by centrifugation. The expression plasmid was obtained by using endotoxin-free plasmid prep kits (DP117, purchased from Tiangen Biotech (Beijing) Co., Ltd.) according to the standard procedure provided by kit instructions.

Cell Transfection and Protein Expression

After the obtained expression plasmid was filtered through a 0.22 μm microfiltration membrane, 3 mg of the plasmid solution (wherein the product was a typical antibody molecule, and the ratio of the light chain and the heavy chain expression plasmids were 1:1 (molar ratio); wherein the product was a recombinant protein, the ratio of the light chain, the heavy chain and the right arm expression plasmids were 1:1:1 (molar ratio), as shown in Table 3) was pipetted into 50 mL Opti MEM I Reduced Serum Medium (purchased from GIBCO), then mixed thoroughly. 6 mg of transfection reagent polyetherimide (PEI, purchased from Polysciences, dissolved in sterile ultrapure water at a concentration of 1 mg/mL) was transferred into 50 mL Opti MEM I Reduced Serum Medium, then mixed thoroughly. The obtained PEI solution was added to the Opti MEM I Reduced Serum Medium solution containing the plasmid and mixed thoroughly. The mixture of the plasmid and PEI was allowed to stand at room temperature for 15 minutes, and then slowly and evenly added into 1 L of a suspension of host cell CHO-S (purchased from Thermo Fisher) with a cell density of $3 \times 10^6$ cells/mL. The cells was cultured in an incubator containing 5% $CO_2$ at 37° C. 4 hours later, a feed medium (the feed medium was prepared by dissolving 80 g of CD Efficient Feed C AGT (purchased from Gibco) and 75 g of 5×00483 (purchased from Kerry) in 1 L of water) of a volume equivalent to 7% of the initial volume was added therein. The culture temperature was lowered to 33° C. and the cells were harvested upon 6 days of culture: The cell suspension was centrifuged at 10,000 g, 10° C. for 30 minutes, and the supernatant (i.e., the cell culture harvest solution) was used for purification of the target protein.

Protein Purification

The following method takes Ofa-Fc1-D1-Fc2 as an example, using protein A for affinity-capture of the product.

The above cell culture harvest solution was centrifuged at 10,000 rpm for 30 min to remove the cells and fragments thereof, then loaded onto a protein A affinity column (Art No. 17-5438-02, GE Healthcare), and eluted to harvest the target protein. The purity of the target protein was determined by SDS-PAGE.

The protein A purification method is a conventional protein purification method well known to those skilled in the art, and the detailed test procedure can refer to the product description of GE Healthcare Protein A and the GE antibody purification handbook.

Figure 4:
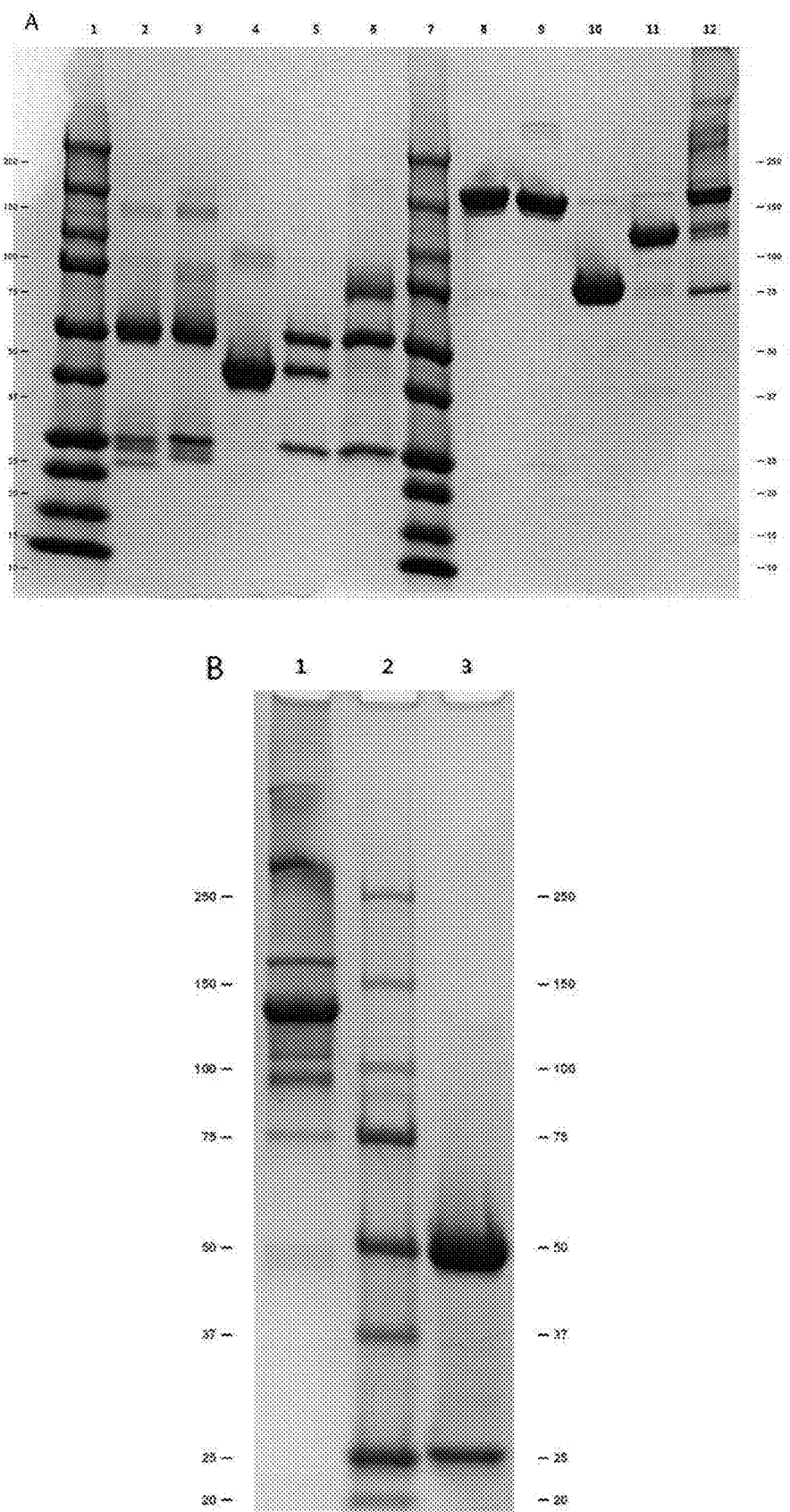
FIG. 4A-4B show the SDS-PAGE electrophoretogram of the recombinant proteins purified by protein A. Lanes 1-6 of FIG. 4A show reduced samples, wherein, 1: Marker; 2: Anti-CD20 mAb (Ofatumumab); 3: Anti-CD47 mAb (Hu5F9-G4); 4: SIRPα D1-Fc; 5: Ofa-Fc1-D1-Fc2; 6: Ofa-Fc1-D1-D2-D3-Fc2. Lanes 7-12 of FIG. 4A show non-reduced samples, wherein, 7: Marker; 8: Anti-CD20 mAb (Ofatumumab); 9: Anti-CD47 mAb (Hu5F9-G4); 10: SIRPα D1-Fc; 11: Ofa-Fc1-D1-Fc2; 12: Ofa-Fc1-D1-D2-D3-Fc2. Lane 1 of FIG. 4B: the non-reduced sample of Ofa-Fc1-D1-D2-Fc2; Lane 2 of FIG. 4B; Marker; Lane 3 of FIG. 4B: the reduced sample of Ofa-Fc1-D1-D2-Fc2.

The theoretical molecular weights of the four proteins SIRPα D1-Fc, Ofa-Fc1-D1-Fc2, Ofa-Fc1-D1-D2-Fc2, and Ofa-Fc1-D1-D2-D3-Fc2 are 37.8 kD, 110.7 kD, 121.7 kD and 131.4 kD, respectively. The results of SDS-PAGE are shown in FIG. 4A and FIG. 4B.

Protein electrophoresis (SDS-PAGE): The results show (FIG. 4A and FIG. 4B) that the target proteins in each lane are efficiently expressed and purified, wherein Ofa-Fc1-D1-Fc2 (FIG. 4A, lane 11), Ofa-Fc1-D1-D2-Fc2 (FIG. 4A, lane 1) and Ofa-Fc1-D1-D2-D3-Fc2 (FIG. 4A, lane 12) shows different degrees of left arm dialer (Ofa-Fc1-Ofa-Fc1), right arm dimer (SIRPα-Fc2) and/or multimer.

TABLE 3

Ratio of the expression plasmid

| | Product | Ratio of the expression plasmid |
|---|---|---|
| Typical antibody molecules/ fusion protein dimer | Anti-CD20 mAb (Ofatumumab)<br>Anti-CD20 mAb (Obinutuzumab)<br>Anti-EGFR mAb (JMT101)<br>Anti-CD47 mAb (Hu5F9-G4)<br>Anti-Her2(T) mAb (Transtuzumab)<br>Anti-Her2(P) mAb (Pertuzumab)<br>Anti-PD-L1mAb (Atezolizumab)<br>Anti-PD-L1mAb(12A4)<br>Anti-PD-L1mAb (13G4)<br>SIRPα D1-Fc | the ratio of the light chain and the heavy chain expression plasmids were 1:1<br><br>Dimer |
| Recombinant proteins | Ofa-Fc1-D1-Fc2<br>Ofa-Fc1-D1′′′-Fc2<br>Ofa-Fc1-D1-D2-Fc2<br>Ofa-Fc1-D1′′′-D2-Fc2<br>Ofa-Fc1-D1-D2-D3-Fc2<br>Obi-Fc1-D1-Fc2<br>Anti-PD-L1(Ate)-Fc1-D1-Fc2<br>Anti-PD-L1(13G4)-Fc1-D1-Fc2<br>Anti-PD-L1(12A4)-Fc1-D1-Fc2<br>Anti-EGFR-Fc1-D1-Fc2<br>Anti-Her2(T)-Fc1-D1-Fc2<br>Anti-Her2(P)-Fc1-D1-Fc2<br>Obi-Fc1-D1′′′-Fc2<br>Anti-PD-L1(Ate)-Fc1-D1′′′ -Fc2<br>Anti-PD-L1(13G4)-Fc1-D1′′′ -Fc2<br>Anti-PD-L1(12A4)-Fc1-D1′′′ -Fc2<br>Anti-EGFR-Fc1-D1′′′-Fc2<br>Anti-Her2(T)-Fc1-D1′′′-Fc2 | the ratio of the expression plasmids of light chain, heavy chain and right arm follows the aforementioned ratio |

TABLE 3-continued

| Ratio of the expression plasmid | |
|---|---|
| Product | Ratio of the expression plasmid |
| Anti-Her2(P)-Fc1-D1‴-Fc2 | |
| Obi-Fc1-D1-D2-Fc2 | |
| Anti-PD-L1(Ate)-Fc1-D1-D2-Fc2 | |
| Anti-PD-L1(13G4)-Fc1-D1-D2-Fc2 | |
| Anti-PD-L1(12A4)-Fc1-D1-D2-Fc2 | |
| Anti-EGFR-Fc1-D1-D2-Fc2 | |
| Anti-Her2(T)-Fc1-D1-D2-Fc2 | |
| Anti-Her2(P)-Fc1-D1-D2-Fc2 | |
| Obi-Fc1-D1‴-D2-Fc2 | |
| Anti-PD-L1(Ate)-Fc1-D1‴-D2-Fc2 | |
| Anti-PD-L1(13G4)-Fc1-D1‴-D2-Fc2 | |
| Anti-PD-L1(12A4)-Fc1-D1‴-D2-Fc2 | |
| Anti-EGFR-Fc1-D1‴-D2-Fc2 | |
| Anti-Her2(T)-Fc1-D1‴-D2-Fc2 | |
| Anti-Her2(P)-Fc1-D1‴-D2-Fc2 | |
| Obi-Fc1-D1-D2-D3-Fc2 | |
| Anti-PD-L1(Ate)-Fc1-D1-D2-D3-Fc2 | |
| Anti-PD-L1(13G4)-Fc1-D1-D2-D3-Fc2 | |
| Anti-PD-L1(12A4)-Fc1-D1-D2-D3-Fc2 | |
| Anti-EGFR-Fc1-D1-D2-D3-Fc2 | |
| Anti-Her2(T)-Fc1-D1-D2-D3-Fc2 | |
| Anti-Her2(P)-Fc1-D1-D2-D3-Fc2 | |

Notes:
D1‴represents a high affinity mutant of SIRPα extracellular truncated variantD1; D1 represents the extracellular D1 domain of human wild-type SIRPα and its non-high affinity mutant; Fc is a wild-type Fc region; Fc1 is an Fc region having a hole or holes mutation(s), and Fc2 is an Fc region having a knob or knobs mutation(s).

EXAMPLE 3

Determination of Affinity, Competitive Binding Activity to the Target

1. Detection method for affinity of the target CD47, CD20, EGFR and Her2

The binding affinity of the recombinant proteins Ofa-Fc1-D1-Fc2, Ofa-Fc1-D1‴-Fc2, Ofa-Fc1-Dc1-D2-Fc2, Ofa-Fc1-D1‴-D2-Fc2, Ofa-Fc1-D1-D2-D3-Fc2, Obi-Fc1-D1-Fc2, Obi-Fc1-D1‴-Fc2, Obi-Fc1-D1-D2-Fc2, Obi-Fc1-D1‴-D2-Fc and Obi-Fc1-D1-D2-D3-Fc2 to the targets CD47 and CD20 was determined by ELISA and/or flow cytometry. Taking Ofa-Fc1-D1-Fc2 as an example, the following detect method is suitable for the recombinant proteins with a left arm targeting CD20.

The binding affinity of the recombinant proteins Anti-Her2(P)-Fc1-D1-Fc2, Anti-Her2(P)-Fc1-D1‴-Fc2, Anti-Her2(P)-Fc1-D1-D2-Fc2, Anti-Her2(P)-Fc1-D1‴-D2-Fc2, Anti-Her2(P)-Fc1-D1-D2-D3-Fc2, Anti-Her2(P)-Fc1-D1-Fc2, Anti-Her2(P)-Fc1-D1‴-Fc2, Anti-Her2(P)-Fc1-D1-D2-Ec2, Anti-Her2(P)-Fc1-D1‴-D2-Fc2, Anti-Her2(P)-Fc1-D1-D2-D3-Fc2, Anti-Her2(T)-Fc1-D1-Fc2, Anti-Her2(T)-Fc1-D1‴-Fc2, Anti-Her2(T)-Fc1-D1-D2-Fc2, Anti-Her2(T)-Fc1-D1‴-D2-Fc2, Anti-Her2(T)-Fc1-D1-D2-D3-Fc2, Anti-Her2(T)-Fc1-D1-Fc2, Anti-Her2(T)-Fc1-D1‴-Fc2, Anti-Her2(T)-Fc1-D1-D2-Fc2, Anti-Her2(T)-Fc1-D1‴-D2-Fc2 and Anti-Her2(T)-Fc1-D1-D2-D3-Fc2 to the targets CD47 and Her2 was determined by ELISA and/or flow cytometry. Taking Anti-Her2(T)-Fc1-D1-Fc2 as an example, the following detect method is suitable for the recombinant proteins with a left arm targeting Her2.

The binding affinity of the recombinant proteins Anti-EGFR-Fc1-D1-Fe2, Anti-EGFR-Fc1-D1‴-Fc2, Anti-EGFR-Fc1-D1-D2-Fc2, Anti-EGFR-Fc1-D1‴-D2-Fc2 and Anti-EGFR-Fc1-D1-D2-D3-Fc2 to the targets CD47 and EGFR was determined by ELISA and/or flow cytometry.

Taking Anti-EGFR-Fc1-D1-Fc as an example, the following detect method is suitable for the recombinant proteins with a left arm targeting EGFR.

The binding affinity of the recombinant proteins Anti-PD-L1(Ate)-Fc1-D1-Fc2, Anti-PD-L1(Ate)-Fc1-D1‴-Fc2, Anti-PD-L1(Ate)-Fc1-D1-D2-Fc2, Anti-PD-L1(Ate)-Fc1-D1‴-D2-Fc2 Anti-PD-L1(Ate)-Fc1-D1-D2-D3-Fc2, Anti-PD-L1(13G4)-Fc1-D1-Fc2, Anti-PD-L1(13G4)-Fc1-D1‴-Fc2, Anti-PD-L1(13G4)-Fc1-D1-D2-Fc2, Anti-PD-L1(13G4)-Fc1-D1‴-D2-Fc2, Anti-PD-L1(13G4)-Fc1-D1-D2-D3-Fc2, Anti-PD-L1(12A4)-Fc1-D1-Fc2, Anti-PD-L1(12A4)-Fc1-D1‴-Fc2, Anti-PD-L1(12A4)-Fc1-D1-D2-Fc2, Anti-PD-L1(12A4)-Fc1-D1‴-D2-Fc2 and Anti-PD-L1(12A4)-Fc1-D1-D2-D3-Fc2 to the targets CD47 and PD-L1 was determined by ELISA. Taking Anti-PD-L1(Ate)-Fc1-D1-Fc2 as an example, the following detect method is suitable for the recombinant proteins with a left arm targeting PD-L1.

Determination of the Affinity of Ofa-Fc1-D1-Fc2 and Anti-EGFR-Fc1-D1-Fc2 to the target CD47 by ELISA:

An ELISA plate (Art No. 9018, Corning) was coated with 100 μL of 1 μg/mL CD47-His (12283-H08H-200, Sino Biological) and placed at 4° C. overnight. The plate was rinsed with PBST solution (PBS containing 0.1% Tweet 20), and then blocked with PBS+1% BSA for 2 hours at room temperature. After rinsing, 100 μL of diluted Ofa-Fc1-D1-Fc2 and Anti-EGFR-Fc1-D1-Fc2 (2,5-fold serial dilutions starting from 1000 ng/mL, 11 dilutions) was added to each well of the coated plate, then incubated for 1 hour at 25° C. After discarding the sample and rinsing the plate three times with PBST solution, 100 μL of diluted mouse anti-human IgG Fc-HRP (1:10000) (Ab7499, abeam) was added, then incubated at 25° C. for 1 hour. After discarding the solution and rinsing the plate three times with PBST solution, TMB (P0209, beyotime) was added, and the plate was developed and protected from light for about 20 minutes. The reaction was stopped with $H_2SO_4$, and the OD value at 450-650 nm was read on a microplate reader.

The test results showed that anti-CD47 antibodies Hu5F9-G4, SIRPα D1-Fc, Ofa-Fc1-D1-Fc2, Ofa-Fc1-D1'''-Fc2, Ofa-Fc1-D1-D2-Fc2, Ofa-Fc1-D1'''-D2-Fc2, Ofa-Fc1-D1-D2-D3-Fc2, Obi-Fc1-D1-Fc2, Obi-Fc1-D1'''-Fc2, Obi-Fc1-D1-D2-Fc2, Obi-Fc1-D1'''-D1-D2-Fc2, Obi-Fc1-D1-D2-D3-Fc2, Anti-EGFR-Fc1-D1-Fc2, Anti-EGFR-Fc1-D1'''-Fc2, Anti-EGFR-Fc1-D1-D2-Fc2, Anti-EGFR-Fc1-D1'''-D2-Fc2, Anti-EGFR-Fc1-D1-D2-D3-Fc2 were all capable of binding to CD47; the binding affinity of Ofa-Fc1-D1-Fc2, Ofa-Fc1-D1-D2-Fc2, Ofa-Fc1-D1-D2-D3-Fc2, Obi-Fc1-D1-Fc2, Obi-Fc1-D1-D2-Fc2, Obi-Fc1-D1-D2-D3-Fc2, Anti-EGFR-Fc1-D1-Fc2, Anti-EGFR-Fc1-D1-D2-Fc2, Anti-EGFR-Fc1-D1-D2-D3-Fc2 to CD47 was slightly weaker than the binding affinity of anti-CD47 antibody Hu5F9-64 and/or SIRPα D1-Fc to CD47.

The above test results demonstrate that the recombinant proteins of the present disclosure are capable of specifically targeting the CD47 antigen on tumor cells at the protein level, and their binding affinity to CD47 is not higher than the binding affinity of SIRPα D1-Fc fusion protein to CD47. The recombinant proteins of the present disclosure can reduce or avoid the side effects such as RBC agglutination, anemia caused by the treatment with anti-CD47 antibody and/or killing of non-tumor target cells caused by the treatment with high affinity SIRPα, mutant (Petrova P S, et al, TTI-621 (SIRPα Fc): A CD47-Blocking Innate Immune Checkpoint Inhibitor with Broad Antitumor Activity and Minimal Erythrocyte Binding. *Clin Cancer Res*, 2017, 23(4): 1068-1079).

Figure 5:
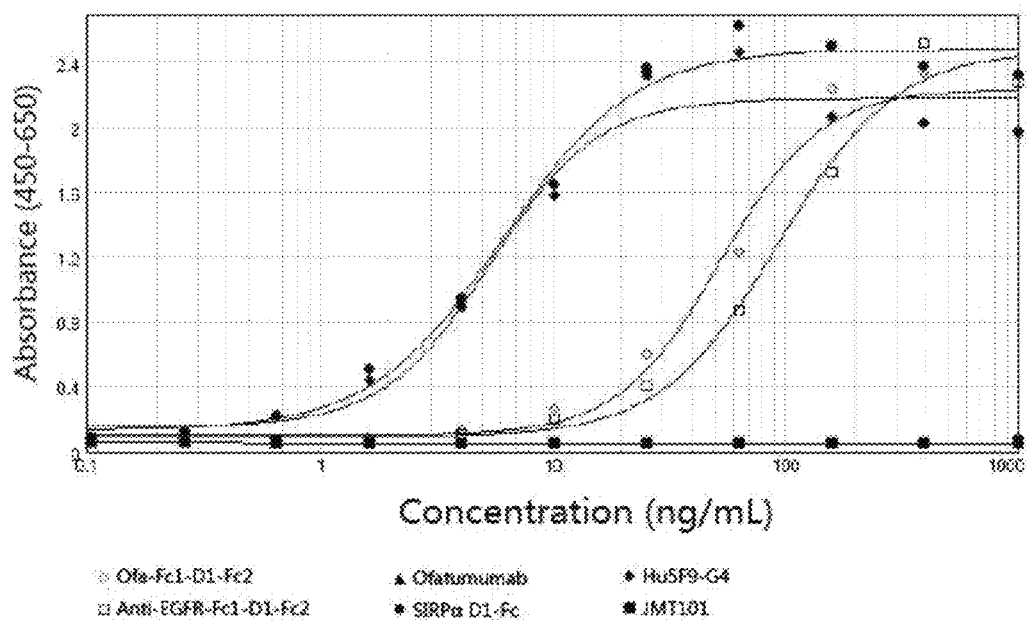
FIG. 5 shows the ELISA detection results of the binding affinity of the recombinant proteins of the present disclosure to human CD47 (protein level).

For example, as shown in FIG. 5, except that the anti-CD20 antibody Ofatumumab and the anti-EGFR antibody JMT101 cannot bind to CD47, anti-CD47 antibodies Hu5F9-G4, SIRPα D1-Fc, OFa-Fc1-D1-Fc2, Anti-EGFR-Fc1-D1-Fc2 are all capable of binding to CD47. However, the binding affinity of Ofa-Fc1-D1-Fc2 and Anti-EGFR-Fc1-D1-Fc2 (EC$_{50}$=52.57 ng/mL, EC$_{50}$=93.86 ng/mL), of which only the right arm can bind to CD47 antigen, is weaker than that of anti-CD47 antibody (EC$_{50}$=5.439 ng/mL) and SIRPα D1-Fc (EC50=6.118 ng/mL).

Determination of Affinity of Ofa-Fc1-D1-Fc2 to the Target CD47 by ELISA Flow Cytometry Well-grown A431 cells (human epidermal cancer cell) were collected and counted, centrifuged and resuspended to a concentration of 3×10$^6$ cells/mL with PBS+2% FBS (purchased from Gibco). 100 μL of the cell suspension was aliquoted to each well of a 96-well U-plate (Art No. 3799, Corning) and allowed to stand for at least 15 minutes. The supernatant was pipetted and discarded after centrifugation, then 9 serial dilutions of Ofa-Fc1-D1-Fc2 were added (5-fold serial dilutions starting from 15000 ng/mL, a total of 9 concentrations) and incubated in a refrigerator at 4° C. for 1 hour. After rinsing with PBS+2% FBS, goat anti-human IgG Fc-FITC (F9512-2ML, Sigma) was added and incubated for 1 hour at 4° C. After rinsing and resuspension with PBS+2% FBS, the fluorescence value was determined by a flow cytometer (Accuri C6, BD).

Since A431 cells do not express CD20 antigen and cannot bind to Ofatumumab and Obinutuzumab, A431 cells can be used to evaluate the binding affinity of Ofa-Fc1-D1-Fc2, Ofa-Fc1-D1'''-Fc2, Ofa-Fc1-D1-D2-Fc2, Ofa-Fc1-D1'''-D2-Fc2, Ofa-Fc1-D1-D2-D3-Fc2, Obi-Fc1-D1-Fc2, Obi-Fc1-D1-D2-Fc2, Obi-Fc1-D1'''-D2-Fc2 and Obi-Fc1-D1-D2-D3-Fc to CD47 at the cellular level.

The test results showed, except that the anti-CD20 antibodies Ofatumumab and Obinutuzumab cannot bind to A431 cells, anti-CD47 antibodies Hu5F9-G4, SIRPα D1-Fc, Ofa-Fc1-D1-Fc2, Ofa-Fc1-D1'''-Fc2, Ofa-Fc1-D1-D2-Fc2, Ofa-Fc1-D1'''-D2-Fc2, Ofa-Fc1-D1-D2-D3-Fc2, Obi-Fc1-D1-Fc2, Obi-Fc1-D1'''-Fc2, Obi-Fc1-D1-D2-Fc2, Obi-Fc1-D1'''-D2-Fc2 and Obi-Fc1-D1-D2-D3-Fc2 were all capable of binding to A431 cells. The binding affinity of Ofa-Fc1-D1-Fc2, Ofa-Fc1-D1-D2-Fc2, Ofa-Fc1-D1-D2-D3-Fc2, Obi-Fc1-D1-Fc2, Obi-Fc1-D1-D2-Fc2 and Obi-Fc1-D1-D2-D3-Fc2 to CD47 was slightly weaker than the binding affinity of anti-CD47 antibody and/or SIRPα D1-Fc to CD47, which was consistent with the trend of ELISA data.

The above test results demonstrate that the recombinant proteins of the present disclosure are capable of specifically targeting the CD47 antigen on tumor cells at the protein level, and the binding affinity to CD47 is not higher than the binding affinity of SIRPα D1-Fc fusion protein to CD47. The recombinant proteins of the present disclosure can reduce or avoid the side effects such as RBC agglutination, anemia caused by the treatment with anti-CD47 antibody and/or killing of non-tumor target cells caused by the treatment with high affinity SIRPα mutant.

Figure 6:
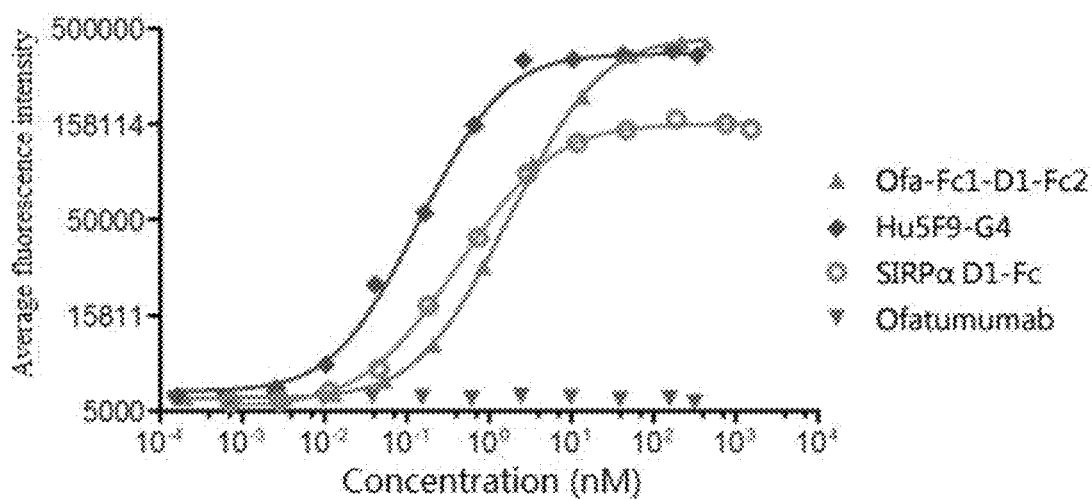
FIG. 6 shows the flow cytometry results of the binding affinity of the recombinant proteins of the present disclosure to human CD47 (cellular level).

For example, as shown in FIG. 6, anti-CD47 antibodies Hu5F9-G4, SIRPα D1-Fc and Ofa-Fc1-D1-Fc2 are all capable of binding to A431 cells. Specifically, the binding affinity of Ofa-Fc1-D1-Fc2 is slightly weaker than that of the anti-CD47 antibody and/or SIRPα D1-Fc, which is consistent with the trend of ELISA data.

Determination of Affinity of Ofa-Fc1-D1-Fc2 to the target CD20 by Flow Cytometry Well-grown Raji cells (human B-cell lymphoma, purchased from the Cell Bank of Chinese Academy of Sciences, Shanghai) were collected and counted, centrifuged and resuspended to a concentration of 3×10$^6$ cells/MI, with PBS+2% FBS. 100 μL of the cell suspension was aliquoted to each of a 96-well U-plate (Art No. 3799, Corning) and allowed to stand for at least 15 minutes. The supernatant was pipetted and discarded after centrifugation, then 100 μL, PBS+2% FBS (control group) or 1.5 μg/mL, anti-CD47 antibody Hu5F9-G4 (Fab)2 (treatment group) (excising Fc by pepsin, kit: Thermo Fisher, 44988) were added and incubated at 4° C. for 1 hour. After rinsing with PBS+2% FBS, 7 serial dilutions of Ofa-Fc1-D1-Fc2, Hu5F9-G4 or SIRPα D1-Fc (4-fold serial dilutions starting from 6250 ng/mL, with a total of 7 dilutions, and the molar concentration after conversion is shown in FIG. 7) were added respectively and then incubated at 4° C. for 1 hour. After rinsing with PBS+2% FBS, goat anti-human IgG Fc-FITC (F9512-2ML, Sigma) was added and incubated for 1 hour at 4° C. After rinsing and resuspension with PBS+2% FBS, the fluorescence value was determined by a flow cytometer (Accuri C6, BD).

The test results showed that the anti-CD47 antibody Hu5F9-G4(Fab)2 effectively blocked the binding of the anti-CD47 antibody Hu5F9-G4 and/or SIRPα D1-Fc to CD47 on Raji cells. However, the blocking effect of Hu5F9-G4(Fab)2 on CD47 antigen did not significantly inhibit the binding of Ofa-Fc1-D1-Fc2, Ofa-Fc1-D1-D2-Fc2, Ofa-Fc1-D1-D2-D3-Fc2, Obi-Fc1-D1-Fc2, Obi Fc1-D1-D2-Fc2 and Obi-Fc1-D1-D2-D3-Fc2 to Raji cells.

The above test results demonstrate that, in the case where the CD47 antigen on the surface of tumor cells is shielded and the binding to SIRPα-CD47 is blocked, the recombinant proteins of the present disclosure are still capable of specifically binding to the corresponding antigen on tumor cells by the left arm, and the affinity of the left arm is not significantly affected by blocking the binding of the right arm.

For example, as shown in FIG. 7, the anti-CD47 antibody Hu5F9-G4(Fab)2 effectively blocks the binding of the anti-CD47 antibody Hu5F9-G4 and/or SIRPα D1-Fc to CD47 on Raji cells. However, the blocking effect of Hu5F9-G4(Fab)2 on CD47 antigen does not significantly inhibit the binding of Ofa-Fc1-D1-Fc2 to Raji cells, indicating that Ofa-Fc1-D1-Fc2 is still capable of specifically binding to the CD20 antigen on Raji cells by its left arm (anti-CD20 half antibody) after the mutual combination of SIRPα-CD47 is blocked, and the affinity is not significantly affected by blocking the binding of the right arm.

Figure 8:
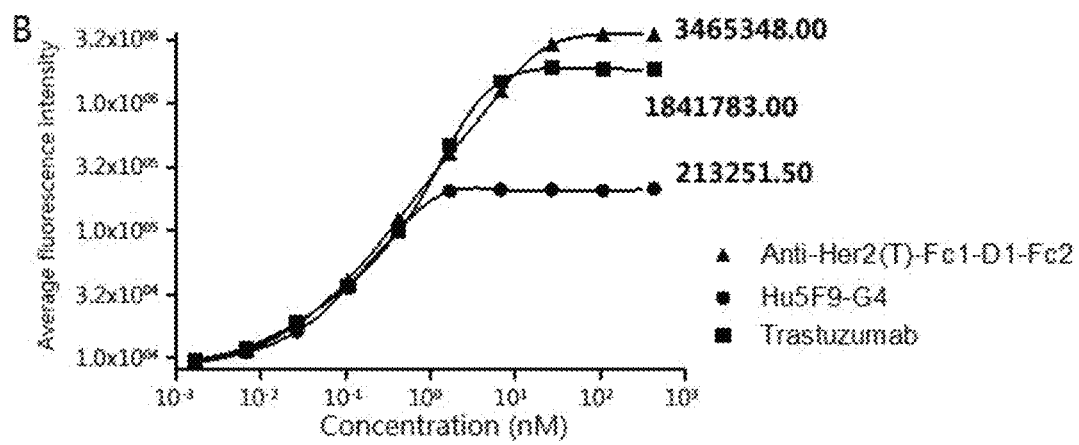
FIG. 8 shows the flow cytometry results of the binding affinity of the recombinant proteins of the present disclosure to the cells expressing both the CD47 and the target corresponding to the left arm.
Figure 8:
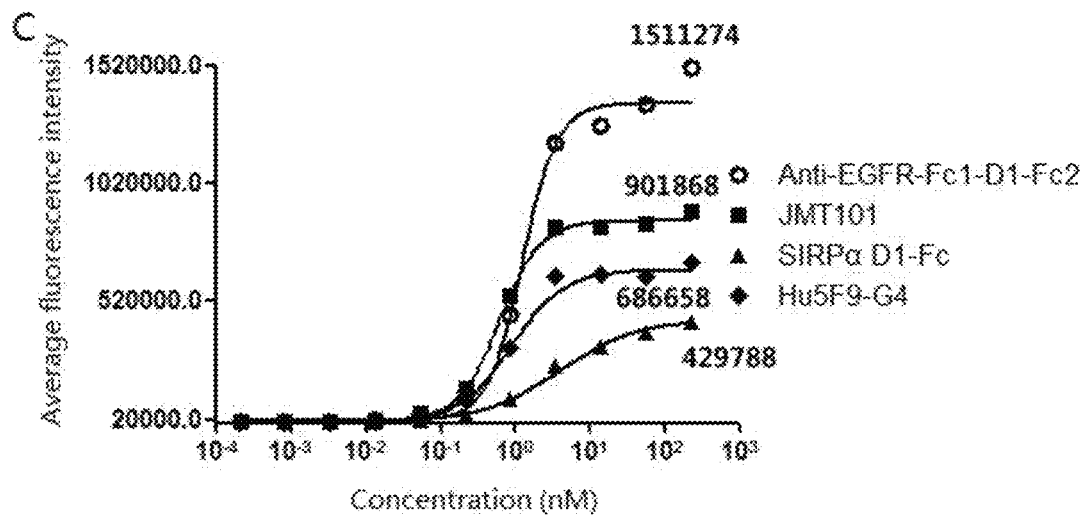
Figure 8:
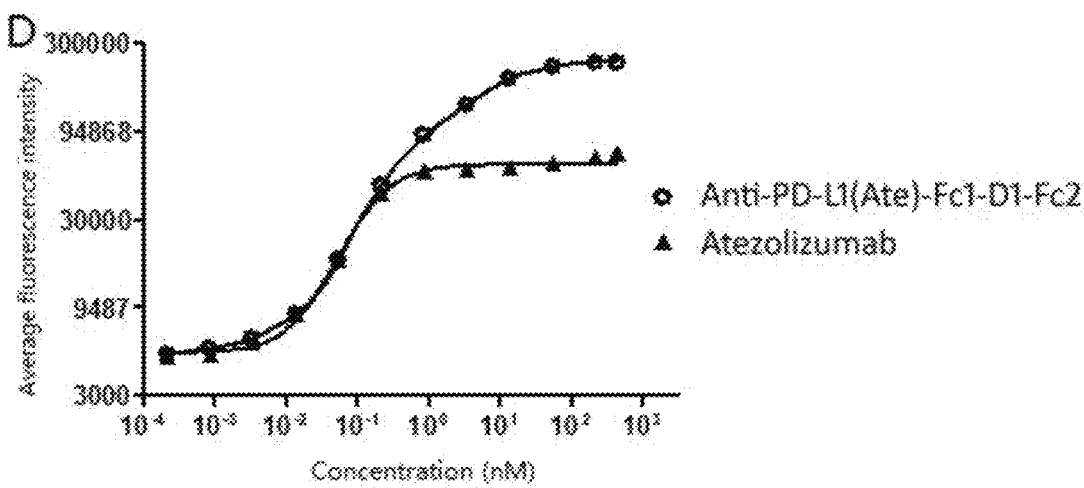

Determination of Bispecific Binding Activity to the Targets CD20 and CD47 by Flow Cytometry Well-grown Raji cells (human B-cell lymphoma, purchased from the Cell Bank of Chinese Academy of Sciences, Shanghai) were collected and counted, centrifuged and resuspended to a concentration of $3\times10^6$ cells/mL with PBS+2% FBS. 100 μL of the cell suspension was aliquoted to each well of a 96-well U-plate (Art No. 3799, Corning) and allowed to stand for at least 15 minutes. The supernatant was pipetted and discarded after centrifugation, then 12 serial dilutions of Ofa-Fc1-D1-Fc2, Ofatumumab, Hu5F9-G4 or SIRPα D1-Fc (50000 ng/mL, 25000 ng/mL, 6250 ng/mL and 4-fold serial dilutions starting from 6250 ng/mL, with a total of 12 dilutions, and the molar concentration after conversion is shown in FIG. 8A) were added respectively and incubated at 4° C. for 1 hour. After rinsing with PBS+2% FBS, goat anti-human IgG Fc-FITC (F9512-2ML, Sigma) was added and incubated for 1 hour at 4° C. After rinsing and resuspension with PBS+2% FBS, the fluorescence value was determined by a flow cytometer (Accuri C6, BD).

Since the surface of Raji cells simultaneously expresses CD20 and CD47 antigens, the anti-CD20 antibodies Ofatumumab, Obinutuzumab, anti-CD47 antibody Hu5F9-G4 and SIRPα D1-Fc are all capable of specifically binding to Raji cells, but their maximum average fluorescence intensities are not identical to each other.

The test results showed that Ofa-Fc1-D1-Fc2, Ofa-Fc1-D1'''-Fc2, Ofa-Fc1-D1-D2-Fc2, Ofa-Fc1-D1'''-D2-Fc2, Ofa-Fc1-D1-D2-D3-Fc2, Obi-Fc1-D1-Fc2, Obi-Fc1-D1'''-Fc2, Obi-Fc1-D1-D2-Fc2, Obi-Fc1-D1'''-D2-Fc2 and Obi-Fc1-D1-D2-D3-Fc2 were capable of binding to Raji cells, and achieved a higher maximum average fluorescence intensity.

The above test results demonstrate that the recombinant proteins of the present disclosure, compared with the anti-CD20 antibodies Ofatumumab, Obinutuzumab and/or the anti-CD47 antibody Hu5F9-G4 and/or SIRPα D1-Fc, are capable of specifically binding to tumor cells and exhibit a significant advantage in the number of molecules under the environment of a same supersaturated protein concentration. Preferably, the saturation binding abundance of the recombinant proteins of the present disclosure to tumor cells is greater than the sum of the saturation binding abundance of the anti-CD20 antibody and SIRPα D1-Fc to tumor cells under the environment of a same supersaturated protein concentration.

TABLE 4

Maximum average fluorescence intensity and $EC_{50}$ (nM) of the binding of antibodies/recombinant proteins to Raji cells

| | Sample | | | |
|---|---|---|---|---|
| | Ofatumumab | Ofa-Fc1-D1-Fc2 | Hu5F9-G4 | SIRPα D1-Fc |
| Maximum average fluorescence intensity | 252065.10 | 690705.90 | 93784.59 | 104997.50 |
| $EC_{50}$ (nM) | 1.586 | 14.06 | 0.258 | 12.53 |

For example, as shown in FIG. 8A and Table 4, the anti-CD20 antibody Ofatumumab, the anti-CD47 antibody Hu5F9-G4 and SIRPα D1-Fc are all capable of specifically binding to Raji cells, but their maximum average fluorescence intensities are various; meanwhile, Ofa-Fc1-D1-Fc2 is also capable of binding to Raji cells and has a higher maximum average fluorescence intensity, indicating that under the condition of a same supersaturated protein concentration, the number of Ofa-Fc1-D1-Fc2 molecules specifically binding to Raji cells is significantly greater than that of the anti-CD20 antibody Ofatumumab or the anti-CD47 antibody Hu5F9-G4 or SIRPα D1-Fc molecules, greater than the sum of the anti-CD20 antibody Ofatumab and the anti-CD47 antibody Hu5F9-G4 molecules, and greater than the sum of the antibody Ofatumumab and SIRPα D1-Fc molecules.

As known to those skilled in the art, the above test results indicate that the recombinant proteins of the present disclosure which are capable of simultaneously binding to both the tumor-targeting antigen and CD47 can bind more to tumor cells and thus provide a more significant anti-tumor effect, compared with the combination therapy of the anti-CD47 antibody or SIRPα D1-Fc with another tumor-targeting therapeutic antibody.

Determination of Bispecific Binding Activity to the Targets Her2 and CD47 by Flow Cytometry Well-grown SKBR-3 cells (human breast cancer cell, purchased from the Cell Bank of Chinese Academy of Sciences, Shanghai) were collected and counted, centrifuged and resuspended to a concentration of $2\times10^6$ cells/mL with PBS+2% FBS. 100 μL of the cell suspension was aliquoted to each well of a 96-well U-plate (Art No. 3799, Corning) and allowed to stand for at least 15 minutes. The supernatant was pipetted and discarded after centrifugation, then 10 dilutions of Anti-Her2(T)-Fc1-D1-Fc2, Trastuzumab or Hu5F9-G4 (4-fold serial dilutions starting from 433.2 nM, a total of 10 dilutions) were added respectively and incubated at 4° C. for 1 hour. After rinsing with PBS+2% FBS, goat anti-human IgG Fc-FITC (F9512-2ML, Sigma) was added and incubated for 1 hour at 4° C. After rinsing and resuspension with PBS+2% FBS, the fluorescence value was determined by a flow cytometer (Accuri C6, BD).

Since the surface of SKBR-3 cells simultaneously expresses Her2 and CD47 antigens, the anti-Her2 antibodies Trastuzumab, Pertuzumab, the anti-CD47 antibody. Hu5F9-G4 and SIRPα D1-Fc are all capable of specifically binding to SKBR-3 cells, but their maximum average fluorescence intensities are various.

The test results showed that Anti-Her2(P)-Fc1-D1-Fc2, Anti-Her2(P)-Fc1-D1'''-Fc2, Anti-Her2(P)-Fc1-D1-D2-Fc2, Anti-Her2(P)-Fc1-D1'''-D2-Fc2, Anti-Her2(P)-Fc1-D1-D2-D3-Fc2, Anti-Her2(P)-Fc1-D1-Fc2, Anti-Her2(P)-Fc1-D1'''-Fc2, Anti-Her2(P)-Fc1-D1-D2-Fc2, Anti-Her2(P)-

Fc1-D1'''-D2-Fc2, Anti-Her2(P)-Fc1-D1-D2-D3-Fc2, Anti-Her2(T)-Fc1-D1-Fc2, Anti-Her2(T)-Fc1-D1'''-Fc2, Anti-Her2(T)-Fc1-D1-D2-Fc2, Anti-Her2(T)-Fc1-D1'''-D2-Fc2, Anti-Her2(T)-Fc1-D1-D2-D3-Fc2, Anti-Her2(T)-Fc1-D1-Fc2, Anti-Her2(T)-Fc1-D1'''-Fc2, Anti-Her2(T)-Fc1-D1-D2-Fc2, Anti-Her2(T)-Fc1-D1'''-D2-Fc2 and Anti-Her2(T)-Fc1-D1-D2-D3-Fc2 were capable of binding to SKBR-3 cells, and achieved a higher maximum average fluorescence intensity.

The above test results demonstrate that the recombinant proteins of the present disclosure, are capable of specifically binding to tumor cells and exhibit a significant advantage in the number of molecules under the condition of a same supersaturated protein concentration, compared with the anti-Her2 antibodies Trastuzumab, Pertuzumab and/or the anti-CD47 antibody Hu5F9-G4 and/or SIRPα D1-Fc. Preferably, the saturation binding abundance of the recombinant proteins of the present disclosure to tumor cells is greater than the sum of the saturation binding abundance of the anti-Her2 antibody and SIRPα D1-Fc to tumor cells under the environment of a same supersaturated protein concentration.

TABLE 5

Maximum average fluorescence intensity and $EC_{50}$ (nM) of the binding of antibodies/recombinant proteins to SKBR-3 cells

| | Sample | | |
|---|---|---|---|
| | Anti-Her2(T)-Fc1-D1-Fc2 | Hu5F9-G4 | Trastuzumab |
| Maximum average fluorescence intensity | 3465348.00 | 213251.50 | 1841783.00 |
| EC50 (nM) | 10.03 | 0.4557 | 3.204 |

For example, as shown in FIG. 8B and Table 5, the anti-Her2 antibody Trastuzumab and the anti-CD47 antibody Hu5F9-G4 are both capable of specifically binding to SKBR-3 cells, but their maximum average fluorescence intensities are not identical to each other; meanwhile, Anti-Her2(T)-Fc1-D1-Fc2 is also capable of binding to SKBR-3 cells and has a higher maximum average fluorescence intensity, indicating that under the enviromnent of a same supersaturated protein concentration, the number of Anti-Her2(T)-Fc1-D1-Fc2 molecules specifically binding to SKBR-3 cells is significantly greater than that of the anti-Her2 antibody Trastuzumab or the anti-CD47 antibody Hu5F9-G4 molecules, and greater than the sum of the anti-Her2 antibody Trastuzumab and the anti-CD47 antibody Hu5F9-G4 molecules.

As known to those skilled in the art, the above test results indicate that the recombinant proteins of the present disclosure, which are capable of simultaneously binding to both the tumor-targeting antigen and CD47, can bind more to tumor cells and thus provide a more significant anti-tumor effect, compared with the concomitant use of the anti-CD47 antibody or SIRPα D1-Fc with another tumor-targeting therapeutic antibody.

Determination of Bispecific Binding Activity to the Targets EGFR and CD47 by Flow Cytometry Well-grown A431 cells (human epidermal cancer cell, purchased from the Institute of Basic Medical Sciences, Chinese Academy of Medical Sciences) were collected and counted, centrifuged and resuspended to a concentration of $2 \times 10^6$ cells/mL with PBS+2% FBS. 100 μL of the cell suspension was aliquoted to each of a 96-well U-plate (Art No. 3799, Corning) and allowed to stand for at least 15 minutes. The supernatant was pipetted and discarded after centrifugation, then 11 serial dilutions of Anti-EGFR-Fc1-D1-Fc2, JMT101, SIRPα D1-Fc or Hu5F9-G4 (4-fold serial dilutions starting from 216.6 nM, a total of 11 dilutions) were added respectively and incubated at 4° C. for 1 hour. After rinsing with PBS+2% FBS, goat anti-human IgG Fc-FITC (F9512-2ML, Sigma) was added and incubated for 1 hour at 4° C. After rinsing and resuspension with PBS+2% FBS, the fluorescence value was determined by a flow cytometer (Accuri C6, BD).

Since the surface of A431 cells simultaneously expresses EGFR and CD47 antigens, the anti-EGER antibody JMT101, the anti-CD47 antibody Hu5F9-G4 and SIRPα D1-Fc are all capable of specifically binding to A431 cells, but their maximum average fluorescence intensities are various.

The test results showed that Anti-EGFR-Fc1-D1-Fc2, Anti-EGFR-Fc1-D1'''-Fc2, Anti-EGFR-Fc1-D1-D2-Fc2, Anti-EGFR-Fc1-D1'''-D2-Fc2 and Anti-EGFR-Fc1-D1-D2-D3-Fe2 were all capable of binding to A431 cells, and achieved a higher maximum average fluorescence intensity.

The above test results demonstrate that the recombinant proteins of the present disclosure are capable of specifically binding to tumor cells and exhibit a significant advantage in the number of molecules under the environment of a same supersaturated protein concentration, compared with the anti-EGFR antibody JMT101 and/or the anti-CD47 antibody Hu5F9-G4 and/or SIRPα D1-Fc. Preferably, the saturation binding abundance of the recombinant proteins of the present disclosure to tumor cells is greater than the sum of the saturation binding abundance of the corresponding anti-EGFR antibody and SIRPα D1-Fc to tumor cells under the environment of a same supersaturated protein concentration.

TABLE 6

Maximum average fluorescence intensity and $EC_{50}$ (nM) of the binding of antibodies/recombinant proteins to A431 cells

| | Sample | | | |
|---|---|---|---|---|
| | JMT101 | Anti-EGFR-Fc1-D1-Fc2 | Hu5F9-G4 | SIRPα D1-Fc |
| Maximum average fluorescence intensity | 901868 | 1511274 | 686658 | 429788 |
| $EC_{50}$ (nM) | 0.598 | 1.217 | 0.865 | 3.677 |

For example, as shown in FIG. 8C and Table 6, the anti-EGFR antibody JMT101, the anti-CD47 antibody Hu5F9-G4 and SIRPα D1-Fc are all capable of specifically binding to A431 cells, but their maximum average fluorescence intensities are not identical to each other; and the $EC_{50}$ (JMT101)=0.598 nM, $EC_{50}$ (SIRPα D1-Fc)=3.677 nM, $EC_{50}$ (Hu5F9-G4)=0.865 nM. It can be seen that the binding affinity of JMT101 to A431 cells is more than 6-fold of the binding affinity of SIRPα D1-Fc to A431 cells. Meanwhile, Anti-EGFR-Fc1-D1-Fc2 is also capable of binding to A431 cells and has a higher maximum average fluorescence intensity, indicating that under the condition of a same supersaturated protein concentration, the number of Anti-EGFR-Fc1-D1-Fc2 molecules specifically binding to A431 cells is significantly greater than that of the anti-EGFR antibody JMT101 or SIRPα D1-Fcor the anti-CD47 antibody Hu5F9-G4 molecules, and also greater than the sum of the anti-EGFR antibody JMT101 and SIRPα D1-Fc molecules.

As known to those skilled in the art, the above test results indicate that the recombinant proteins of the present disclosure, which are capable of simultaneously binding to both the tumor-targeting antigen and CD47, can bind more to tumor cells and thus provide a more significant anti-tumor effect, compared with the concomitant use of the anti-CD47 antibody or SIKPα D1-Pc with another tumor-targeting therapeutic antibody.

Determination of Bispecific Binding Activity to the Targets PD-L1 and CD47 by Flow Cytometry $2 \times 10^7$ NCI-H441 cells (human lung adenocarcinoma cell, purchased from BeinaChuanglian Biotechnology Research Institute Co., Ltd, Beijing) were stimulated with 10 ng/mL, hIFN-γ (BD, Art No. 554616), then digested, collected, counted, centrifuged and resuspended to a concentration of $3 \times 10^6$ cells/mL with PBS+2% FBS. 100 μL of the cell suspension was aliquoted to each well of a 96-well U-plate (Art No. 3799, Corning) and allowed to stand for at least 15 minutes. The supernatant was pipetted and discarded after centrifugation, then 12 serial dilutions of Anti-PD-L1(Ate)-Fc1-D1-Fc2 or Atezolizumab (433.2 nM, 21.6.6 nM, 4-fold serial dilutions starting from 216.6 nM, a total of 12 concentrations) were added respectively and incubated at 4° C. for 1 hour. After rinsing with PBS+2% FBS, goat anti-human IgG Fc-FITC (F9512-2ML, Sigma) was added and incubated for 1 hour at 4° C. After rinsing and resuspension with PBS+2% FBS, the fluorescence value was determined by a flow cytometer (Accuri C6, BD).

Since the surface of NCI-H441 cells simultaneously expresses PD-L1 and CD47 antigens, the anti-PD-L1 antibodies Atezolizumab, 13G4, 12A4, the anti-CD47 antibody Hu5F9-G4, SIRPαD1-Fc are all capable of specifically binding to NCI-H441cellsl.

The test results showed that Anti-PD-L1(Ate)-Fc1-D1-Fc2, Anti-PD-L1(Ate)-Fc1-D1‴-Fc2, Anti-PD-L1(Ate)-Fc1-D1-D2-Fc2, Anti-PD-L1(Ate)-Fc1-D1‴-D2-Fc2, Anti-PD-L1(Ate)-Fc1-D1-D2-D3-Fc2, Anti-PD-L1(13G4)-Fc1-D1-Fc2, Anti-PD-L1(13G4)-Fc1-D1‴-Fc2, Anti-PD-L1(13G4)-Fc1-D1-D2-Fc2, Anti-PD-L1(13G4)-Fc1-D1‴-D2-Fc2, Anti-PD-L1(13G4)-Fc1-D1-D2-D3-Fc2, Anti-PD-L1(12A4)-Fc1-D1-Fc2, Anti-PD-L1(12A4)-Fc1-D1‴-Fc2, Anti-PD-L1 (12A4)-Fc1-D1-D2-Fc2, Anti-PD-L1(12A4)-Fc1-D1‴-D2-Fc2 and Anti-PD-L1(12A4)-Fc1-D1-D2-D3-Fc2 were all capable of binding to NCI-H441 cells, and achieved a higher maximum average fluorescence intensity.

The above test results demonstrate that the recombinant proteins of the present disclosure, compared with the anti-PD-L1 antibodies Atezolizumab, 13G4 and 12A4, are capable of specifically binding to tumor cells and exhibit a significant advantage in the number of molecules under the condition of a same supersaturated protein concentration. For example, under the environment of a same supersaturated protein concentration, the recombinant proteins of the present disclosure binds more to tumor cells and exhibits a significant advantage in the number of molecules than the anti-PD-L1 antibody Atezolizumab.

TABLE 7

Maximum average fluorescence intensity and $EC_{50}$ (nM) of the binding of antibodies/recombinant proteins to NCI-H441 cells

| | Sample | | | |
|---|---|---|---|---|
| | Anti-PD-L1(Ate)-Fc1-D1-Fc2 | Atezolizumab | Hu5F9-G4 | SIRPα D1-Fc |
| Maximum average fluorescence intensity | 156541 | 64038 | 100973 | 83200 |
| EC50 (nM) | 1.565 | 0.2006 | 0.3865 | 1.643 |

For example, as shown in FIG. 8D and Table 7, the anti-PD-L1 antibody Atezolizumab is capable of specifically binding to NCI-H441 cells; meanwhile, Anti-PD-L1(Ate)-Fc1-D1-Fc2 is also capable of binding to NCI-H441 cells and has a higher maximum average fluorescence intensity, indicating that under the environment of a same supersaturated protein concentration, the number of Anti-PD-L1 (Ate)-Fc1-D1-Fc2 molecules specifically binding to NCI-H441 cells is significantly greater than that of the anti-PD-L1 antibody Atezolizumab molecules. $EC_{50}$ (Atezolizumab) =0.2006 nM, $EC_{50}$ (SIRPα D1-Fc)=1.643 nM, $EC_{50}$ (Hu5F9-G4)=0.3865 nM. It can be seen that the binding affinity of Atezolizumab to NCI-H441 cells is more than 6-fold of the binding affinity of SIRPα D1-Fc to NCI-H441 cells.

As known to those skilled in the art, the above test results indicate that the recombinant proteins of the present disclosure, which are capable of simultaneously binding to both the tumor-targeting antigen and CD47, can bind more to tumor cells and thus provide a more significant anti-tumor effect, compared with the concomitant use of the anti-CD47 antibody or SIRPα D1-Fc with another tumor-targeting therapeutic antibody.

2. Determination of competitive binding activity to the target

The following method takes Ofa-Fc1-D1-Fc2 or Anti-EGFR-Fc1-D1-Fc2 as an example, using ELISA to determine the competitive binding activity to the targets CD47 and SIRPα.

Determination of Competitive Binding Activity of Ofa-Fc1-D1-Fc2 and Anti-EGFR-Fc1-D1-Fc2 by ELISA An ELISA plate (9018, Corning) was coated with 100 μL of 1 μg/mL CD47-4-His (12283-H08H-200, Sino Biological) and placed at 4° C. overnight. The plate was washed with PBST, and then blocked with PBS+1% BSA for 2 hours at room temperature. After rinsing, 100 μL of a mixture of diluted Ofa-Fc1-D1-Fc2 or Anti-EGFR-Fc1-D1-Fc2 (3-fold serial dilutions starting from 1000 ng/mL, a total of 11 dilutions) and biotin-labeled SIRPα D1-Fc (Biotin Labeling Kit, 21925, Thermo, the concentration for adding was 100 ng/mL) was aliquoted to each well of the coated plate, then incubated for 1 hour at 25° C. After discarding the sample and rinsing the plate three times with PBST solution, 100 μL of diluted streptavidin-HRP (1:10000) (ML-0437P-HRP, ZI501-1, Yanyu Chemical Reagent Co., Ltd) was added, then incubated at 25° C. for 1 hour. After discarding the solution and rinsing the plate three times with PBST solution, TMB (P0209, beyotime) was added, and the plate was developed for about 20 minutes and placed away from light. The reaction was stopped with $H_2SO_4$, and the OD value at 450-650 nm was read on a microplate reader.

The test results showed that the anti-CD47 antibodies Hu5F9-G4, SIRPα D1-Fc, Ofa-Fc1-D1-Fc2, Ofa-Fc1-D1-D2-Fc2, Ofa-Pc1-D1-D2-D3-Fc2, Obi-Fc1-D1-Fc2, Obi-Fc1-D1-D2-Fc2, Obi-Fc1-D1-D2-D3-Fc2, Anti-EGFR-Fc1-D1-Fc2, Anti-EGFR-Fc1-D1-D2-Fc2, Anti-EGFR-Fc1-D1-D2-D3-Fc2, Anti-Her2(P)-Fc1-D1-Fc2, Anti-Her2(P)-Fc1-D1-D2-Fc2, Anti-Her2(P)-Fc1-D1-D2-D3-Fc2, Anti-Her2(T)-Fc1-D1-Fc2, Anti-Her2(T)-Fc1-D1-D2-Fc2, Anti-Her2(T)-Fc1-D1-D2-D3-Fc2, Anti-EGFR-Fc1-D1-Fc2, Anti-EGFR-Fc1-D1-D2-Fc2, Anti-EGFR-Fc1-D1-D2-D3-Fc2, Anti-PD-L1(Ate)-Fc1-D1-Fc2, Anti-PD-L1(Ate)-Fc1-D1-D2-Fc2, Anti-PD-1-1(Ate)-Fc1-D1-D2-D3-Fc2, Anti-PD-L1(13G4)-Fc1-D1-Fc2, Anti-PD-L1 (13G4)-Fc1-D1-D2-Fc2, Anti-PD-L1(13G4)-Fc1-D1-D2-D3-Fc2, Anti-PD-L1 (12A4)-Fc1-D1-Fc2, Anti-PD-L1(12A4)-Fc1-D1-D2-Fc2 and Anti-PD-L1(12A4)-Fc1-D1-D2-D3-Fc2 were all capable of competing with the biotin-labeled SIRPα D1-Fc to bind to the CD47 antigen at different degrees, exerting competitive binding activity.

Figure 9:
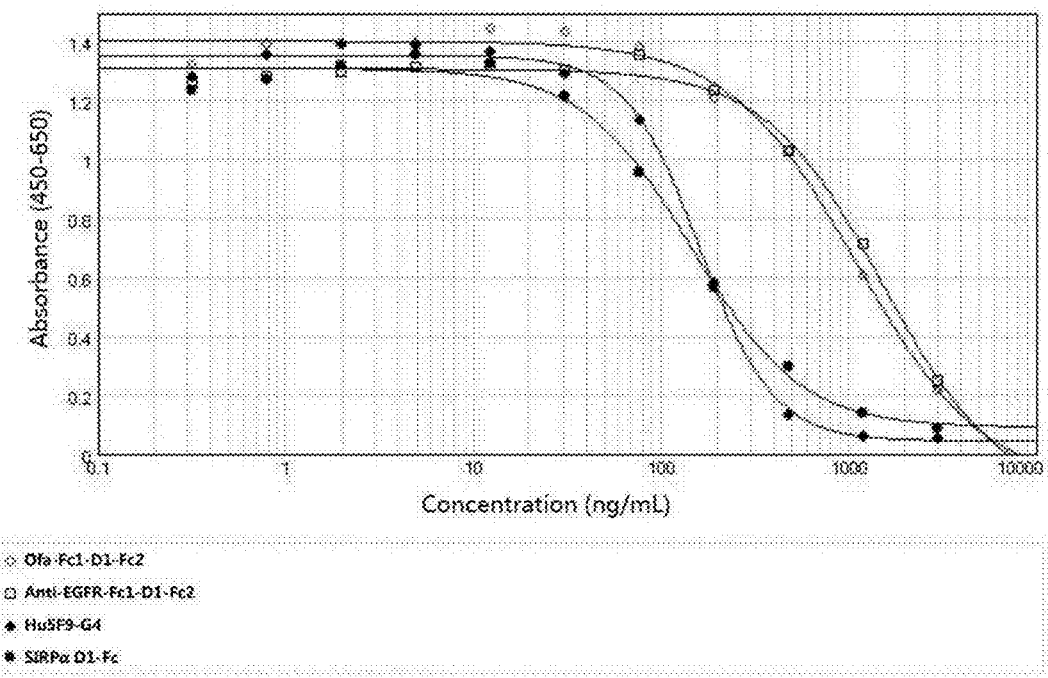
FIG. 9 shows the ELISA results of the competitive binding of the recombinant proteins of the present disclosure to SICRα D1-Fc and anti-CD47 antibodies against CD47.

For example, as shown in FIG. 9, the anti-CD47 antibodies Hu5F9-G4, SIRPα D1-Fc, OFa-Fc1-D1-Fc2, and Anti-EGFR-Fc1-D1-Fc2 are all capable of competing with the biotin-labeled SIRPα D1-Fc to bind to the CD47 antigen, exerting competitive binding activity; the competitive binding ability of Ofa-Fc1-D1-Fc2 or Anti-EGFR-Fc1-D1-Fc2 to CD47 is weaker than that of the anti-CD47 antibody Hu5F9-G4 or SIRPα D1-Fc, respectively, which is consistent with the results of the affinity studies described in the above examples.

EXAMPLE 4

Early Immunological Safety Evaluation of Recombinant Proteins in Vitro

Early immunological safety study of the recombinant proteins Ofa-Fc1-D1'''-Fc2, Ofa-Fc1-D1'''-D2-Fc2, Anti-EGFR-Fc1-D1'''-Fc2, Anti-EGFR-Fc1-D1'''-D2-Fc2, Anti-Her2(T)-Fc1-D1'''-Fc2, Anti-Her2(T)-Fc1-D1'''-D2-Fc2, Anti-Her2(P)-Fc1-D1'''-Fc2, Anti-Her2(P)-Fc1-D1'''-D2-Fc2, Anti-PD-L1(Ate)-Fc1-D1'''-Fc2, Anti-PD-L1(Ate)-Fc1-D1'''-D2-Fc2, Anti-PD-L1(13G4)-Fc1-D1'''-Fc2, Anti-PD-L1(13G4)-Fc1-D1'''-D2-Fc2, Anti-PD-L1(12A4)-Fc1-D1'''-Fc2 and Anti-PD-L1(12A4)-Fc1-D1'''-D2-Fc2 were conducted respectively in vitro. Taking Ofa-Fc1-D1'''-Fc2 as an example, the following method is suitable for the recombinant proteins comprising a high affinity mutant of the extracellular truncated variant of SIRPa in the right arm.

Early immunological safety study of the recombinant proteins Ofa-Fc1-D1-Fc2, Ofa-Fc1-D1-D2-Fc2, Ofa-Fc1-D1-D2-D3-Fc2, Obi-Fc1-D1-Fc2, Obi-Fc1-D1-D2-Fc2, Obi-Fc1-D1-D2-D3-Fc2, Anti-EGFR-Fc1-D1-Fc2, Anti-EGFR-Fc1-D1-D2-Fc2, Anti-EGFR-Fc-D1-D2-D3-Fc2, Anti-Her2(P)-Fc1-D1-Fc2, Anti-Her2(P)-Fc1-D1-D2-Fc2, Anti-Her2(P)-Fc1-D1-D2-D3-Fc2, Anti-Her2(T)-Fc1-D1-Fc2, Anti-Her2(T)-Fc1-D1-D2-Fc2, Anti-Her2(T)-Fc1-D1-D2-D3-Fc2, Anti-EGFR-Fc1-D1-Fc2, Anti-EGFR-Fc1-D1-D2-Fc2, Anti-EGFR-Fc1-D1-D2-D3-Fc2, Anti-PD-L1(Ate)-Fc1-D1-D2-Fc2, Anti-PD-L1(Ate)-Fc1-D1-D2-Fc2, Anti-PD-L1(Ate)-Fc1-D1-D2-D3-Fe2, Anti-PD-L1(13G4)-Fc1-D1-Fc2, Anti-PD-L1(13G4)-Fc1-D1-D2-Fc2, Anti-PD-L1(13G4)-Fc1-D1-D2-D3-Fc2, Anti-PD-L1(12A4)-Fc1-D1-Fc2, Anti-PD-L1 (12A4)-Fc1-D1-D2-Fc2 and Anti-PD-L1(12A4)-Fc1-D1-D2-D3-Fc2 were conducted respectively in vitro. Taking Ofa-Fc1-D1-Fc2 as an example, the following method is suitable for the recombinant proteins comprising an extracellular truncated variant of SIRPα in the tight arm.

Determination of Specific Binding of Bispecific Antibodies to the Target CD47 before and after Mutation in the Right Arm by Flow Cytometry NCI-H441 cells (human lung adenocarcinoma cell, purchased from BeinaChuanglian Biotechnology Research Institute Co., Ltd, Beijing) were digested, collected, counted, centrifuged and then resuspended to a concentration of $3\times10^6$ cells/mL with PBS+2% FBS. 100 μL of the cell suspension was aliquoted to each well of a 96-well U-plate (Art No. 3799, Corning) and allowed to stand for at least 15 minutes. The supernatant was pipetted and discarded after centrifugation, then 12 serial dilutions of Ofa-Fc1-D1-Fc2, Ofa-Fc1-D1'''-Fc2, Hu5F9-G4 or Ofatutnutnab (433.2 nM, 216.6 nM, 4-fold serial dilutions starting from 216.6 nM, with a total of 12 concentrations) were added respectively and incubated at 4° C. for 1 hour. After rinsing with PBS+2% FBS, goat anti-human IgG Fe-FITC (F9512-2ML, Sigma) was added and incubated for 1 hour at 4° C. After rinsing and resuspension with PBS+2% FBS, the fluorescence value was determined by a flow cytometer (Accuri C6, BD).

TABLE 8

Specific binding of bispecific antibodies to the target CD47 before and after mutation in the right arm by flow cytometry

| | Sample | | | |
|---|---|---|---|---|
| | Ofa-Fc1-D1-Fc2 | Ofa-Fc1-D1m-Fc2 | Hu5F9-G4 | Ofatumumab |
| Maximum average fluorescence intensity | 172944.90 | 272734.80 | 120133.40 | 3497.17 |
| $EC_{50}$ (nM) | 8.680 | 0.5292 | 0.2861 | NA |

Figure 10:
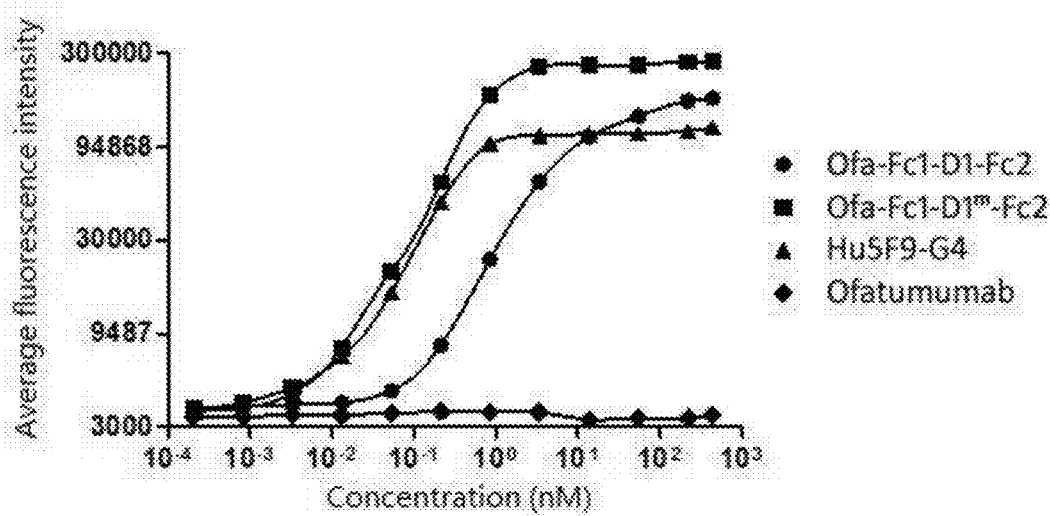
FIG. 10 shows the flow cytometry results of the binding affinity of the recombinant proteins of the present disclosure and its high affinity variants to CD47, anti-CD47 antibodies and anti-CD20 antibodies to human CD47.

For example, as shown in FIG. 10 and Table 8, except that the anti-CD20 antibody Ofatumumab is not capable of binding to CD47, the anti-CD47 antibodies Hu5F9-G4, Ofa-Fc1-D1-Fc2 and Ofa-Fc1-D1'''-Fc2 are all capable of binding to CD47, and the binding affinity of Ofa-Fc1-D1'''-Fc2 ($EC_{50}$=0.529 nM) to NCI-H441 cells is higher than that of Ofa-Fc1-D1-Fc2 ($EC_{50}$=8.68 nM), wherein D1''' is a high affinity mutant in the D1 region of SIRPα(i.e., Seq ID No: 10 in CN106519036A).

Early in Vitro Immunological Safety Evaluation Assay of Recombinant Proteins (1) Preparation of Human Effector Cell Suspension:

Well-grown human NK92MI-CD16a effector cells with a stable and high expression of CD16a (purchased from Huabo Biotech Co., Ltd) were centrifuged (201 g, 5 min) to discard the supernatant, and resuspended in 5 mL MEM (free of phenol red) basal medium (purchased from Gibco, 51200-038). After counting, the cell suspension was adjusted to a cell density of $2.4\times10^6$ cells/mL with MEM (free of phenol red) basal medium, which was used as a human effector cell suspension.

(2) Incubation of Effector Cells and Antibodies:

50 μL MEM (free of phenol red) basal medium was aliquoted into each well of a 96-well clear bottom black plate, then 25 μL of every dilution of Ofa-Fc1-D1-Fc2 or Ofa-Fc1-D1'''-Fc2 bispecific antibody was aliquoted into each well of the plate respectively in duplicate. 25 μL of the human effector cell suspension prepared in step (1) was added (60000 cells/well). After mixing thoroughly, the Ofa-Fc1-D1-Fc2 or Ofa-Fc1-D1'''-Fc2 bispecific antibody had final serial concentration (4-fold serial dilutions starting from 433.2 nM, a total of 10 dilutions). The mixture was allowed to react at 37° C. for 5.5 hours, then lysis buffer (derived from Promega kit, G7891) was added to the control group and incubated for 0.5 hour.

(3) Detection of ADCC Activity:

After incubation, the uncovered plate was placed in a safety cabinet and naturally cooled to room temperature for approximately 15 minutes. 100 μL of LDH substrate reaction solution (derived from Promega kit, 67891) equilibrated at room temperature for 30 minutes was aliquoted to each well of the plate, mixed gently and then incubated for 15 minutes at room temperature. 50 μL of stop solution (derived from Promega kit, G7891) was immediately added to each well and mixed thoroughly, then the fluorescence value was determined on a microplate reader.

The test results showed that the ADCC positive recombinant proteins and/or antibodies targeting CD47 resulted in mutual killing of NK cells due to the expression of CD47 antigen on NK cells. Therefore, compared to Ofa-Fc1-D1'''-Fc2 or Ofa-Fc1-D1'''-D2-Fc2 or Anti-EGFR-Fc1-D1'''-Fc2 or Anti-EGFR-Fc1-D1'''-D2-Fc2 or Anti-Her2(T)-Fc1-D1'''-Fc2 or Anti-Her2(T)-Fc1-D1'''-D2-Fc2 or Anti-Her2(P)-Fc1-D1'''-Fc2 or Anti-Her2(P)-Fc1-D1'''-D2-Fc2 or Anti-PD-L1(Ate)-Fc1-D1'''-Fc2 or Anti-PD-L1(Ate)-Fc1-D1'''-D2-Fc2 or Anti-PD-L1(13G4)-Fc1-D1'''-Fc2 or Anti-PD-L1(13G4)-Fc1-D1'''-D2-Fc2 or Anti-PD-L1(12A4)-Fc1-D1'''-Fc2 or Anti-PD-L1 (12A4)-Fc1-D1'''-D2-Fc2, each of which comprised a high affinity mutant of the extracellular truncated variant of SIRPα, the recombinant protein Ofa-Fc1-D1-Fc2 or Ofa-Fc1-D1-D2-Fc2 or Ofa-Fc1-D1-D2-D3-Fc2 or Obi-Fc1-D1-Fc2 or Obi-Fc1-D1-D2-Fc2 or Obi-Fc1-D1-D2-D3-Fc2 or Anti-EGFR-Fc1-D1-Fc2 or Anti-EGFR-Fc1-D1-D2-Fc2 or Anti-EGER-Fc1-D1-D2-D3-Fc2 or Anti-Her2(P)-Fc1-D1-Fc2 or Anti-Her2(P)-Fc1-D1-D2-Fc2 or Anti-Her2(P)-Fc1-D1-D2-D3-Fc2 or Anti-Her2(T)-Fc1-D1-Fc2 or Anti-Her2(T)-Fc1-D1-D2-Fc2 or Anti-Her2(T)-Fc1-D1-D2-D3-Fc2 or Anti-EGFR-Fc1-D1-Fc2 or Anti-EGFR-Fc1-D1-D2-Fc2 or Anti-EGFR-Fc1-D1-D2-D3-Fc2 or Anti-PD-L1(Ate)-Fc1-D1-Fc2 or Anti-PD-L1(Ate)-Fc1-D1-D2-Fc2 or Anti-PD-L1(Ate)-Fc1-D1-D2-D3-Fc2 or Anti-PD-L1 (13G4)-Fc1-D1-Fc2 or Anti-PD-L1(13G4)-Fc1-D1-D2-Fc2 or Anti-PD-L1(13G4)-Fc1-D1-D2-D3-Fc2 or Anti-PD-L1 (12A4)-Fc1-D1-Fc2 or Anti-PD-L1(12A4)-Fc1-D1-D2-Fc2 or Anti-PD-L1(12A4)-Fc1-D1-D2-D3-Fc2 significantly reduced the toxic side effects caused by NK cells for at least 1000-fold, due to its weak affinity to the CD47.

Figure 11:
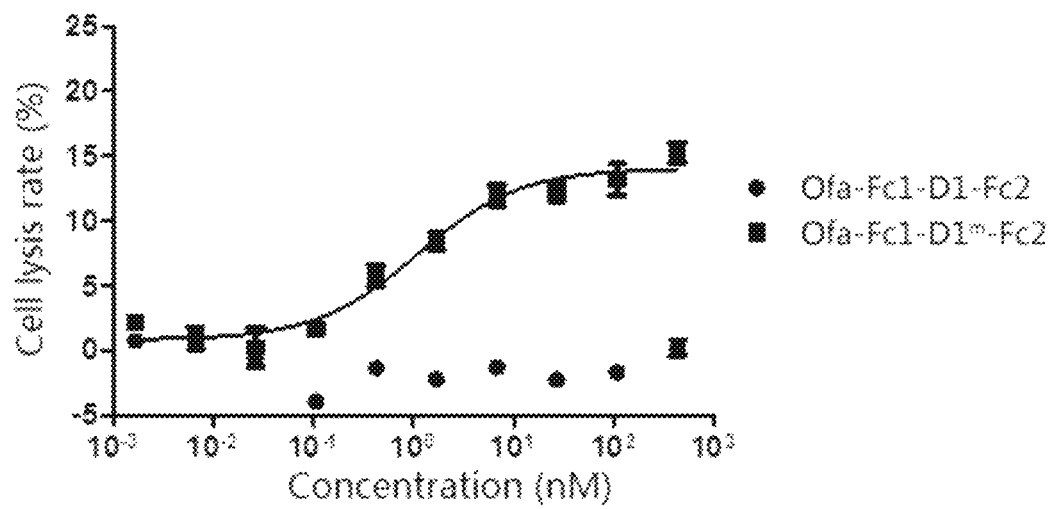
FIG. 11 shows the results of the immunological safety evaluation assay of the recombinant proteins of the present disclosure in vitro.

For example, as shown in FIG. 11, when the concentration of the antibody/recombinant protein reached $10^{-1}$ nm, cell lysis begins to occur and when the concentration of the antibody/recombinant protein reached $10^3$ nM, the rate of cell lysis reaches 15.25% in the Ofa-Fc1-D1'''-Fc2 treatment group, while no cell lysis is Observed in the Oba-Fc1-D1-Fc2 treatment group at a concentration of $10^3$ nM.

As known to those skilled in the art, the above test results indicate that the recombinant proteins of the present disclosure having ADCC activity and low affinity to the CD47 antigen have higher immunological safety.

As known to those skilled in the art, the above test results indicate that the optimized method for detecting ADCC activity (i.e., early immunological safety evaluation assay in vitro) described in the present disclosure can be used to evaluate the early immunological safety of recombinant proteins (including monovalent or multivalent) or antibodies (including monovalent or multivalent) targeting CD47 and having ADCC activity. The method is simple, fast and not limited by blood resources.

EXAMPLE 5

Inhibition of Tumor Cell Growth by Recombinant Protein in Vivo

Inhibition of tumor cell growth by recombinant proteins Ofa-Fa-D1-Fc2, Ofa-Fc1-D1-D2-Fc2, Ofa-Fc1-D1-D2-D3-Fc2, Obi-Fc1-D1-Fc2, Obi-Fc1-D1-D2-Fc2, Obi-Fc1-D1-D2-D3-Fc2, Anti-EGFR-Fc1-D1-Fc2, Anti-EGFR-Fc1-D1-D2-Fc2, Anti-EGFR-Fc1-D1-D2-D3-Fc2, Anti-Her2(P)-Fc1-D1-Fc2, Anti-Her2(P)-Fc1-D1-D2-Fc2, Anti-Her2(P)-Fc1-D1-D2-D3-Fc2, Anti-Her2(T)-Fc1-D1-Fc2, Anti-Her2(T)-Fc1-D1-D2-Fc2, Anti-Her2(T)-Fc1-D1-D2-D3-Fc2, Anti-EGFR-Fc1-D1-Fc2, Anti-EGFR-Fc1-D1-D2-Fc2; Anti-EGFR-Fc1-D1-D2-D3-Fc2, Anti-PD-L1(Ate)-Fc1-D1-Fc2, Anti-PD-L1(Ate)-Fc1-D1-D2-Fc2, Anti-PD-L1(Ate)-Fc1-D1-D2-D3-Fc2, Anti-PD-L1(13G4)-Fc1-D1-Fc2, Anti-PD-L1(13G4)-Fc1-D1-D2-Fc2, Anti-PD-L1 (13G4)-Fc1-D1-D2-D3-Fc2, Anti-PD-L1(12A4)-Fc1-D1-Fc2, Anti-PD-L1(12A4)-Fc1-D1-D2-Fc2, Anti-PD-L1 (12A4)-Fc1-D1-D2-D3-Fc2 were conducted respectively in vivo. Taking Ofa-Fc1-D1-Fc2 as an example, the following method is applicable for the detection of recombinant proteins comprising an extracellular truncated variant of SIRPα in the right arm.

Male NSG mice (purchased from Beijing Wino Co., Ltd) were subcutaneously inoculated with human B-cell lymphoma Raji cells. After the tumor volume reached 80 mm³ to 150 mm³, the mice were divided into the following 2 groups (6 mice per group, the mice were intraperitoneally injected with the given agents for each group): 1) vehicle control group (Tris-citrate, pH 6.5); 2) Ofa-Fc1-D1-Fc2 group (150 μg/mouse); twice a week for 2 weeks. Tumor growth was observed and the tumor volume was measured before administration (0 day), and on the $3^{rd}$ day, $5^{th}$ day, $7^{th}$ day, $10^{th}$ day, $12^{th}$ day, and $14^{th}$ day after administration, to evaluate the anti-tumor effect of Ofa-Fc1-D1-Fc2.

The test results showed that in the NSG mouse model subcutaneously transplanted with Raji lymphoma, the recombinant proteins Ofa-Fc1-D1-Fc2, Ofa-Fc1-D1-D2-Fc2, Ofa-Fc1-D1-D2-D3-Fc2, Obi-Fc1-D1-Fc2, Obi-Fc1-D1-D2-Fc2, Obi-Fc1-D1-D2-D3-Fc2, Anti-EGFR-Fc1-D1-Fc2, Anti-EGFR-Fc1-D1-D2-Fc2, Anti-EGFR-Fc1-D1-D2-D3-Fc2, Anti-Her2(P)-Fc1-D1-Fc2, Anti-Her2(P)-Fc1-D1-D2-Fc2, Anti-Her2(P)-Fc1-D1-D2-D3-Fc2, Anti-Her2(T)-Fc1-D1-Fc2, Anti-Her2(T)-Fc1-D1-D2-Fc2, Anti-Her2(T)-Fc1-D1-D2-D3-Fc2, Anti-EGFR-Fc1-D1-Fc2, Anti-EGFR-Fc1-D1-D2-Fc2, Anti-EGFR-Fc1-D1-D2-D3-Fc2, Anti-PD-L1(Ate)-Fc1-D1-Fc2, Anti-PD-L1(Ate)-Fc1-D1-D2-Fc2, Anti-PD-L1(Ate)-Fc1-D1-D2-D3-Fc2, Anti-PD-L1(13G4)-Fc1-D1-Fc2, Anti-PD-L1(13G4)-Fc1-D1-D2-Fc2, Anti-PD-L1 (13G4)-Fc1-D1-D2-D3-Fc2, Anti-PD-L1(12A4)-Fc1-D1-Fc2, Anti-PD-L1(12A4)-Fc1-D1-D2-Fc2 and Anti-PD-L1(12A4)-Fc1-D1-D2-D3-Fc2 blocked the CD47-SIRPα signaling pathway and thus activated targeted phagocytosis of macrophages and/or Antibody dependent cellular phagocytosis (ADCP) mediated by macrophages, thus exhibiting a significant tumor suppressive effect.

Figure 12:
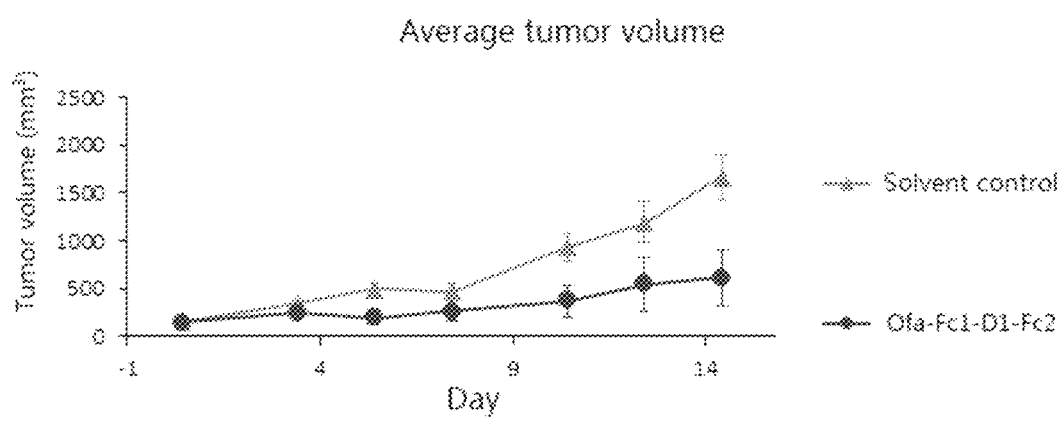
FIG. 12 shows the results of the pharmacodynamic assay of the recombinant proteins of the present disclosure on a NSG mouse model of subcutaneously transplanted Raji lymphoma.

For example, as shown in FIG. 12, the abscissa represents the time (days) from the NSG mice subcutaneously transplanted with Raji lymphoma receive drug treatment, and the ordinate represents the tumor volume (mm³). FIG. 12 shows that after a period of treatment with the drug Ofa-Fc1-D1-

Fc2, the Ofa-Fc1-D1-Fc2 group shows a significant tumor suppressive trend compared to the vehicle control group, and the tumor inhibition rate of the Ofa-Fc1-D1-Fc2 group on the 14$^{th}$ day reaches 63.14%.

As known to those skilled in the art, the above test results indicate that the recombinant proteins of the present disclosure which are capable of simultaneously binding to both the target antigen and the CD47 antigen on the tumor cells can achieve a significant tumor suppressing effect in the NSG mice subcutaneously transplanted with tumor cells.

EXAMPLE 6

Early Immunological Safety Evaluation Assay of Recombinant Proteins in Vitro

Early immunological safety evaluation of recombinant proteins Ofa-Fc1-D1′′′-Fc2, Ofa-Fc1-D1′′′-D2-Fc2, Anti-EGFR-Fc1-D1′′′-Fc2, Anti-EGFR-Fc1-D1′′′-D2-Fc2, Anti-Her2(T)-Fc1-D1′′′-Fc2, Anti-Her2(T)-Fc1-D1′′′-D2-Fc2, Anti-Her2(P)-Fc1-D1′′′-Fc2, Anti-Her2(P)-Fc1-D1′′′-D2-Fc2, Anti-PD-L1(Ate)-Fc1-D1′′′-Fc2, Anti-PD-L1(Ate)-Fc1-D1′′′-D2-Fc2, Anti-PD-L1(13G4)-Fc1-D1′′′-Fc2, Anti-PD-L1(13G4)-Fc1-D1′′′-D2-Fc2, Anti-PD-L1(12A4)-Fc1-D1′′′-Fc2 and Anti-PD-L1(12A4)-Fc1-D1′′′-D2-Fc2 were conducted respectively in vitro. Taking Ofa-Fc1-D1′′′-Fc2 as an example, the following method is applicable for the detection of recombinant proteins comprising a high affinity mutant of the extracellular truncated variant of SIRPct in the right arm.

Early immunological safety evaluation of recombinant proteins Ofa-Fc1-D1-Fc2, Ofa-Fc1-D1-D2-Fc2, Ofa-Fc1-D1-D2-D3-Fc2, Obi-Fc1-D1-D2-Fc2, Obi-Fc1-D1-D2-D3-Fc2, Anti-EGFR-Fc1-D1-Fc2, Anti-EGFR-Fc1-D1-D2-Fc2, Anti-EGFR-Fc1-D1-D2-D3-Fc2, Anti-Her2(P)-Fc1-D1-Fc2, Anti-Her2(P)-Fc1-D1-D2-Fc2, Anti-Her2(P)-Fc1-D1-D2-D3-Fc2, Anti-Her2(T)-Fc1-D1-Fc2, Anti-Her2(T)-Fc1-D1-D2-Fc2, Anti-Her2(T)-Fc1-D1-D2-D3-F2, Anti-EGFR-Fc1-D1-Fc2, Anti-EGER-Fc1-D1-D2-Fc2, Anti-EGFR-Fc1-D1-D2-D3-Fc2, Anti-PD-L1(Ate)-Fc1-D1-Fc2, Anti-PD-L1(Ate)-Fc1-D1-D2-Fc2, Anti-PD-L1(Ate)-Fc1-D1-D2-D3-Fc2, Anti-PD-L1(13G4)-Fc1-D1-Fc2, Anti-PD-L1(13G4)-Fc1-D1-D2-Fc2, Anti-PD-L1(13G4)-Fc1-D1-D2-D3-Fc2, Anti-PD-L1(12A4)-Fc1-D1-Fc2, Anti-PD-L1(12A4)-Fc1-D1-D2-Fe2 and Anti-PD-L1(12A4)-Fc1-D1-D2-D3-Fc2 were conducted respectively in vitro. Taking Ofa-Fc1-D1-Fc2 as an example, the following method is applicable for detection of recombinant proteins comprising an extracellular truncated variant of SIRPα in the right arm.

Since B cells highly express the CD20 antigen, this experiment evaluates the killing of tumor cells by determining the B cell content. In early immunological safety evaluation assay of recombinant proteins targeting another tumor antigen and the CD47 antigen in vitro, the experimental mice in this example should be subcutaneously transplanted with corresponding tumor cells.

Specific Tumor-Targeting Effect:

NSG (Hu-NSG) female mice (purchased from Beijing Idmo Co., Ltd) transplanted with human CD34+ HSC were selected and divided into the following 3 groups (3 mice for each group, the mice were intravenously injected with the given agents for each group): 1) 0.9% saline control group; 2) Hu5F9-G4 group (6.7 μg/mouse); 3) Ofa-Fc1-D1-Fc2 group (5 μg/mouse). The mice were administered once. At 96 hours after administration, 80 μL of blood was collected from the tail vein of the mice and added to an anticoagulant tube containing heparin sodium. The RBCs were lysed by a freshly prepared mixture of lysis buffer (BD Pharm Lyse™, Art No. 555899) and double distilled water in a volume ratio of 1:1, and the remaining cells were rinsed and resuspended with PBS+2% FBS, and then incubated with the fluorescent antibody (PE anti-human CD45 (Art No. 304039), FITC anti-human CD19 (Art No. 302206), APC anti-human CD3 (Art No. 300312), all purchased from BioLegend) for 30 minutes. After rinsing and resuspension with PBS+2% FBS, the sample was detected by a flow cytometer (Accuri™ C6, BD).

The test results showed that, when Hu-NSG mice were administrated with a same dose of Ofa-Fc1-D1-Fc2 or the anti-CD47 antibody Hu5F9-G4, at 96 hours after administration, Ofa-Fc1-D1-Fc2 preferentially cleared B cells expressing CD20 antigen (i.e., target cells), while the anti-CD47 antibody Hu5F9-G4 preferentially cleared non-target cells with high abundance of CD47 expression (such as T cells), due to its high affinity to the CD47 antigen.

Figure 13:
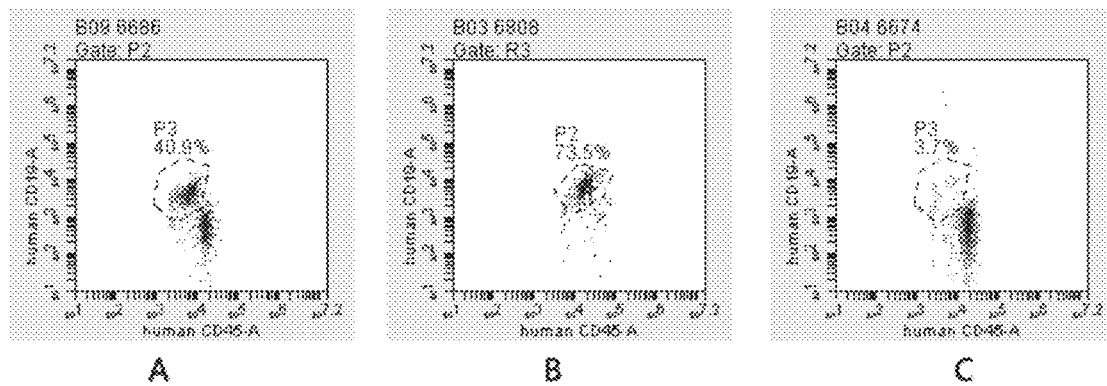
FIG. 13 shows the detection results of B cell content at 96 hours after treating the Hu-NSG mice with different samples at a same dose. Wherein, FIG. 13A corresponds to 0.9% physiological saline.

For example, as shown in FIG. 13, the anti-CD47 antibody Hu5F9-G4 group (FIG. 13B) shows a significant clearance of non-target cells with high abundance of CD47 expression (such as T cells) compared to 0.9% normal saline group (FIG. 13A) (the proportion of B cells (i.e., the target cells with CD20 antigen) in all detected cells increases from 40.9% to 73.5% at 96 hours after administration); whereas the recombinant protein Ofa-Fc1-D1-Fc2 group (FIG. 13C) shows a significant clearance of B cells (i.e., the target cells with the CD20 antigen) compared with 0.9% normal saline (FIG. 13A), i.e., Ofa-Fc1-D1-Fc2 preferentially clears B cells at 96 hours after administration (the proportion of B cells in all detected cells decreases from 40.9% to 3.7% at 96 hours after administration).

As known to those skilled in the art, the above test results indicate that the recombinant proteins of the present disclosure which are capable of simultaneously binding to both the tumor-targeting antigen and the CD47 antigen preferentially clear the cells and/or tumor cells with the tumor-targeting antigen under the condition of a same dose.

Immunological Safety at a Low Dose:

NSG (Hu-NSG) female mice (purchased from Beijing Idmo Co., Ltd) transplanted with human CD34+ HSC were selected and divided into the following 2 groups (3 mice for each group, the mice were intravenously injected with the given agents for each group): 1) Ofa-Fc1-D1-Fc2 group (1 μg/mouse); 3) Ofa-Fc1-D1′′′-Fc2 group (1 μg/mouse). The mice were administered once. At 72 hours after administration, 80 μL of blood was collected from the tail vein of the mice and added to an anticoagulant tube containing heparin sodium. The RBC's were lysed by a freshly prepared mixture of lysis buffer (BD Pharm Lyse™, Art No. 555899) and double distilled water at a volume ratio of 1:1, and the remaining cells were rinsed and resuspended with PBS+2% FBS, and then incubated with the fluorescent antibody (PE anti-human CD45 (Art No. 304039), FITC anti-human CD19 (Art No. 302206), APC anti-human CD3 (Art No. 300312), all purchased from BioLegend) for 30 minutes. After rinsing and resuspension with PBS+2% FBS, the sample of the Ofa-Fc1-D1-Fc2 group (1 μg/mouse) was detected by a flow cytometer (Accuri™ C6, BD), and the sample of the Ofa-Fc1-D1′′′-Fc2 group (1 μg/mouse) was detected by a flow cytometer (NovoCyte™ 3130, ACEA).

The test results showed that, in the case where the Hu-NSG mice were administrated with recombinant proteins at a low dose, at 72 hours after Ofa-Fc1-D1-Fc2, Ofa-Fc1-D1-D2-Fc2, Ofa-Fc1-D1-D2-D3-Fc2, Obi-Fc1-D1-Fc2, Obi-Fc1-D1-D2-Fc2, Obi-Fc1-D1-D2-D3-Fc2, Anti-EGFR-Fc1-D1-Fc2, Anti-EGFR-Fc1-D1-D2-Fa, Anti- EGFR-Fc1-D1-D2-D3-Fc2, Anti-Her2(P)-Fc1-D1-Fc2, Anti-Her2(P)-Fc1-D1-D2-Fc2, Anti-Her2(P)-Fc1-D1-D2-D3-Fc2, Anti-Her2(T)-Fc1-D1-Fc2, Anti-Her2(T)-Fc1-D1-D2-Fc2, Anti-Her2(T)-Fc1-D1-D2-D3-Fc2, Anti-EGFR-Fc1-D1-Fc2, Anti-EGFR-Fc1-D1-D2-Fc2, Anti-EGFR-Fc1-D1-D2-D3-Fc2, Anti-PD-L1(Ate)-Fc1-D1-Fc2, Anti-PD-L1(Ate)-Fc1-D1-D2-Fc2, Anti-PD-L1(Ate)-Fc1-D1-D2-D3-Fc2, Anti-PD-L1(13G4)-Fc1-D1-Fc2, Anti-PD-L1(13G4)-Fc1-D1-D2-Fc2, Anti-PD-L1 (13G4)-Fc1-D1-D2-D3-Fc2, Anti-PD-L1(12A4)-Fc1-D1-Fc2, Anti-PD-L1(12A4)-Fc1-D1-D2-Fc2 or Anti-PD-L1(12A4)-Fc1-D1-D2-D3-Fc2 was administrated once, the target cells which expressed the antigen targeted by the left arm (such as tumor cells) had been significantly eliminated, whereas the cells which do not express the antigen targeted by the left arm (such as T cells, other immune cells) had not been significantly affected; however, at 72 hours after the recombinant protein comprising a high affinity mutant of the extracellular truncated variant of SIRPα, Ofa-Fc1-D1'''-D2-Fc2 or Anti-EGFR-Fc1-D1'''-Fc2 or Anti-EGFR-Fc1-D1'''-D2-Fc2 or Anti-Her2(T)-Fc1-D1'''-Fc2 or Anti-Her2(T)-Fc1-D1'''-D2-Fc2 or Anti-Her2(P)-Fc1-D1'''-Fc2 or Anti-Her2(P)-Fc1-D1'''-D2-Fc2 or Anti-PD-L1(Ate)-Fc1-D1'''-Fc2 or Anti-PD-L1(Ate)-Fc1-D1'''-D2-Fc2 or Anti-PD-L1(13G4)-Fc1-D1'''-Fc2 or Anti-PD-L1(13G4)-Fc1-D1'''-D2-Fc2 or Anti-PD-L1(12A4)-Fc1-D1'''-Fc2 or Anti-PD-L1(12A4)-Fc1-D1'''-D2-Fc2 was administrated once, although the target cells which expressed the antigen targeted by the left arm (such as tumor cells) had been significantly eliminated, the cells which do not express the antigen targeted by the left arm (such as T cells and other immune cells) also had been eliminated to a significant extent.

Figure 14:
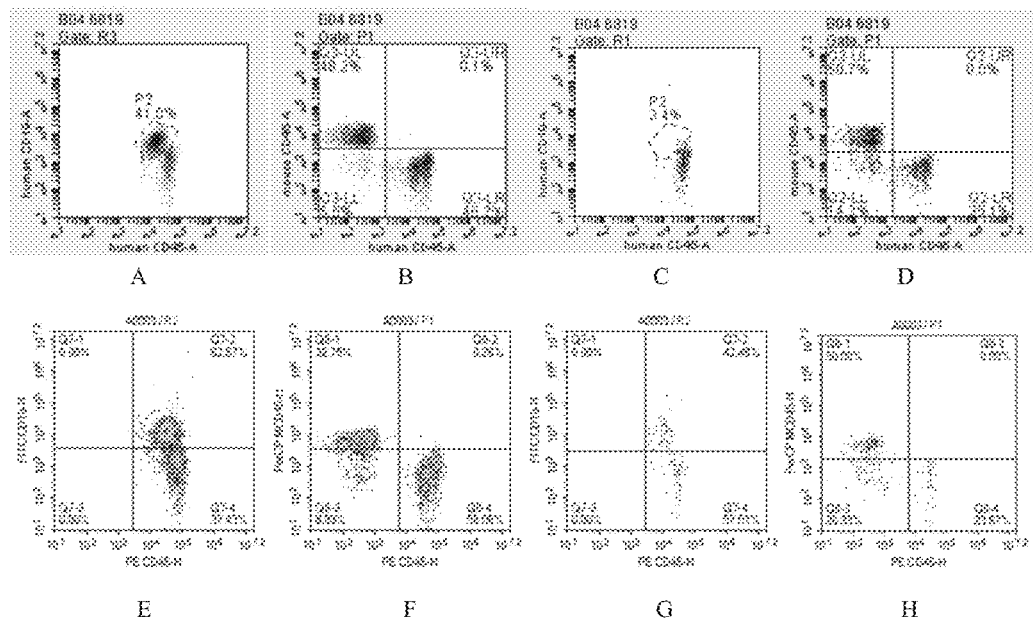
FIG. 14 shows the results of the early immunological safety evaluation assay of Ofa-Fc1-D1-Fc2 and Ofa-Fc1-D1m-Fc2 in Hu-NSG mice (FACS analysis of immune cell types) in vivo.

For example, as shown in FIG. 14, at 72 hours after the single administration of Ofa-Fc1-D1-Fc2B (FIG. 14C, FIG. 14D), the B cells (the target cell with the CD20 antigen) have been significantly eliminated (almost completely eliminated), while the cells that do not express the CD20 antigen (such as cells, other immune cells) have not been significantly affected, compared to the state before administration (FIG. 14A, FIG. 14B). At 72 hours after the single administration of Ofa-Fc1-D1'''-Fc2 (FIG. 14G, FIG. 14H), compared to the state before administration (FIG. 14E, FIG. 14F), although the B cells (the target cell with the CD20 antigen) have been significantly eliminated, the cells that do not express the CD20 antigen (such as T cells and other immune cells) also have been eliminated to a significant extent.

As known to those skilled in the art, the above results indicate that the recombinant proteins comprising an extracellular truncated variant of SIRPα in the right arm have a higher specific tumor-targeting effect and exhibit a greater immunological safety than the recombinant proteins comprising a high affinity mutant of the extracellular truncated variant of SIRPα in the right arm at a same dose.

Immune Recovery at a High Dose:

NSG (Hu-NSG) female mice (purchased from Beijing Idmo Co., Ltd) transplanted with human $CD34^+$ HSC were selected and divided into the following 2 groups (3 mice for each group, the mice were intravenously injected with the given agents for each group): 1) Hu5F9-G4 group (200 μg/mouse), 3) Ofa-Fc1-D1-Fc2 group (150 μg/mouse). The mice were administered once. At 4 days and 14 days after administration, 80 μL of blood was collected from the tail vein of the mice and added to an anticoagulant tube containing heparin sodium. The RBCs were lysed by a freshly prepared mixture of lysis buffer (BD Pharm Lyse™, Art No. 555899) and double distilled water in a volume ratio of 1:1, and the remaining cells were washed and resuspended with PBS+2% FBS, and then incubated with the fluorescent antibody (PE anti-human CD45 (Art No. 304039), FITC anti-human CD19 (Art No. 302206), APC anti-human CD3 (Art No. 300312), all purchased from BioLegend) for 30 minutes. After rinsing and resuspension with PBS+2% FBS, the sample was detected by a flow cytometer (Accuri™ C6, BD).

The test results showed that, in the case where the Hu-NSG mice were administrated with recombinant proteins at a high dose, at 96 hours after Ofa-Fc1-D1-Fc2, Ofa-Fc1-D1-D2-Fc2, Ofa-Fc1-D1-D2-D3-Fc2, Obi-Fc1-D1-Fc2, Obi-Fc1-D1-D2-Fc2, Obi-Fc1-D1-D2-D3-Fc2, Anti-EGFR-Fc1-D1-Fc2, Anti-EGFR-Fc1-D1-D2-Fc2, Anti-EGFR-Fc1-D1-D2-D3-Fc2, Anti-Her2(P)-Fc1-D1-Fc2, Anti-Her2(P)-Fc1-D1-D2-Fc2, Anti-Her2(P)-Fc1-D1-D2-D3-Fc2, Anti-Her2(T)-Fc1-D1-Fc2, Anti-Her2(T)-Fc1-D1-D2-Fc2, Anti-Her2(T)-Fc1-D1-D2-D3-Fc2, Anti-EGFR-Fc1-D1-Fc2, Anti-EGFR-Fc1-D1-D2-Fc2, Anti-EGFR-Fc1-D1-D2-D3-Fc2, Anti-PD-L1(Ate)-Fc1-D1-Fc2, Anti-PD-L1(Ate)-Fc1-D1-D2-Fc2, Anti-PD-L1(Ate)-Fc1-D1-D2-D3-Fc2, Anti-PD-L1(13G4)-Fc1-D1-Fc2, Anti-PD-L1(13G4)-Fc1-D1-D2-Fc2, Anti-PD-L1(13G4)-Fc1-D1-D2-D3-Fc2, Anti-PD-L1(12A4)-Fc1-D1-Fc2, Anti-PD-L1(12A4)-Fc1-D1-D2-Fc2, Anti-PD-L1(12A4)-Fc1-D1-D2-D3-Fc2 or anti-CD47 antibody Hu5F9-G4 was administrated once, the B cells (the target cell with the CD20 antigen) and the non-target cells (such as T cells, other immune cells) had been eliminated to a significant extent in each group. At 14 days after administration, in the Ofa-Fc1-D1-Fc2, Ofa-Fc1-D1-D2-Fc2, Ofa-Fc1-D1-D2-D3-Fc2, Obi-Fc1-D1-Fc2, Obi-Fc1-D1-D2-Fc2, Obi-Fc1-D1-D2-D3-Fc2, Anti-EGFR-Fc1-D1-Fc2, Anti-EGFR-Fc1-D1-D2-Fc2, Anti-EGFR-Fc1-D1-D2-D3-Fc2, Anti-Her2(P)-Fc1-D1-Fc2, Anti-Her2(P)-Fc1-D1-D2-Fc2, Anti-Her2(P)-Fc1-D1-D2-D3-Fc2, Anti-Her2(T)-Fc1-D1-Fc2, Anti-Her2(T)-Fc1-D1-D2-Fc2, Anti-Her2(T)-Fc1-D1-D2-D3-Fc2, Anti-EGFR-Fc1-D1-Fc2, Anti-EGFR-Fc1-D1-D2-Fc2, Anti-EGFR-Fc1-D1-D2-D3-Fc2, Anti-PD-L1(Ate)-Fc1-D1-Fc2, Anti-PD-L1(Ate)-Fc1-D1-D2-Fc2, Anti-PD-L1(Ate)-Fc1-D1-D2-D3-Fc2, Anti-PD-L1(13G4)-Fc1-D1-Fc2, Anti-PD-L1(13G4)-Fc1-D1-D2-Fc2, Anti-PD-L1(13G4)-Fc1-D1-D2-D3-Fc2, Anti-PD-L1(12A4)-Fc1-D1-Fc2, Anti-PD-L1(12A4)-Fc1-D1-D2-Fc2 or Anti-PD-L1(12A4)-Fc1-D1-D2-D3-Fc2 group, the B cells (the target cell with the CD20 antigen) were still in a state of being eliminated, while other non-target cells expressing the CD47 (such as T cells) had been significantly recovered; however in the anti-CD47 antibody Hu5F9-G4 group, neither the B cells (the target cell with the CD20 antigen) nor the non-target cells expressing the CD47 had been recovered.

Figure 15:
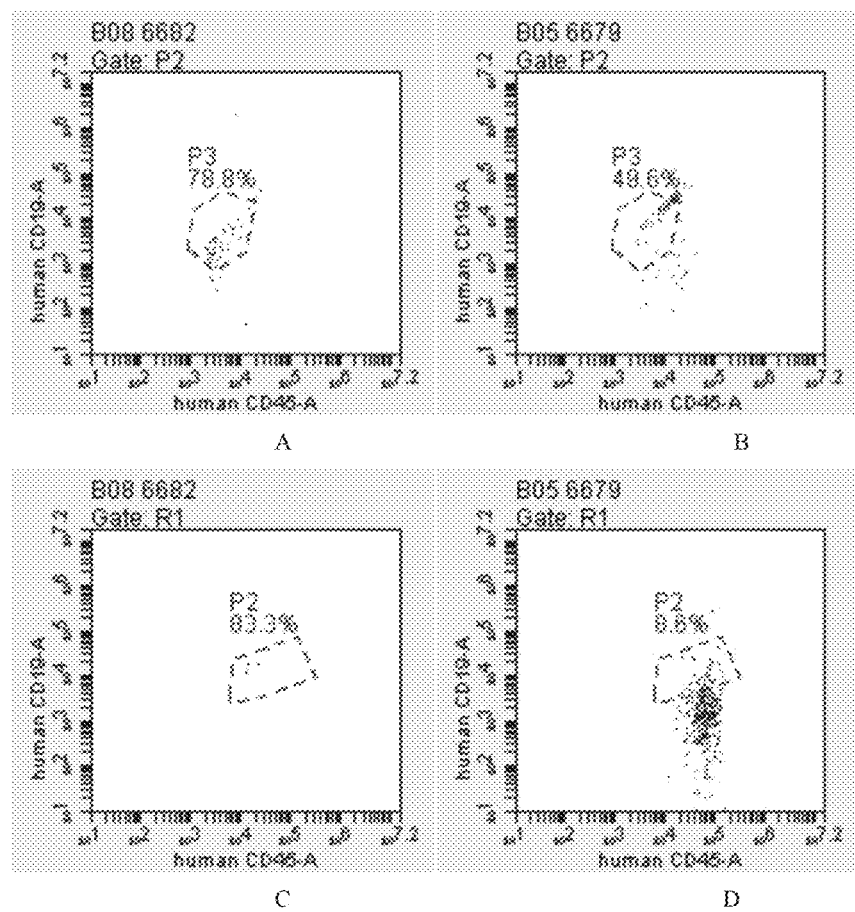
FIG. 15 shows the immunophenotyping FACS analysis at 96 hours after treating the Hu-NSG mice with different samples at a high dose.

For example, as shown in FIG. 15, at 96 hours after administration of a high dose of the anti-CD47 antibody Hu5F9-G4 (FIG. 15A) or Ofa-Fc1-D1-Fc2 (FIG. 15B), both the B cells (the target cell with the CD20 antigen) and the non-target cells expressing the CD47 (such as T cells) have been largely eliminated; but at 14 days after administration, the B cells (the target cell with the CD20 antigen) are still in a state of being eliminated, while the non-target cells expressing the CD47 (such as T cells) except of the B cells (the target cell with the CD20 antigen) have been significantly recovered in the Ofa-Fc1-D1-Fc2 group (FIG. 15D); however, neither the B cells (the target cell with the CD20 antigen) nor the non-target cells expressing the CD47 (such as T cells) do show a sign of recovery in the anti-CD47 antibody Hu5F9-G4 group (FIG. 15C).

As known to those skilled in the art, the above test results indicate that the recombinant proteins of the present disclosure which are capable of simultaneously binding to both the tumor-targeting antigen and the CD47 antigen have a higher immunological safety, since the non-target cells expressing CD47 (such as immune cells such as T cells) can be recovered under the treatment with a high dose of these recombinant proteins.

As known to those skilled in the art, the above test results indicate that the early immunological safety evaluation method in vitro described in the present disclosure can be used to evaluate the early immunological safety of recombinant proteins (including monovalent or multivalent) or antibodies (including monovalent or multivalent).

EXAMPLE 7

Influence of Different Truncations on the Binding Affinity to the Target

Among the recombinant proteins Ofa-Fc1-D1-Fc2, Ofa-Fc1-D1-D2-Fc2, Ofa-Fc1-D1-D2-D3-Fc2, Obi-Fc1-D1-Fc2, Obi-Fc1-D1-D2-Fc2, Obi-Fc1-D1-D2-D3-Fc2, Anti-EGFR-Fc1-D1-Fc2, Anti-EGFR-Fc1-D1-D2-Fc2, Anti-EGFR-Fc1-D1-D2-D3-Fc2, Anti-Her2(P)-Fc1-D1-Fc2, Anti-Her2(P)-Fc1-D1-D2-Fc2, Anti-Her2(P)-Fc1-D1-D2-D3-Fc2, Anti-Her2(T)-Fc1-D1-Fc2, Anti-Her2(T)-Fc1-D1-D2-Fc2, Anti-Her2(T)-Fc1-D1-D2-D3-Fc2, Anti-EGFR-Fc1-D1-Fc2, Anti-EGFR-Fc1-D1-D2-Fc2, Anti-EGFR-Fc1-D1-D2-D3-Fc2, Anti-PD-L1(Ate)-Fc1-D1-Fc2, Anti-PD-L1(Ate)-Fc1-D1-D2-Fc2, Anti-PD-L1(Ate)-Fc1-D1-D2-D3-Fc2, Anti-PD-L1(13G4)-Fc1-D1-Fc2, Anti-PD-L1(13G4)-Fc1-D1-D2-Fc2, Anti-PD-L1(13G4)-Fc1-D1-D2-D3-Fc2, Anti-PD-L1(12A4)-Fc1-D1-Fc2, Anti-PD-L1(12A4)-Fc1-D1-D2-Fc2 and Anti-PD-L1(12A4)-Fc1-D1-D2-D3-Fc2, Anti-Her2(T)-Fc1-D1-Fc2, Anti-Her2(T)-Fc1-D1-D2-Fc2, Anti-Her2(P)-Fc1-D1-Fc2 and Anti-Her2(P)-Fc1-D1-D2-Fc2 were taken as examples, and the following method is applicable for the recombinant proteins having a same left arm and a different length of extracellular truncated variants of SIRPα.

Determination of Bispecific Binding Activity to the Targets Her2 and CD47 by Flow Cytometry Well-grown SKBR-3 cells (human breast cancer cell, purchased from the Cell Bank of Chinese Academy of Sciences, Shanghai) were collected, counted, centrifuged and resuspended to a concentration of $2 \times 10^6$ cells/mL with PBS+2% FBS. 100 μL of the cell suspension was aliquoted to each well of a 96-well U-plate (Art No. 3799, Corning) and allowed to stand for at least 15 minutes. The supernatant was pipetted and discarded after centrifugation, then 11 serial dilutions of Anti-Her2(T)-Fc1-D1-Fc2, Anti-Her2(T)-Fc1-D1-D2-Fc2, Anti-Her2(P)-Fc1-D1-Fc2 or Anti-Her2(P)-Fc1-D1-D2-Fc2 (4-fold serial dilutions starting from 433.2 nM, a total of 11 dilutions) were added respectively and incubated at 4° C. for 1 hour. After rinsing with PBS+2% FBS, goat anti-human IgG Fc-FITC (F9512-2ML, Sigma) was added and incubated for 1 hour at 4° C. After rinsing and resuspension with PBS+2% FBS, the fluorescence value was determined by a flow cytometer (Accuri C6, BD).

Since Trastuzumab and Pertuzumab act on different epitopes of the Her2 antigen and there is a large difference in the distances from the two epitopes to the cell membrane, therefore, the recombinant proteins Anti-Her2(T)-Fc1-D1-Fc2, Anti-Her2(T)-Fc1-D1-D2-Fc2, Anti-Her2(P)-Fc1-D1-Fc2 and Anti-Her2(P)-Fc1-D1-D2-Fc2 are all capable of specifically binding to SKBR-3 cells, but their binding affinities and their maximum average fluorescence intensities are various.

The test results showed that, since Trastuzumab and Her2 epitopes (Pedersen M W, et al. Targeting Three Distinct HER2 Domains with a Recombinant Antibody Mixture Overcomes Trastuzumab Resistance. *Molecular Cancer Therapeutics*, 2015, 14(3): 669-680) are relatively closer to the cell membrane surface, Anti-Her2(T)-Fc1-D1-Fc2 had better affinity to the SKBR-3 cells than Anti-Her2(T)-Fc1-D1-D2-Fc2. Since Pertuzumab and Her2 epi topes (extracellular domain II of Her2) are relatively farther to the cell membrane surface, therefore Anti-Her2(P)-Fc1-D1-Fc2 had an equivalent affinity to the SKBR-3 cells compared to Anti-Her2(P)-Fc1-D1-D2-Fc2 SKBR-3.

The above test results demonstrate that the right arm with different lengths of truncation will affect the affinity of the recombinant proteins to the target cells. For the left arm which binds to the membrane-proximal epitope, the right arm with a shorter truncation of SIRPα can largely enhance the binding of the recombinant proteins to the two targets. However, for the left arm which binds to the membrane-distal epitope, the right arm with a shorter truncation of SIRPα would lose its advantage. The farther the antigen targeted by the left arm is distant from the cell membrane, the longer the truncated variant of SIRPα in the right arm should be in order to achieve optimal matching.

Figure 16:
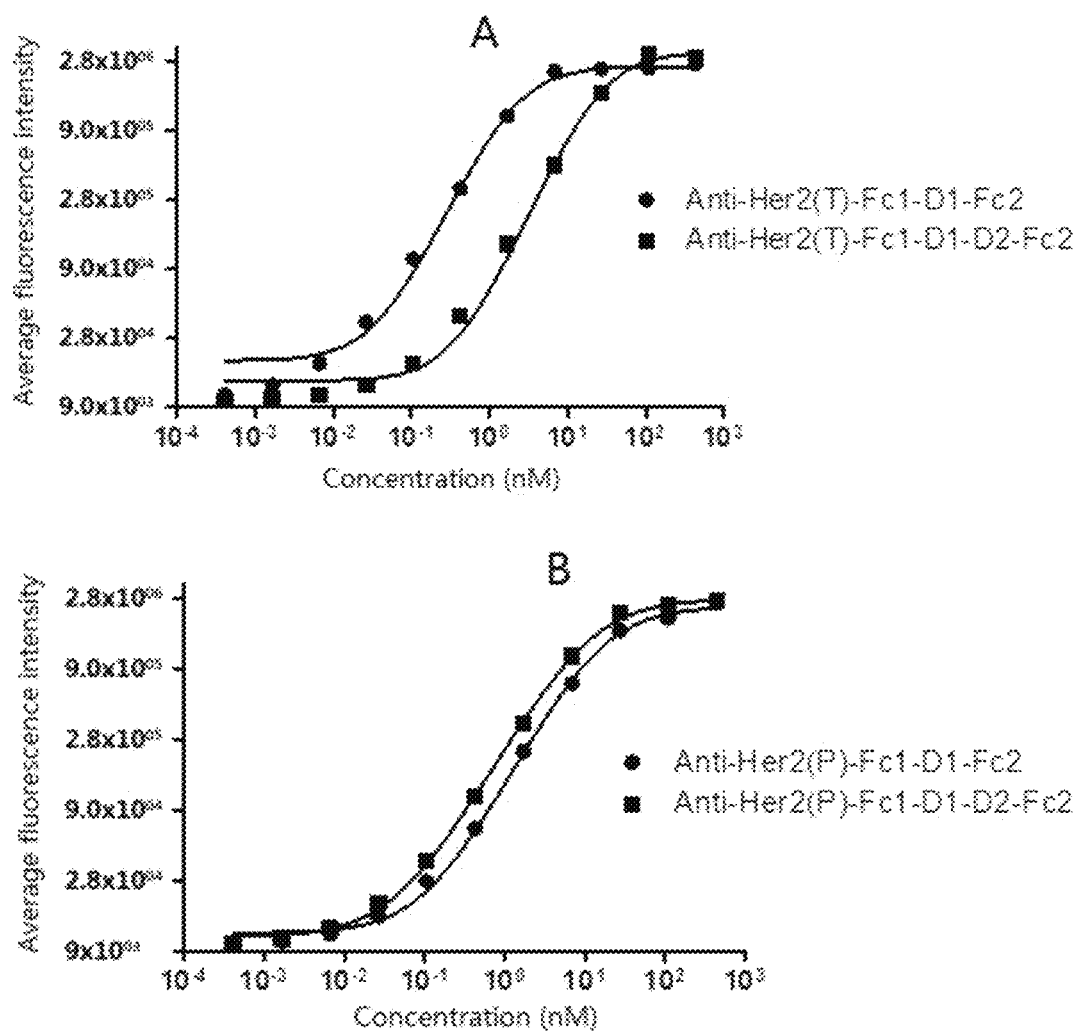
FIG. 16 shows the results of the binding of the recombinant proteins of the present disclosure to the dual targets (Her2, CD47) in SKBR-3.

For example, as shown in FIG. 16, the binding capability of Anti-Her2(T)-Fc1-D1-Fc2 ($EC_{50}$=2.04 nM) to SKBR-3 cells is significantly better than that of Anti-Her2(T)-Fc1-D1-D2-Fc2 ($EC_{50}$=25.95 nM) (FIG. 16A). The binding capability of Anti-Her2(P)-Fc1-D1-Fc2 to SKBR-3 cells ($EC_{50}$=15.22 nM) is equivalent to that of Anti-Her2(P)-Fc1-D1-D2-Fc2 ($EC_{50}$=11.03 nM) (FIG. 16B).

As known to those skilled in the art, the above test results indicate that based on the distance between the epitope of the target antigen and the membrane surface of the target cell, an extracellular truncated variant of human SIRPα with a suitable length for the right arm can effectively enhance the binding capability of the recombinant proteins to the target cell.

EXAMPLE 8

Acute Cytotoxicity Test of the Recombinant Proteins

This embodiment provides an acute cytotoxicity test of the recombinant proteins Ofa-Fc1-D1-Fc2, Ofa-Fc1-D1-D2-Fc2, Ofa-Fc1-D1-D2-D3-Fc2, Obi-Fc1-D1-Fc2, Obi-Fc1-D1-D2-Fc2, Obi-Fc1-D1-D2-D3-Fc2, Anti-EGFR-Fc1-D1-Fc2, Anti-EGFR-Fc1-D1-D2-Fc2, Anti-EGFR-Fc1-D1-D2-D3-Fc2, Anti-Her2(P)-Fc1-D1-Fc2, Anti-Her2(P)-Fc1-D1-D2-Fc2, Anti-Her2(P)-Fc1-D1-D2-D3-Fc2, Anti-Her2(P)-Fc1-D1-Fc2, Anti-Her2(T)-Fc1-D1-D2-Fc2, Anti-Her2(T)-Fc1-D1-D2-D3-Fc2, Anti-EGFR-Fc1-D1-Fc2, Anti-EGFR-Fc1-D1-D2-Fc2, Anti-EGER-Fc1-D1-D2-D3-Fc2, Anti-PD-L1(Ate)-Fc1-D1-Fc2, Anti-PD-L1(Ate)-Fc1-D1-D2-Fc2, Anti-PD-L1 (Ate)-Fc1-D1-D2-D3-Fc2, Anti-PD-L1 (13G4)-Fc1-D1-Fc2, Anti-PD-L1 (13G4)-Fc1-D1-D2-Fc2, Anti-PD-L1(13G4)-Fc1-D1-D2-D3-Fc2, Anti-PD-L1 (12A4)-Fc1-D1-Fc2, Anti-PD-L1(12A4)-Fc1-D1-D2-Fc2 and Anti-PD-L1(12A4)-Fc1-D1-D2-D3-Fc2. The following method takes Ofa-Fc1-D1-Fc2 as an example, which is also applicable for the recombinant proteins with an extracellular truncated variant of SIRPα in the right arm.

A proper amount of Ofa-Fc1-D1-Fc2 solution (4.02 mg/mL) was diluted to 0.25 lnglint, and 2.5 mg/mL, with a buffer (Tris-citrate, pH 6.5) for injection, and used for administrating to the group 1 and group 2 experimental animals, respectively.

Four healthy female cynomolgus monkeys, aged 4, were purchased from Guangxi Guidong Primates Development and Experiment Co., Ltd. The production of the experimental animals is approved by the Department of Science and Technology of the Guangxi Zhuang Autonomous Region, and the license number is SCAK Gui2016-0001. The experimental animals were clinically observed in detail and weighed before administration, and no abnormalities were found. The body weight was 2.47-2.85 kg on the day of initial administration.

TABLE 9

Experimental design

| Group | Treatment | Dose* (mg/kg) | Dosing Concentration (mg/mL) | Dosing volume (mg/kg) | Animal No. Male | Animal No. Female |
|---|---|---|---|---|---|---|
| 1 | Ofa-Fc1-D1-Fc2 | 0.5 | 0.25 | 2 | 0 | 2 |
| 2 | Ofa-Fc1-D1-Fc2 | 5 | 2.5 | 2 | 0 | 2 |

Note:
*intravenous injection.

Four female cynomolgus monkeys were divided into two groups with two monkeys in each group. The animals were intravenously administered at a dose of 0.5 mg/kg and 5 mg/kg respectively, and the dosing volume was 2 mL/kg. The experimental design was shown in Table 9. The animals were administrated once, and then continuously observed for 28 days after the administration. The cynomolgus monkeys were housed in stainless steel movable cages with one animal in each cage. The light was approximately 12 hours on and 12 hours off daily. The feed for the animals were purchased from Beijing KeaoXieli Feed Co., Ltd., and the animals had free access to the feed during the experiment, except for specific fasting period. The batch of the feed was detected by Shanghai Pony Testing Technology Co., Ltd. (PONY) for specific microorganisms, heavy metals and pesticide residues. During the experiment, all animals had free access to drink water via water bottles. The drinking water was purified water filtered and sterilized by reverse osmosis system. The pH, hardness, heavy metals and microorganisms of the drinking water were detected by a gauger.

All animals were observed twice a day (once in the morning and once in the afternoon) near the cage during the experiment, and observations included but were not limited to morbidity, damage, death and the supply of feed and water. All animals were clinically observed in detail once before the experiment. All animals were clinically observed in detail at least once a day after administration during the experiment. Clinical observations included but were not limited to, morbidity, mortality, damage and the supply of feed and water, skin, hair, eyes, ears, nose, mouth, chest, abdomen, external genitalia, limbs, respiratory and circulatory systems, autonomic effects (such as salivation) nervous system (such as fremitus, convulsion, stress reaction, and abnormal behavior). The body weight of the animals was measured on D-1 (before administration), D1, D4, D8, D11, D15, D18, D22, D25 and before dissection. The food consumption of the animals within 24 h (24 h±1 h) was measured on D2, D4, D8, D11, D15, D18, D22, D25, respectively. Electrocardiogram was monitored on D-1, D2, D14, and D28 using a standard II lead (8 leads) at a recording speed of 50 mm/second.

Clinicopathological samples were collected and hematology, blood coagulation, blood biochemistry index and lymphocyte typing were detected before administration (D-1) and on D2, D7, D14 and D28 after administration. Urine samples were collected and analyzed before administration and on day 28 after administration.

Before collecting the sample, all animals were fasted except for free access to water overnight (at least 10 hours). Blood samples (4.5-6 mL) were collected from the femoral vein, wherein approximately 1.8 mL of the whole blood was used for blood coagulation analysis in an anticoagulant tube containing sodium citrate; approximately 1 mL of the whole blood was used for hematology analysis in an anticoagulant tube containing K3-EDTA; approximately 2 mL of the whole blood was used for blood biochemistry analysis in a blood collection tube (free of anticoagulant) with separator gel, and the serum was isolated by centrifugation according to standard operating procedures. Meanwhile, the isolated serum samples on D-1 before administration and on D2 after administration were used for T/B cell typing by flow cytometry.

Animals are euthanized on D29, heart, liver, spleen, lung and kidney tissues were collected and preserved, and liver, lung (including main bronchus), kidney, spleen, heart, adrenal gland, pituitary, thyroid and parathyroid gland, thymus, ovary, uterus (including the cervix), and brain were weighed.

The results showed that, after a single intravenous administration of Ofa-Fc1-D1-Fc2 at a dose of 0.5 mg/kg and 5 mg/kg respectively, the animals were continuously observed for 28 days after administration, no significant abnormalities related to the drug were observed in the animals, the food consumption and body weight were all fluctuated within the normal range; compared to the data before administration, the blood coagulation, urine and electrocardiogram data of the animals after administration had no significant changes; after the animals were dissected, all organs were observed to be within the normal range, and the weight of the organs, visceral coefficient, and the visceral-brain ratio were also within the normal range.

On D2 after administration, the lymphocyte count and the proportion of lymphocytes in the low and high dose groups showed a significant decrease, and returned to a normal level after D7. This change may be related to the effect of the drug.

The recombinant proteins Ofa-Fc1-D1-D2-Fc2, Ofa-Fc1-D1-D2-D3-Fc2, Obi-Fc1-D1-Fc2, Obi-Fc1-D1-D2-Fc2, Obi-Fc1-D1-D2-D3-Fc2, Anti-EGFR-Fc1-D1-Fc2, Anti-EGFR-Fc1-D1-D2-Fc2, Anti-EGER-Fc1-D1-D2-D3-Fc2, Anti-Her2(P)-Fc1-D1-Fc2, Anti-Her2(P)-Fc1-D1-D2-Fc2, Anti-Her2(P)-Fc1-D1-D2-D3-Fc2, Anti-Her2(T)-Fc1-D1-Fc2, Anti-Her2(T)-Fc1-D1-D2-Fc2, Anti-Her2(T)-Fc1-D1-D2-D3-Fc2, Anti-EGFR-Fc1-D1-Fc2, Anti-EGFR-Fc1-D1-D2-Fc2, Anti-EGFR-Fc1-D1-D2-D3-Fc2, Anti-PD-L1(Ate)-Fc1-D1-Fc2, Anti-PD-L1(Ate)-Fc1-D1-D2-Fc2, Anti-PD-L1(Ate)-Fc1-D1-D2-D3-Fc2, Anti-PD-L1(13G4)-Fc1-D1-Fc2, Anti-PD-L1(13G4)-Fc1-D1-D2-Fc2, Anti-PD-L1(13G4)-Fc1-D1-D2-D3-Fc2, Anti-PD-L1(12A4)-Fc1-D1-Fc2, Anti-PD-L1(12A4)-Fc1-D1-D2-Fc2 and Anti-PD-L1(12A4)-Fc1-D1-D2-D3-Fc2 had a similar result to the above results of Ofa-Fc1-D1-Fc2 at the same dose.

TABLE 10

Effect of the recombinant protein on the number of RBCs ($10^{12}$ cells/L) of cynomolgus monkeys

| Group | Parallel experiment | Animal identifier | Before administration | D 2 | D 7 | D 14 | D 28 |
|---|---|---|---|---|---|---|---|
| 1 | 1 | 101 | 4.23 | 4.15 | 3.98 | 5.01 | 5.66 |
|   | 2 | 102 | 4.67 | 4.19 | 4.05 | 4.7 | 5.16 |
| 2 | 1 | 201 | 5.27 | 4.69 | 4.04 | 4.99 | 5.59 |
|   | 2 | 202 | 4.71 | 4.02 | 4.26 | 4.99 | 5.72 |

Figure 18:
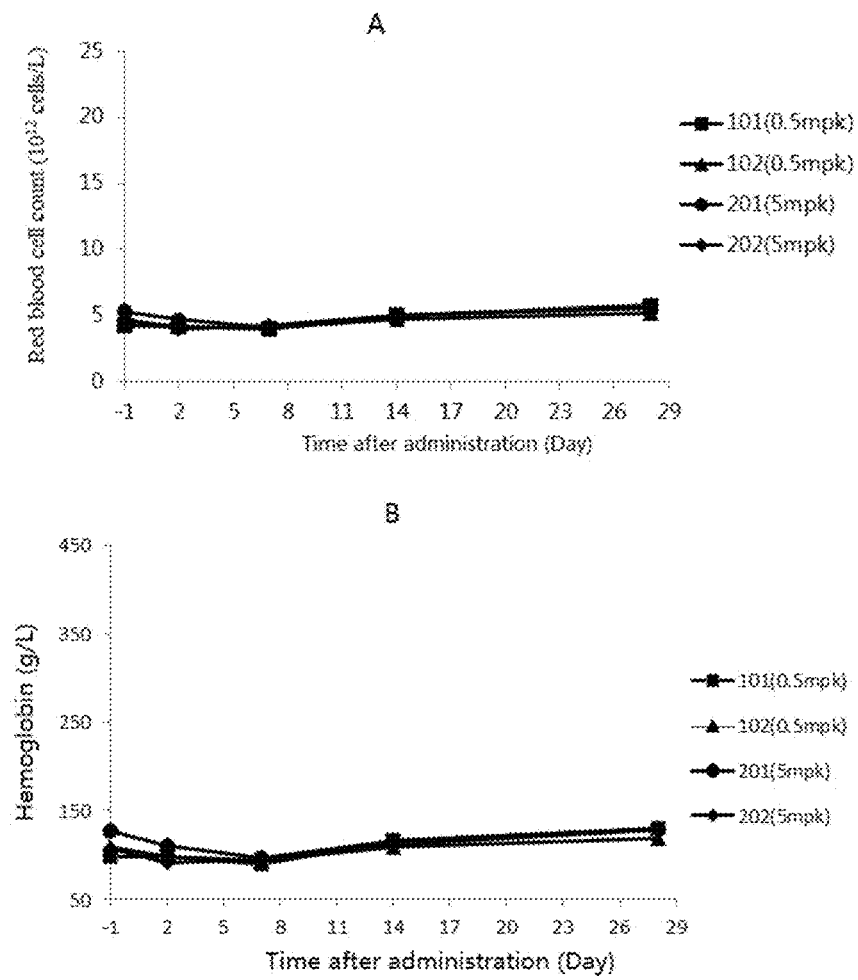
FIG. 18A shows the effect of Ofa-Fc1-D1-Fc2 on the number of RBCs of cynomolgus monkeys at two doses.
FIG. 18B shows the effect of Ofa-Fc1-D1-Fc2 on the hemoglobin of cynomolgus monkeys at two doses.

As shown in FIG. 18A and Table 10, Ofa-Fc1-D1-Fc2 does not affect the number of RBCs of cynomolgus monkeys at both dose of 0.5 mg/kg and 5 mg/kg; as shown in FIG. 18B and Table 10, Ofa-Fc1-D1-Fc2 does not affect the hemoglobin of cynomolgus monkeys at both dose of 0.5 mg/kg and 5 mg/kg.

TABLE 11

Effect of the recombinant protein on the hemoglobin (g/L) of cynomolgus monkeys

| Group | Parallel experiment | Animal identifier | Before administration | D 2 | D 7 | D 14 | D 28 |
|---|---|---|---|---|---|---|---|
| 1 | 1 | 101 | 97 | 97 | 89 | 115 | 129 |
|   | 2 | 102 | 109 | 98 | 93 | 108 | 118 |
| 2 | 1 | 201 | 126 | 110 | 96 | 115 | 129 |
|   | 2 | 202 | 107 | 90 | 95 | 112 | 128 |

The recombinant proteins Ofa-Fc1-D1-D2-Fc2, Ofa-Fc1-D1-D2-D3-Fc2, Obi-Fc1-D1-Fc2, Obi-Fc1-D1-D2-Fc2, Obi-Fc1-D1-D2-D3-Fe2, Anti-EGFR-Fc1-D1-Fc2, Anti-EGFR-Fc1-D1-D2-Fc2, Anti-EGFR-Fc1-D1-D2-D3-Fc2, Anti-Her2(P)-Fc1-D1-Fc2, Anti-Her2(P)-Fc1-D1-D2-Fc2, Anti-Her2(P)-Fc1-D1-D2-D3-Fc2, Anti-Her2(T)-Fc1-D1-Fc2, Anti-Her2(T)-Fc1-D1-D2-Fc2, Anti-Her2(T)-Fc1-D1-D2-D3-Fc2, Anti-EGFR-Fc1-D1-Fc2, Anti-EGFR-Fc1-D1-D2-Fc2, Anti-EGFR-Fc1-D1-D2-D3-Fc2, Anti-PD-L1 (Ate)-Fc1-D1-Fc2, Anti-PD-L1(Ate)-Fc1-D1-D2-Fc2, Anti-PD-L1(Ate)-Fc1-D1-D2-D3-Fc2, Anti-PD-L1(13G4)-Fc1-D1-Fc2, Anti-PD-L1(13G4)-Fc1-D1-D2-Fe2, Anti-PD-L1 (13G4)-Fc1-D1-D2-D3-Fe2, Anti-PD-L1(12A-4)-Fc1-D1-Fc2, Anti-PD-L1(12A4)-Fc1-D1-D2-Fc2 and Anti-PD-L1 (12A4)-Fc1-D1-D2-D3-Fc2 had a similar effect on the number of RBCs and the amount of hemoglobin of cynomolgus monkeys compared to the above results of Ofa-Fc1-D1-Fc2 at the same dose.

Figure 19:
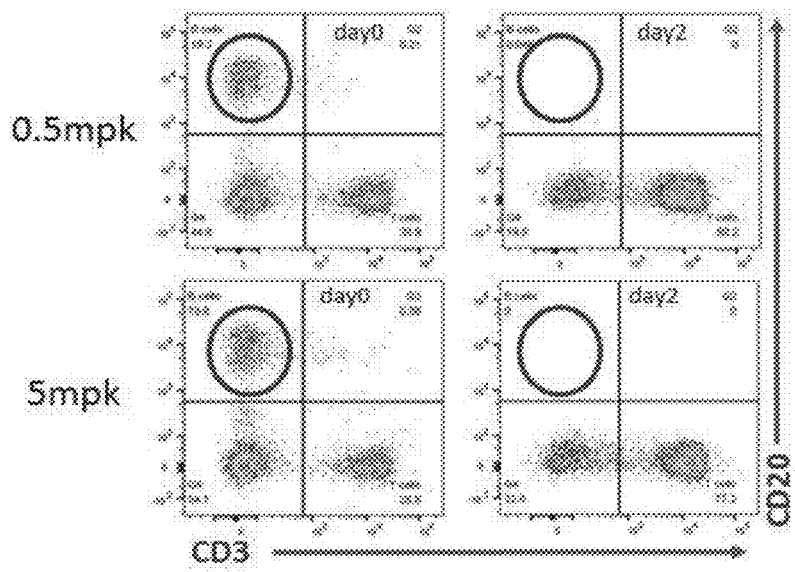
FIG. 19 shows the detection results of Ofa-Fc1-D1-Fc2 on B cell content of cynomolgus monkeys at two doses.

As shown in FIG. 19, based on the test results of the T/B cell typing, Ofa-Fc1-D1-Fc2 can significantly eliminate B cells (the target cell with the CD20 antigen) of the animals at both dose of 0.5 mg/kg and 5 mg/kg.

As known to those skilled in the art, the above test results indicated that, after a single administration of the recombinant proteins of the present disclosure which are capable of simultaneously binding to the target antigen and the CD47 antigen, no significant abnormalities related to the drug were observed in the animals, the food consumption and body weight were all fluctuated within the normal range; compared to the data before administration, the blood coagulation, urine and electrocardiogram data of the animals after administration had no significant changes; after the animals were dissected, all organs were observed to be within the normal range, and the weight of the organs, visceral coefficient, and the visceral-brain ratio were also within the normal range.

As known to those skilled in the art, the above test results indicate that, after a single administration of the recombinant proteins of the present disclosure which are capable of simultaneously binding to the target antigen and the CD47 antigen, the number of RBCs and the amount of hemoglobin of the animal were not affected.

As known to those skilled in the art, the above test results indicate that the recombinant proteins of the present disclosure which are capable of simultaneously binding to the target antigen and the CD47 antigen preferentially clears the cells and/or tumor cells with the tumor-targeting antigen under the condition of a same dose.

EXAMPLE 9

Inhibition of Tumor Growth by the Recombinant Proteins in Vivo

Experiments of the recombinant proteins Ofa-Fc1-D1-Fc2, Ofa-Fc1-D1-D2-Fc2, Ofa-Fc1-D1-D2-D3-Fc2, Obi-Fc1-D1-Fc2, Obi-Fc1-D1-D2-Fc2, Obi-Fc1-D1-D2-D3-Fc2, Anti-EGFR-Fc1-D1-Fc2, Anti-EGFR-Fc1-D1-D2-Fc2, Anti-EGFR-Fc1-D1-D2-D3-Fc2, Anti-Her2(P)-Fc1-D1-Fc2, Anti-Her2(P)-Fc1-D1-D2-Fc2, Anti-Her2(P)-Fc1-D1-D2-D3-Fc2, Anti-Her2(T)-Fc1-D1-Fc2, Anti-Her2(T)-Fc1-D1-D2-Fc2, Anti-Her2(T)-Fc1-D1-D2-D3-Fc2, Anti-EGFR-Fc1-D1-Fc2, Anti-EGFR-Fc1-D1-D2-Fc2, Anti-EGFR-Fc1-D1-D2-D3-Fc2, Anti-PD-L1(Ate)-Fc1-D1-Fc2, Anti-PD-L1(Ate)-Fc1-D1-D2-Fc2, Anti-PD-L1(Ate)-Fc1-D1-D2-D3-Fc2, Anti-PD-L1(13G4)-Fc1-D1-Fc2, Anti-PD-L1(13G4)-Fc1-D1-D2-Fc2, Anti-PD-L1 (13G4)-Fc1-D1-D2-D3-Fc2, Anti-PD-L1 (12A4)-Fc1-D1-Fc2, Anti-PD-L1 (12A4)-Fc1-D1-D2-Fc2, Anti-PD-L1(12A4)-Fc1-D1-D2-D3-Fc2 on inhibition of tumor growth were conducted respectively in vivo. Ofa-Fc1-D1-Fc2 was taken as an example, and the following method is applicable for the recombinant proteins comprising an extracellular truncated variant of SIRPα in the right arm.

Ofa-Fc1-D1-Fc2: a colorless clear liquid with a concentration of 1.14-4.02 mg/mL was aliquoted and stored at −80° C.; Rituxan® (rituximab injection): a colorless clear liquid 100 mg/10 mL, Lot No. H0205, stored at 2-8° C. and protected from light. Preparation Buffer (Tris-citrate, pH 6.5): a colorless clear liquid, stored at 2-8° C.

Formulation: Ofa-Fc1-D1-Fc2 and Rituxan® were diluted with the preparation buffer; the preparation buffer was directly administered as the solvent.

Cell: CD20-positive human B-cell lymphoma Daudi cells were purchased from the Cell Bank of Chinese Academy of Sciences and cultured with RPMI 1640 medium supplemented with 10% fetal bovine serum, penicillin and streptomycin in an incubator containing 5% $CO_2$ at 37° C. The cells were passaged twice a week, and the cells in the exponential growth phase were collected, counted and inoculated.

Experimental animals: Female NOD-SCID mice, 6-7 weeks, purchased from Shanghai Lingchang Biotech Co., Ltd.; license number: SCXK (Hu) 2013-0018. Animal certificate number: 2013001829463, 2013001827545. Feeding environment: SIT level. The use and welfare of the experimental animals shall comply with the provisions of Association for Assessment and Accreditation of Laboratory Animal Care (AAALAC). The health status and mortality of the animals were monitored daily. Routine monitoring included observing the effects of the test substances and drugs on the daily behavior of the animals such as behavioral activities, weight changes, and appearances.

Each mouse was subcutaneously inoculated with 1.5×10⁷ Baudi cells, and when the average tumor volume reached 100-150 mm³ on the 18th day after the inoculation, the animals were divided into different groups and administered (D0). The mice were intravenously (IV) injected with the drugs; the mice in the control group were injected with a same volume of the solvent; the injection volume was 0.1 mL per 10 g body weight. The dose and dosage regimen refers to Table 12.

The diameter of the tumor was measured twice a week with a vernier caliper. The tumor volume (V) is calculated by the following formula:

The tumor volume (V) is calculated by the following formula:

$$V=\tfrac{1}{2}a\times b^2;$$

wherein a and b represent the length and width respectively.

$$T/C(\%)=(T-T0)/(C-C0)\times 100;$$

wherein T and C represent the tumor volume at the end of the experiment; T0 and C0 represent the tumor volume at the start of the experiment; T represents the treatment group, and C represents the control group.

Tumor inhibition rate: (TGI)(%)=100−T/C(%)

When the tumor regresses, the tumor inhibition rate (TGI) (%)=100−(T−T0)/T0×100.

If the tumor volume is smaller than the initial volume, i.e., T<T0 or C<C0, it is defined as tumor partial regression (PR); if the tumor completely disappears, it is defined as tumor complete regression (CR).

When the experiment is over, or when the tumor volume of the animal reached a euthanasia endpoint of 1500 mm³, the animals were euthanatized by carbon dioxide anesthesia, and then the tumor was taken by dissection and photographed.

The comparison of the tumor volume and weight between the two groups was conducted by two-tailed Students t test, and P<0.05 was defined as a statistically significant difference.

Figure 20:
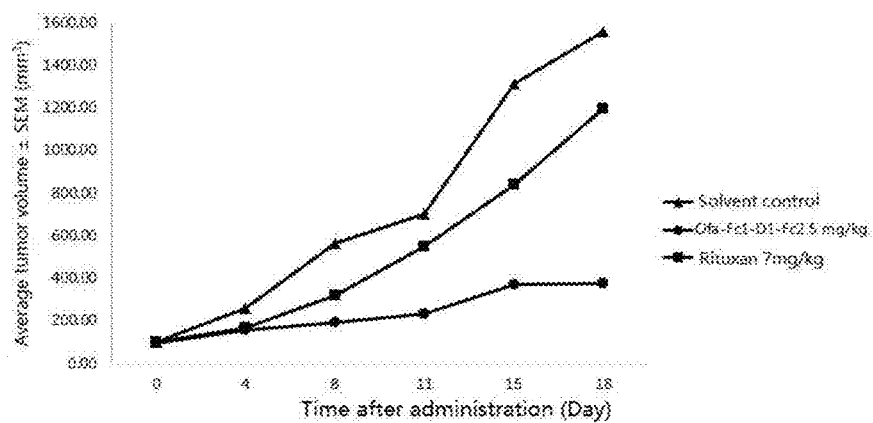
FIG. 20 shows the effect of Ofa-Fc1-D1-Fc2 and Rituxan® on the growth of human B-cell lymphoma Daudi subcutaneous xenografts.
Figure 21:
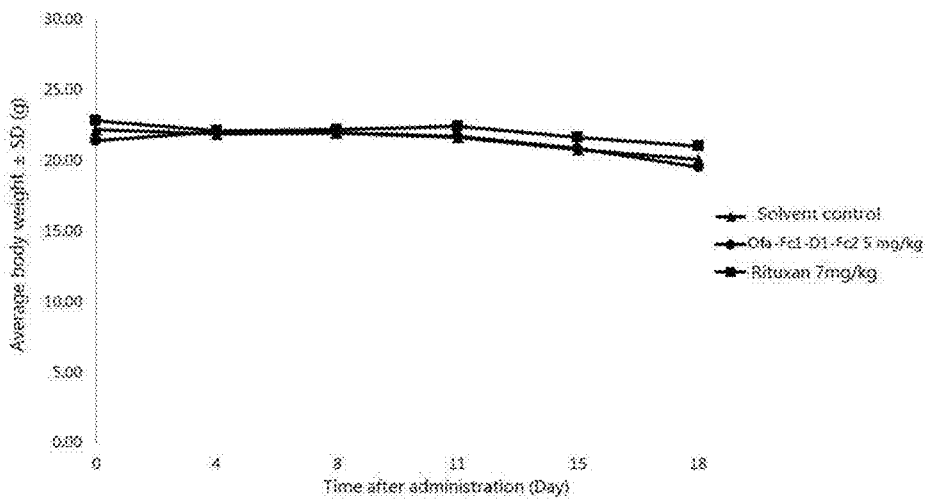
FIG. 21 shows the effect of Ofa-Fc1-D1-Fc2 and Rituxan® on the body weight of tumor-bearing mice.
Figure 22:
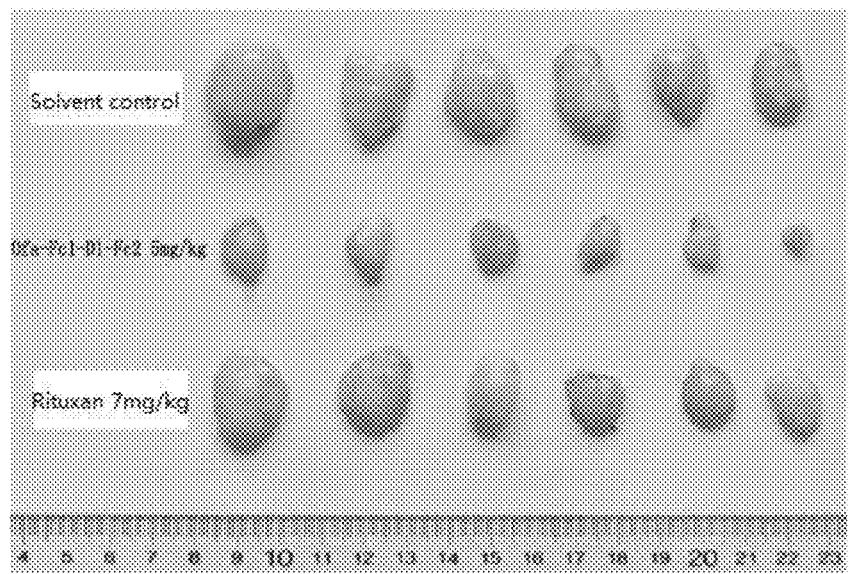
FIG. 22 shows the effect of Ofa-Fc1-D1-Fc2 and Rituxan® on human B-cell lymphoma Daudi subcutaneous xenografts.

Ofa-Fc1-D1-Fc2 (5 mg/kg, IV, twice a week for 5 times) significantly inhibited the growth of Daudi subcutaneously transplanted tumor, with an inhibition rate of 80.8% and tumor partial regression in 1/6 mice. Rituxan® (7 mg/kg, IV twice a week for 5 times) had a tumor inhibition rate of 24.5% on the Daudi subcutaneously transplanted tumor. Tumor-bearing mice were generally well tolerated to the above drugs (Table 12, FIG. 20, 21, 22).

It can be seen that both Ofa-Fc1-D1-Fc2 and Rituxan® inhibited the growth of CD20-positive human B cell lymphoma Daudi subcutaneous xenograft tumor to varying degrees, wherein Ofa-Fc1-D1-Fc2 is significantly superior to Rituxan®; Mice are generally well tolerated to the above drugs.

The anti-tumor effect of the recombinant proteins Ofa-Fc1-D1-D2-Fc2, Ofa-Fc1-D1-D2-D3-Fc2, Obi-Fc1-D1-Fc2, Obi-Fc1-D1-D2-Fc2, Obi-Fc1-D1-D2-D3-Fc2, Anti-EGFR-Fc1-D1-Fc2, Anti-EGFR-Fc1-D1-D2-Fc2, Anti-EGFR-Fc1-D1-D2-D3-Fc2, Anti-Her2(P)-Fc1-D1-Fc2, Anti-Her2(P)-Fc1-D1-D2-Fc2, Anti-Her2(P)-Fc1-D1-D2-D3-Fc2, Anti-Her2(T)-Fc1-D1-Fc2, Anti-Her2(T)-Fc1-D1-D2-Fc2, Anti-Her2(T)-Fc1-D1-D2-D3-Fc2, Anti-EGFR-Fc1-D1-Fc2, Anti-EGFR-Fc1-D1-D2-Fc2, Anti-EGFR-Fc1-D1-D2-D3-Fc2, Anti-PD-L1(Ate)-Fc1-D1-Fc2, Anti-PD-L1(Ate)-Fc1-D1-D2-Fc2, Anti-PD-L1(Ate)-Fc1-D1-D2-D3-Fc2, Anti-PD-L1(13G4)-Fc1-D1-Fc2, Anti-PD-L1(13G4)-Fc1-D1-D2-Fc2, Anti-PD-L1(13G4)-Fc1-D1-D2-D3-Fc2, Anti-PD-L1(12A4)-Fc1-D1-Fc2, Anti-PD-L1(12A4)-Fc1-D1-D2-Fc2 and Anti-PD-L1(12A4)-Fc1-D1-D2-D3-Fc2 on the transplanted tumor in NOD-SCID mice at the same dose and the tolerance of the mice to the recombinant proteins were similar to the above results of Ofa-Fc1-D1-Fc2.

As known to those skilled in the art, the above test results indicate that the recombinant proteins of the present disclosure which are capable of simultaneously binding to the tumor-targeting antigen and the CD47 antigen have an unexpectedly significant anti-tumor effect compared to the tumor-targeting antibody at the condition of a same dose.

The use and welfare of the experimental animals shall comply with the provisions of Association for Assessment and Accreditation of Laboratory Animal Care (AAALAC), The health status and mortality of the animals were monitored daily. Routine monitoring included observing the effects of the test substances and drugs on the daily behavior of the animals such as behavioral activities, weight changes, and appearances.

The use of any and all examples, or exemplary language (e.g., "such as") provided herein, is intended merely to better illuminate the present invention and does not pose a limitation on the scope of the present invention unless otherwise claimed. No language in the specification should be construed as indicating any non-claimed element as essential to the practice of the present invention.

All publications and patent applications mentioned in this specification are herein incorporated by reference in their entireties to the same extent as if each individual publication

TABLE 12

Efficacy of Ofa-Fc1-D1-Fc2 and Rituxan ® on the human B cell lymphoma Daudi subcutaneously transplanted tumor

| Group | Administration | Route | Average tumor volume (mm³) D 0 | SEM | Average tumor volume (mm³) D 18 | SEM | % T/C | (TGI) (%) | P value | Partial regression | Complete regression | Animal number at the start | Animal number at the end |
|---|---|---|---|---|---|---|---|---|---|---|---|---|---|
| Solvent | D 0, | IV | 103.3 | ±1.7 | 1558.7 | ±374.6 | — | — | — | 0 | 0 | 6 | 6 |
| Ofa-Fc1-D1-Fc2 | D 3, D 7, | | 99.4 | ±1.7 | 378.8 | ±97.5 | 19.2 | 80.8 | 0.0124 | 1 | 0 | 6 | 6 |
| Rituxan ® 7 mg/kg | D 10, D 14 | | 101.6 | ±1.0 | 1200.8 | ±175.7 | 75.5 | 24.5 | 0.4089 | 0 | 0 | 6 | 6 |

Note:
Randomly divided into groups, the first administration time is D 0; IV: intravenous injection.

or patent application is specifically and individually indicated to be incorporated by reference. In addition, any theory, mechanism, proof, or finding stated herein is meant to further enhance understanding of the present invention and is not intended to limit the inventions in any way to such theory, mechanism, proof, or finding. While the present invention has been illustrated and described in detail in the drawings and foregoing description, such illustration and description are to be considered illustrative and not restrictive.

What is claimed is:

1. A bispecific recombinant protein, wherein the bispecific recombinant protein comprises a high affinity tumor-targeting arm and a fusion protein with low affinity for blocking the interaction between CD47 and SIRPα;
   wherein the bispecific recombinant protein has a configuration comprising a left arm and a right arm which are symmetrically arranged, wherein the high affinity tumor-targeting arm is arranged in the left arm, the fusion protein with low affinity for blocking the interaction between CD47 and SIRPα is arranged in the right arm;
   wherein the high affinity tumor-targeting arm and the fusion protein with low affinity for blocking the interaction between CD47 and SIRPα are combined via intermolecular force, interchain disulfide bond and salt bond;
   wherein when the high affinity tumor-targeting arm targets CD20, the high affinity tumor-targeting arm comprises SEQ ID No: 16 and SEQ ID No: 17, the fusion protein with low affinity for blocking the interaction between CD47 and SIRPα comprises SEQ ID No: 26;
   when the high affinity tumor-targeting arm targets EGFR, the high affinity tumor-targeting arm comprises SEQ ID No: 19 and SEQ ID No: 8, the fusion protein with low affinity for blocking the interaction between CD47 and SIRPα comprises SEQ ID No: 26;
   when the high affinity tumor-targeting arm targets Her2, the high affinity tumor-targeting arm comprises SEQ ID No: 20 and SEQ ID No: 21, or SEQ ID No: 22 and SEQ ID No: 23, the fusion protein with low affinity for blocking the interaction between CD47 and SIRPα comprises SEQ ID No: 26 or SEQ ID No: 27; or
   when the high affinity tumor-targeting arm targets PD-L1, the high affinity tumor-targeting arm comprises SEQ ID No: 24 and SEQ ID No: 13, the fusion protein with low affinity for blocking the interaction between CD47 and SIRPα comprises SEQ ID No: 26.

2. A nucleic acid molecule encoding the bispecific recombinant protein of claim 1, the nucleic acid molecule encoding the high affinity tumor-targeting arm and the nucleic acid molecule encoding the fusion protein with low affinity for blocking the interaction between CD47 and SIRPα are presented together in the same DNA strand, or the nucleic acid molecule encoding the high affinity tumor-targeting arm and the nucleic acid molecule encoding the fusion protein with low affinity for blocking the interaction between CD47 and SIRPα are presented in separate DNA strands.

3. An expression vector comprising the nucleic acid molecule of claim 2.

4. A host cell comprising the expression vector of claim 3.

5. A method for preparing a bispecific recombinant protein, wherein the method employs the cell of claim 4 to express the recombinant protein.

6. A pharmaceutical composition comprising the bispecific recombinant protein of claim 1, and an optional adjuvant, excipient or pharmaceutically acceptable carrier.

7. The bispecific recombinant protein of claim 1, wherein the high affinity tumor-targeting arm and the fusion protein with low affinity for blocking the interaction between CD47 and SIRPα are heterodimerized by knobs-into-holes.

8. A bispecific recombinant protein, wherein the bispecific recombinant protein comprises a high affinity tumor-targeting arm and a fusion protein with low affinity for blocking the interaction between CD47 and SIRPα;
   wherein the bispecific recombinant protein has a configuration comprising a left arm and a right arm which are symmetrically arranged, wherein the high affinity tumor-targeting arm is arranged in the left arm, the fusion protein with low affinity for blocking the interaction between CD47 and SIRPα is arranged in the right arm;
   wherein the length of the right arm is configured for the distance from the epitope to which the left arm binds to the membrane surface of the target cell;

wherein the high affinity tumor-targeting arm is a half antibody specific to CD20;

wherein the high affinity tumor-targeting arm and the fusion protein with low affinity for blocking the interaction between CD47 and SIRPα are combined via intermolecular force, covalent bond and salt bond; and wherein the high affinity tumor-targeting arm targets CD20, the high affinity tumor-targeting arm comprises SEQ ID No: 18 and SEQ ID No: 4, the fusion protein with low affinity for blocking the interaction between CD47 and SIRPα comprises SEQ ID No: 26.

9. A nucleic acid molecule encoding the bispecific recombinant protein of claim 8, the nucleic acid molecule encoding the high affinity tumor-targeting arm and the nucleic acid molecule encoding the fusion protein with low affinity for blocking the interaction between CD47 and SIRPα are presented together in the same DNA strand, or the nucleic acid molecule encoding the high affinity tumor-targeting arm and the nucleic acid molecule encoding the fusion protein with low affinity for blocking the interaction between CD47 and SIRPα are presented in separate DNA strands.

10. An expression vector comprising the nucleic acid molecule of claim 9.

11. A host cell comprising the expression vector of claim 10.

12. A method for preparing a bispecific recombinant protein, wherein the method employs the cell of claim 11 to express the recombinant protein.

\* \* \* \* \*

SEQUENCE LISTING

```
<160> NUMBER OF SEQ ID NOS: 44

<210> SEQ ID NO 1
<211> LENGTH: 471
<212> TYPE: PRT
<213> ORGANISM: Artificial Sequence
<220> FEATURE:
<223> OTHER INFORMATION: Ofa heavy chain amino acid sequence

<400> SEQUENCE: 1

Met Glu Trp Ser Trp Val Phe Leu Phe Phe Leu Ser Val Thr Thr Gly
1               5                   10                  15

Val His Ser Glu Val Gln Leu Val Glu Ser Gly Gly Gly Leu Val Gln
                20                  25                  30

Pro Gly Arg Ser Leu Arg Leu Ser Cys Ala Ala Ser Gly Phe Thr Phe
            35                  40                  45

Asn Asp Tyr Ala Met His Trp Val Arg Gln Ala Pro Gly Lys Gly Leu
        50                  55                  60

Glu Trp Val Ser Thr Ile Ser Trp Asn Ser Gly Ser Ile Gly Tyr Ala
65                  70                  75                  80

Asp Ser Val Lys Gly Arg Phe Thr Ile Ser Arg Asp Asn Ala Lys Lys
                85                  90                  95

Ser Leu Tyr Leu Gln Met Asn Ser Leu Arg Ala Glu Asp Thr Ala Leu
            100                 105                 110

Tyr Tyr Cys Ala Lys Asp Ile Gln Tyr Gly Asn Tyr Tyr Tyr Gly Met
        115                 120                 125

Asp Val Trp Gly Gln Gly Thr Thr Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320
```

-continued

```
Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 2
<211> LENGTH: 234
<212> TYPE: PRT
<213> ORGANISM: Artificial Sequence
<220> FEATURE:
<223> OTHER INFORMATION: Ofa light chain amino acid sequence

<400> SEQUENCE: 2

Met Ser Val Pro Thr Gln Val Leu Gly Leu Leu Leu Leu Trp Leu Thr
1               5                   10                  15

Asp Ala Arg Cys Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro Ile Thr Phe Gly Gln Gly Thr Arg Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205
```

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 3
<211> LENGTH: 468
<212> TYPE: PRT
<213> ORGANISM: Artificial Sequence
<220> FEATURE:
<223> OTHER INFORMATION: Obi heavy chain amino acid sequence

<400> SEQUENCE: 3

Met Glu Trp Ser Trp Val Phe Leu Phe Phe Leu Ser Val Thr Thr Gly
1               5                   10                  15

Val His Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Ala Phe
        35                  40                  45

Ser Tyr Ser Trp Ile Asn Trp Val Arg Gln Ala Pro Gly Gln Gly Leu
    50                  55                  60

Glu Trp Met Gly Arg Ile Phe Pro Gly Asp Gly Asp Thr Asp Tyr Asn
65                  70                  75                  80

Gly Lys Phe Lys Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Asn Val Phe Asp Gly Tyr Trp Leu Val Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Asp Glu Leu Thr Lys Asn Gln Val
        370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
        450                 455                 460

Ser Pro Gly Lys
465

<210> SEQ ID NO 4
<211> LENGTH: 239
<212> TYPE: PRT
<213> ORGANISM: Artificial Sequence
<220> FEATURE:
<223> OTHER INFORMATION: Obi/Obi-Fc1 light chain amino acid sequence

<400> SEQUENCE: 4

Met Ser Val Pro Thr Gln Val Leu Gly Leu Leu Leu Leu Trp Leu Thr
1               5                   10                  15

Asp Ala Arg Cys Asp Ile Val Met Thr Gln Thr Pro Leu Ser Leu Pro
            20                  25                  30

Val Thr Pro Gly Glu Pro Ala Ser Ile Ser Cys Arg Ser Ser Lys Ser
        35                  40                  45

Leu Leu His Ser Asn Gly Ile Thr Tyr Leu Tyr Trp Tyr Leu Gln Lys
    50                  55                  60

Pro Gly Gln Ser Pro Gln Leu Leu Ile Tyr Gln Met Ser Asn Leu Val
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Ala Gln Asn Leu Glu Leu Pro Tyr Thr Phe Gly Gly Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 5
<211> LENGTH: 461
<212> TYPE: PRT
<213> ORGANISM: Artificial Sequence
<220> FEATURE:
<223> OTHER INFORMATION: Hu5F9-G4 heavy chain amino acid sequence

<400> SEQUENCE: 5

Met Arg Ala Trp Ile Phe Phe Leu Leu Cys Leu Ala Gly Arg Ala Leu
1               5                   10                  15

Ala Gln Val Gln Leu Val Gln Ser Gly Ala Glu Val Lys Lys Pro Gly
            20                  25                  30

Ala Ser Val Lys Val Ser Cys Lys Ala Ser Gly Tyr Thr Phe Thr Asn
        35                  40                  45

Tyr Asn Met His Trp Val Arg Gln Ala Pro Gly Gln Arg Leu Glu Trp
    50                  55                  60

Met Gly Thr Ile Tyr Pro Gly Asn Asp Asp Thr Ser Tyr Asn Gln Lys
65                  70                  75                  80

Phe Lys Asp Arg Val Thr Ile Thr Ala Asp Thr Ser Ala Ser Thr Ala
                85                  90                  95

Tyr Met Glu Leu Ser Ser Leu Arg Ser Glu Asp Thr Ala Val Tyr Tyr
            100                 105                 110

Cys Ala Arg Gly Gly Tyr Arg Ala Met Asp Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Lys Thr Tyr Thr Cys Asn Val Asp His Lys Pro Ser
    210                 215                 220

Asn Thr Lys Val Asp Lys Arg Val Glu Ser Lys Tyr Gly Pro Pro Cys
225                 230                 235                 240

Pro Pro Cys Pro Ala Pro Glu Phe Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser Gln Glu Asp Pro Glu Val Gln
        275                 280                 285

Phe Asn Trp Tyr Val Asp Gly Val Glu Val His Asn Ala Lys Thr Lys
    290                 295                 300

Pro Arg Glu Glu Gln Phe Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Gly Leu Pro Ser Ser Ile Glu Lys Thr Ile Ser Lys
            340                 345                 350

```
Ala Lys Gly Gln Pro Arg Glu Pro Gln Val Tyr Thr Leu Pro Pro Ser
        355                 360                 365

Gln Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Arg Leu Thr Val Asp Lys Ser Arg Trp Gln
                420                 425                 430

Glu Gly Asn Val Phe Ser Cys Ser Val Met His Glu Ala Leu His Asn
            435                 440                 445

His Tyr Thr Gln Lys Ser Leu Ser Leu Ser Leu Gly Lys
    450                 455                 460

<210> SEQ ID NO 6
<211> LENGTH: 236
<212> TYPE: PRT
<213> ORGANISM: Artificial Sequence
<220> FEATURE:
<223> OTHER INFORMATION: Hu5F9-G4 light chain amino acid sequence

<400> SEQUENCE: 6

Met Arg Ala Trp Ile Phe Phe Leu Leu Cys Leu Ala Gly Arg Ala Leu
1               5                   10                  15

Ala Asp Ile Val Met Thr Gln Ser Pro Leu Ser Leu Pro Val Thr Pro
            20                  25                  30

Gly Glu Pro Ala Ser Ile Ser Cys Arg Ser Ser Gln Ser Ile Val Tyr
        35                  40                  45

Ser Asn Gly Asn Thr Tyr Leu Gly Trp Tyr Leu Gln Lys Pro Gly Gln
    50                  55                  60

Ser Pro Gln Leu Leu Ile Tyr Lys Val Ser Asn Arg Phe Ser Gly Val
65                  70                  75                  80

Pro Asp Arg Phe Ser Gly Ser Gly Ser Gly Thr Asp Phe Thr Leu Lys
                85                  90                  95

Ile Ser Arg Val Glu Ala Glu Asp Val Gly Val Tyr Tyr Cys Phe Gln
            100                 105                 110

Gly Ser His Val Pro Tyr Thr Phe Gly Gln Gly Thr Lys Leu Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 7
<211> LENGTH: 466
```

```
<212> TYPE: PRT
<213> ORGANISM: Artificial Sequence
<220> FEATURE:
<223> OTHER INFORMATION: JMT101 heavy chain amino acid sequence

<400> SEQUENCE: 7

Met Arg Ala Trp Ile Phe Phe Leu Leu Cys Leu Ala Gly Arg Ala Leu
1               5                   10                  15

Ala Gln Val Gln Leu Gln Glu Ser Gly Pro Gly Leu Val Lys Pro Ser
                20                  25                  30

Glu Thr Leu Ser Leu Thr Cys Thr Val Ser Gly Phe Ser Leu Ser Asn
            35                  40                  45

Tyr Asp Val His Trp Val Arg Gln Ala Pro Gly Lys Gly Leu Glu Trp
        50                  55                  60

Leu Gly Val Ile Trp Ser Gly Gly Asn Thr Asp Tyr Asn Thr Pro Phe
65                  70                  75                  80

Thr Ser Arg Leu Thr Ile Ser Val Asp Thr Ser Lys Asn Gln Phe Ser
                85                  90                  95

Leu Lys Leu Ser Ser Val Thr Ala Ala Asp Thr Ala Val Tyr Tyr Cys
                100                 105                 110

Ala Arg Ala Leu Asp Tyr Tyr Asp Tyr Glu Phe Ala Tyr Trp Gly Gln
                115                 120                 125

Gly Thr Leu Val Thr Val Ser Ser Ala Ser Thr Lys Gly Pro Ser Val
            130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
                180                 185                 190

Leu Gln Ser Ser Gly Leu Tyr Ser Leu Ser Ser Val Val Thr Val Pro
            195                 200                 205

Ser Ser Ser Leu Gly Thr Gln Thr Tyr Ile Cys Asn Val Asn His Lys
210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser His Glu
            275                 280                 285

Asp Pro Glu Val Lys Phe Asn Trp Tyr Val Asp Gly Val Glu Val His
        290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
                340                 345                 350

Lys Thr Ile Ser Lys Ala Lys Gly Gln Pro Arg Glu Pro Gln Val Tyr
            355                 360                 365

Thr Leu Pro Pro Ser Arg Glu Glu Met Thr Lys Asn Gln Val Ser Leu
        370                 375                 380
```

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 8
<211> LENGTH: 231
<212> TYPE: PRT
<213> ORGANISM: Artificial Sequence
<220> FEATURE:
<223> OTHER INFORMATION: JMT101/Anti-EGFR-Fc1 light chain amino acid
      sequence

<400> SEQUENCE: 8

Met Arg Ala Trp Ile Phe Phe Leu Leu Cys Leu Ala Gly Arg Ala Leu
1               5                   10                  15

Ala Glu Ile Val Leu Thr Gln Ser Pro Asp Phe Gln Ser Val Thr Pro
            20                  25                  30

Lys Glu Lys Val Thr Ile Thr Cys Arg Ala Ser Gln Ser Ile Gly Thr
        35                  40                  45

Asn Ile His Trp Tyr Gln Gln Lys Pro Asp Gln Ser Pro Lys Leu Leu
    50                  55                  60

Ile Lys Tyr Ala Ser Glu Ser Ile Ser Gly Ile Pro Ser Arg Phe Ser
65                  70                  75                  80

Gly Ser Gly Ser Gly Thr Asp Phe Thr Leu Thr Ile Asn Ser Leu Glu
                85                  90                  95

Ala Glu Asp Ala Ala Thr Tyr Tyr Cys Gln Gln Asn Asn Glu Trp Pro
            100                 105                 110

Thr Ser Phe Gly Gln Gly Thr Lys Leu Glu Ile Lys Arg Thr Val Ala
        115                 120                 125

Ala Pro Ser Val Phe Ile Phe Pro Pro Ser Asp Glu Gln Leu Lys Ser
    130                 135                 140

Gly Thr Ala Ser Val Val Cys Leu Leu Asn Asn Phe Tyr Pro Arg Glu
145                 150                 155                 160

Ala Lys Val Gln Trp Lys Val Asp Asn Ala Leu Gln Ser Gly Asn Ser
                165                 170                 175

Gln Glu Ser Val Thr Glu Gln Asp Ser Lys Asp Ser Thr Tyr Ser Leu
            180                 185                 190

Ser Ser Thr Leu Thr Leu Ser Lys Ala Asp Tyr Glu Lys His Lys Val
        195                 200                 205

Tyr Ala Cys Glu Val Thr His Gln Gly Leu Ser Ser Pro Val Thr Lys
    210                 215                 220

Ser Phe Asn Arg Gly Glu Cys
225                 230

<210> SEQ ID NO 9
<211> LENGTH: 468
<212> TYPE: PRT
<213> ORGANISM: Artificial Sequence
<220> FEATURE:
<223> OTHER INFORMATION: Trastuzumab heavy chain amino acid sequence

<400> SEQUENCE: 9

```
Met Arg Ala Trp Ile Phe Phe Leu Leu Cys Leu Ala Gly Arg Ala Leu
1               5                   10                  15

Ala Glu Val Gln Leu Val Glu Ser Gly Gly Leu Val Gln Pro Gly
            20                  25                  30

Gly Ser Leu Arg Leu Ser Cys Ala Ala Ser Gly Phe Asn Ile Lys Asp
            35                  40                  45

Thr Tyr Ile His Trp Val Arg Gln Ala Pro Gly Lys Gly Leu Glu Trp
        50                  55                  60

Val Ala Arg Ile Tyr Pro Thr Asn Gly Tyr Thr Arg Tyr Ala Asp Ser
65                  70                  75                  80

Val Lys Gly Arg Phe Thr Ile Ser Ala Asp Thr Ser Lys Asn Thr Ala
                85                  90                  95

Tyr Leu Gln Met Asn Ser Leu Arg Ala Glu Asp Thr Ala Val Tyr Tyr
            100                 105                 110

Cys Ser Arg Trp Gly Gly Asp Gly Phe Tyr Ala Met Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400
```

```
Glu Trp Glu Ser Asn Gly Gln Pro Glu Asn Asn Tyr Lys Thr Thr Pro
            405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
            450                 455                 460

Ser Pro Gly Lys
465

<210> SEQ ID NO 10
<211> LENGTH: 231
<212> TYPE: PRT
<213> ORGANISM: Artificial Sequence
<220> FEATURE:
<223> OTHER INFORMATION: Trastuzumab light chain amino acid sequence

<400> SEQUENCE: 10

Met Arg Ala Trp Ile Phe Phe Leu Leu Cys Leu Ala Gly Arg Ala Leu
1               5                   10                  15

Ala Asp Ile Gln Met Thr Gln Ser Pro Ser Ser Leu Ser Ala Ser Val
            20                  25                  30

Gly Asp Arg Val Thr Ile Thr Cys Arg Ala Ser Gln Asp Val Asn Thr
        35                  40                  45

Ala Val Ala Trp Tyr Gln Gln Lys Pro Gly Lys Ala Pro Lys Leu Leu
    50                  55                  60

Ile Tyr Ser Ala Ser Phe Leu Tyr Ser Gly Val Pro Ser Arg Phe Ser
65                  70                  75                  80

Gly Ser Arg Ser Gly Thr Asp Phe Thr Leu Thr Ile Ser Ser Leu Gln
                85                  90                  95

Pro Glu Asp Phe Ala Thr Tyr Tyr Cys Gln Gln His Tyr Thr Thr Pro
            100                 105                 110

Pro Thr Phe Gly Gln Gly Thr Lys Val Glu Ile Lys Arg Thr Val Ala
        115                 120                 125

Ala Pro Ser Val Phe Ile Phe Pro Pro Ser Asp Glu Gln Leu Lys Ser
    130                 135                 140

Gly Thr Ala Ser Val Val Cys Leu Leu Asn Asn Phe Tyr Pro Arg Glu
145                 150                 155                 160

Ala Lys Val Gln Trp Lys Val Asp Asn Ala Leu Gln Ser Gly Asn Ser
                165                 170                 175

Gln Glu Ser Val Thr Glu Gln Asp Ser Lys Asp Ser Thr Tyr Ser Leu
            180                 185                 190

Ser Ser Thr Leu Thr Leu Ser Lys Ala Asp Tyr Glu Lys His Lys Val
        195                 200                 205

Tyr Ala Cys Glu Val Thr His Gln Gly Leu Ser Ser Pro Val Thr Lys
    210                 215                 220

Ser Phe Asn Arg Gly Glu Cys
225                 230

<210> SEQ ID NO 11
<211> LENGTH: 359
<212> TYPE: PRT
<213> ORGANISM: Artificial Sequence
<220> FEATURE:
<223> OTHER INFORMATION: SIRP D1-Fc amino acid sequence
```

```
<400> SEQUENCE: 11

Met Glu Trp Ser Trp Val Phe Leu Phe Phe Leu Ser Val Thr Thr Gly
1               5                   10                  15

Val His Ser Glu Glu Glu Leu Gln Val Ile Gln Pro Asp Lys Ser Val
            20                  25                  30

Ser Val Ala Ala Gly Glu Ser Ala Ile Leu His Cys Thr Val Thr Ser
        35                  40                  45

Leu Ile Pro Val Gly Pro Ile Gln Trp Phe Arg Gly Ala Gly Pro Ala
    50                  55                  60

Arg Glu Leu Ile Tyr Asn Gln Lys Glu Gly His Phe Pro Arg Val Thr
65              70                  75                  80

Thr Val Ser Glu Ser Thr Lys Arg Glu Asn Met Asp Phe Ser Ile Ser
            85                  90                  95

Ile Ser Ala Ile Thr Pro Ala Asp Ala Gly Thr Tyr Tyr Cys Val Lys
        100                 105                 110

Phe Arg Lys Gly Ser Pro Asp Thr Glu Phe Lys Ser Gly Ala Gly Thr
    115                 120                 125

Glu Leu Ser Val Asp Lys Thr His Thr Cys Pro Pro Cys Pro Ala Pro
130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Asp Glu Leu Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys
        355

<210> SEQ ID NO 12
<211> LENGTH: 467
<212> TYPE: PRT
<213> ORGANISM: Artificial Sequence
<220> FEATURE:
<223> OTHER INFORMATION: Atezolizumab heavy chain amino acid sequence
```

```
<400> SEQUENCE: 12

Met Glu Phe Trp Leu Ser Trp Val Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asp Ser Trp Ile His Trp Val Arg Gln Ala Pro Gly Lys Gly Leu
    50                  55                  60

Glu Trp Val Ala Trp Ile Ser Pro Tyr Gly Ser Thr Tyr Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ala Arg Arg His Trp Pro Gly Gly Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Ala Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415
```

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
450                 455                 460

Pro Gly Lys
465

<210> SEQ ID NO 13
<211> LENGTH: 233
<212> TYPE: PRT
<213> ORGANISM: Artificial Sequence
<220> FEATURE:
<223> OTHER INFORMATION: Atezolizumab/Anti-PD-L1(Ate)-Fc1 light chain
    amino acid sequence

<400> SEQUENCE: 13

Met Glu Phe Trp Leu Ser Trp Val Phe Leu Val Ala Ile Leu Lys Gly
1               5                   10                  15

Val Gln Cys Asp Ile Gln Met Thr Gln Ser Pro Ser Ser Leu Ser Ala
            20                  25                  30

Ser Val Gly Asp Arg Val Thr Ile Thr Cys Arg Ala Ser Gln Asp Val
            35                  40                  45

Ser Thr Ala Val Ala Trp Tyr Gln Gln Lys Pro Gly Lys Ala Pro Lys
50                  55                  60

Leu Leu Ile Tyr Ser Ala Ser Phe Leu Tyr Ser Gly Val Pro Ser Arg
65                  70                  75                  80

Phe Ser Gly Ser Gly Ser Gly Thr Asp Phe Thr Leu Thr Ile Ser Ser
            85                  90                  95

Leu Gln Pro Glu Asp Phe Ala Thr Tyr Tyr Cys Gln Gln Tyr Leu Tyr
            100                 105                 110

His Pro Ala Thr Phe Gly Gln Gly Thr Lys Val Glu Ile Lys Arg Thr
            115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
            165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
210                 215                 220

Thr Lys Ser Phe Asn Arg Gly Glu Cys
225                 230

<210> SEQ ID NO 14
<211> LENGTH: 1092
<212> TYPE: DNA
<213> ORGANISM: Artificial Sequence
<220> FEATURE:
<223> OTHER INFORMATION: D1-Fc2 DNA sequence

<400> SEQUENCE: 14

| | |
|---|---|
| atggaatgga gctgggtgtt cctgttctttt ctgtccgtga ccacaggcgt gcattctgaa | 60 |
| gaggagctgc aggtcatcca gcccgataag agcgtgtccg tggccgcagg agaatctgcc | 120 |
| atcctgcatt gcaccgtgac ctctctgatc cccgtgggcc caatccagtg gttcagagga | 180 |
| gccggaccag ctagagagct gatctacaac cagaaggagg ccacttccc cagagtgaca | 240 |
| accgtgtccg agtctaccaa gcgggagaac atggacttct ccatctccat ctccgccatc | 300 |
| acaccagccg acgccggcac ctactattgc gtgaagttcc ggaagggctc cccagatacc | 360 |
| gagtttaaga gcggcgccgg aacagagctg agcgtgcggg ctaagcctga caagacccac | 420 |
| acctgtcccc cttgtcctgc ccctgaactg ctgggcggac cttccgtgtt cctgttcccc | 480 |
| ccaaagccca aggacaccct gatgatctcc cggacccccg aagtgacctg cgtggtggtg | 540 |
| gatgtgtccc acgaggaccc tgaagtgaag ttcaattggt acgtggacgg cgtggaagtg | 600 |
| cacaacgcca agaccaagcc tagagaggaa cagtacaact ccacctaccg ggtggtgtcc | 660 |
| gtgctgaccg tgctgcacca ggattggctg aacggcaaag agtacaagtg caaggtgtcc | 720 |
| aacaaggccc tgcctgcccc catcgaaaag accatctccca aggccaaggg ccagccccgg | 780 |
| gaaccccagg tgtacacact gccccctagc agggacgagc tgaccaagaa ccaggtgtcc | 840 |
| ctgtggtgtc tcgtgaaagg cttctacccc tccgacattg ccgtggaatg ggagtccaac | 900 |
| ggccagcctg agaacaacta caagaccacc cccctgtgc tggactccga cggctcattc | 960 |
| ttcctgtaca gcaagctgac agtggacaag tcccggtggc agcagggcaa cgtgttctcc | 1020 |
| tgctccgtga tgcacgaggc cctgcacaac cactacaccc agaagtccct gtccctgagc | 1080 |
| cccggcaaat ga | 1092 |

<210> SEQ ID NO 15
<211> LENGTH: 1389
<212> TYPE: DNA
<213> ORGANISM: Artificial Sequence
<220> FEATURE:
<223> OTHER INFORMATION: D1-D2-Fc2 DNA sequence

<400> SEQUENCE: 15

| | |
|---|---|
| atggaatgga gctgggtgtt cctgttctttt ctgtccgtga ccacaggcgt gcattctgaa | 60 |
| gaggagctgc aggtcatcca gcccgataag agcgtgtccg tggccgcagg agaatctgcc | 120 |
| atcctgcatt gcaccgtgac ctctctgatc cccgtgggcc caatccagtg gttcagagga | 180 |
| gccggaccag ctagagagct gatctacaac cagaaggagg ccacttccc cagagtgaca | 240 |
| accgtgtccg agtctaccaa gcgggagaac atggacttct ccatctccat ctccgccatc | 300 |
| acaccagccg acgccggcac ctactattgc gtgaagttcc ggaagggctc cccagatacc | 360 |
| gagtttaaga gcggcgccgg aacagagctg agcgtgcggg ctaagccttc tgctccagtg | 420 |
| gtgtcaggac cagcagctag agctacccct cagcacaccg tgtccttcac ctgcgagtct | 480 |
| cacggcttct cccctagaga catcaccctc aagtggttca agaacggcaa cgagctgtcc | 540 |
| gacttccaga ccaacgtgga tcagtgggc gagagcgtgt cttactccat ccactccacc | 600 |
| gccaaggtgg tgctgacaag ggaggacgtg cactcccagg tcatttgcga ggtggcacac | 660 |
| gtgacattgc agggcgaccc cctgagggga accgccaact tgagtgacaa gacccacacc | 720 |
| tgtcccccctt gtcctgcccc tgaactgctg gccggacctt ccgtgttcct gttcccccca | 780 |
| aagcccaagg acaccctgat gatctcccgg accccgaag tgacctgcgt ggtggtggat | 840 |
| gtgtcccacg aggaccctga agtgaagttc aattggtacg tggacggcgt ggaagtgcac | 900 |
| aacgccaaga ccaagcctag agaggaacag tacaactcca cctaccgggt ggtgtccgtg | 960 |

```
ctgaccgtgc tgcaccagga ttggctgaac ggcaaagagt acaagtgcaa ggtgtccaac    1020
aaggccctgc ctgccccat cgaaaagacc atctccaagg ccaagggcca gccccgggaa    1080
ccccaggtgt acacactgcc ccctagcagg gacgagctga ccaagaacca ggtgtccctg    1140
tggtgtctcg tgaaaggctt ctaccctcc gacattgccg tggaatggga gtccaacggc    1200
cagcctgaga caactacaa gaccaccccc ctgtgctgg actccgacgg ctcattcttc    1260
ctgtacagca agctgacagt ggacaagtcc cggtggcagc agggcaacgt gttctcctgc    1320
tccgtgatgc acgaggccct gcacaaccac tacacccaga gtccctgtc cctgagcccc    1380 ggcaaatga                                                            1389
```

<210> SEQ ID NO 16
<211> LENGTH: 471
<212> TYPE: PRT
<213> ORGANISM: Artificial Sequence
<220> FEATURE:
<223> OTHER INFORMATION: Ofa-Fc1 heavy chain amino acid sequence

<400> SEQUENCE: 16

```
Met Glu Trp Ser Trp Val Phe Leu Phe Phe Leu Ser Val Thr Thr Gly
1               5                   10                  15

Val His Ser Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asn Asp Tyr Ala Met His Trp Val Arg Gln Ala Pro Gly Lys Gly Leu
50                  55                  60

Glu Trp Val Ser Thr Ile Ser Trp Asn Ser Gly Ser Ile Gly Tyr Ala
65                  70                  75                  80

Asp Ser Val Lys Gly Arg Phe Thr Ile Ser Arg Asp Asn Ala Lys Lys
                85                  90                  95

Ser Leu Tyr Leu Gln Met Asn Ser Leu Arg Ala Glu Asp Thr Ala Leu
            100                 105                 110

Tyr Tyr Cys Ala Lys Asp Ile Gln Tyr Gly Asn Tyr Tyr Tyr Gly Met
        115                 120                 125

Asp Val Trp Gly Gln Gly Thr Thr Val Thr Val Ser Ser Ala Ser Thr
130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Leu Gly Thr Gln Thr Tyr Ile Cys
        210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
```

```
            275                 280                 285
Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Ser Cys Ala Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Val Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 17
<211> LENGTH: 234
<212> TYPE: PRT
<213> ORGANISM: Artificial Sequence
<220> FEATURE:
<223> OTHER INFORMATION: Ofa-Fc1  light chain amino acid sequence

<400> SEQUENCE: 17

Met Ser Val Pro Thr Gln Val Leu Gly Leu Leu Leu Leu Trp Leu Thr
1               5                   10                  15

Asp Ala Arg Cys Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro Ile Thr Phe Gly Gln Gly Thr Arg Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
```

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
        180                 185                 190

His Lys Val Tyr Ala Cys Glu Val Thr His Gln Gly Leu Ser Ser Pro
    195                 200                 205

Val Thr Lys Ser Phe Asn Arg Gly Glu Cys
210                 215                 220

Val Thr Lys Ser Phe Asn Arg Gly Glu Cys
225                 230

<210> SEQ ID NO 18
<211> LENGTH: 468
<212> TYPE: PRT
<213> ORGANISM: Artificial Sequence
<220> FEATURE:
<223> OTHER INFORMATION: Obi-Fc1 heavy chain amino acid sequence

<400> SEQUENCE: 18

Met Glu Trp Ser Trp Val Phe Leu Phe Phe Leu Ser Val Thr Thr Gly
1               5                   10                  15

Val His Ser Gln Val Gln Leu Gln Glu Ser Gly Pro Gly Leu Val Lys
            20                  25                  30

Pro Ser Glu Thr Leu Ser Leu Thr Cys Thr Val Ser Gly Phe Ser Leu
        35                  40                  45

Ser Asn Tyr Asp Val His Trp Val Arg Gln Ala Pro Gly Lys Gly Leu
    50                  55                  60

Glu Trp Leu Gly Val Ile Trp Ser Gly Gly Asn Thr Asp Tyr Asn Thr
65                  70                  75                  80

Pro Phe Thr Ser Arg Leu Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Ala Leu Asp Tyr Tyr Asp Tyr Glu Phe Ala Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu

```
                290                 295                 300
Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
                340                 345                 350

Ile Glu Lys Thr Ile Ser Lys Ala Lys Gly Gln Pro Arg Glu Pro Gln
                355                 360                 365

Val Tyr Thr Leu Pro Pro Ser Arg Asp Glu Leu Thr Lys Asn Gln Val
            370                 375                 380

Ser Leu Ser Cys Ala Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Val Ser Lys Leu Thr
                420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
        450                 455                 460

Ser Pro Gly Lys
465

<210> SEQ ID NO 19
<211> LENGTH: 468
<212> TYPE: PRT
<213> ORGANISM: Artificial Sequence
<220> FEATURE:
<223> OTHER INFORMATION: Anti-EGFR-Fc1 heavy chain amino acid sequence

<400> SEQUENCE: 19

Met Glu Trp Ser Trp Val Phe Leu Phe Phe Leu Ser Val Thr Thr Gly
1               5                   10                  15

Val His Ser Gln Val Gln Leu Gln Glu Ser Gly Pro Gly Leu Val Lys
            20                  25                  30

Pro Ser Glu Thr Leu Ser Leu Thr Cys Thr Val Ser Gly Phe Ser Leu
        35                  40                  45

Ser Asn Tyr Asp Val His Trp Val Arg Gln Ala Pro Gly Lys Gly Leu
    50                  55                  60

Glu Trp Leu Gly Val Ile Trp Ser Gly Gly Asn Thr Asp Tyr Asn Thr
65                  70                  75                  80

Pro Phe Thr Ser Arg Leu Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Ala Leu Asp Tyr Tyr Asp Tyr Glu Phe Ala Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
```

```
                180             185              190
Ala Val Leu Gln Ser Ser Gly Leu Tyr Ser Leu Ser Val Val Thr
            195                 200             205
Val Pro Ser Ser Leu Gly Thr Gln Thr Tyr Ile Cys Asn Val Asn
        210              215                 220
His Lys Pro Ser Asn Thr Lys Val Asp Lys Val Glu Pro Lys Ser
225                 230              235                 240
Cys Asp Lys Thr His Thr Cys Pro Pro Cys Pro Ala Pro Glu Leu Leu
                245              250                 255
Gly Gly Pro Ser Val Phe Leu Phe Pro Pro Lys Pro Lys Asp Thr Leu
            260                 265              270
Met Ile Ser Arg Thr Pro Glu Val Thr Cys Val Val Val Asp Val Ser
        275                 280              285
His Glu Asp Pro Glu Val Lys Phe Asn Trp Tyr Val Asp Gly Val Glu
        290                 295              300
Val His Asn Ala Lys Thr Lys Pro Arg Glu Glu Gln Tyr Asn Ser Thr
305                 310              315                 320
Tyr Arg Val Val Ser Val Leu Thr Val Leu His Gln Asp Trp Leu Asn
                325              330                 335
Gly Lys Glu Tyr Lys Cys Lys Val Ser Asn Lys Ala Leu Pro Ala Pro
            340                 345              350
Ile Glu Lys Thr Ile Ser Lys Ala Lys Gly Gln Pro Arg Glu Pro Gln
            355                 360              365
Val Tyr Thr Leu Pro Pro Ser Arg Asp Glu Leu Thr Lys Asn Gln Val
        370                 375              380
Ser Leu Ser Cys Ala Val Lys Gly Phe Tyr Pro Ser Asp Ile Ala Val
385                 390              395                 400
Glu Trp Glu Ser Asn Gly Gln Pro Glu Asn Asn Tyr Lys Thr Thr Pro
                405              410                 415
Pro Val Leu Asp Ser Asp Gly Ser Phe Phe Leu Val Ser Lys Leu Thr
            420                 425              430
Val Asp Lys Ser Arg Trp Gln Gln Gly Asn Val Phe Ser Cys Ser Val
            435                 440              445
Met His Glu Ala Leu His Asn His Tyr Thr Gln Lys Ser Leu Ser Leu
        450                 455              460
Ser Pro Gly Lys
465

<210> SEQ ID NO 20
<211> LENGTH: 469
<212> TYPE: PRT
<213> ORGANISM: Artificial Sequence
<220> FEATURE:
<223> OTHER INFORMATION: Anti-Her2(T)-Fc1 heavy chain amino acid
      sequence

<400> SEQUENCE: 20

Met Glu Trp Ser Trp Val Phe Leu Phe Phe Leu Ser Val Thr Thr Gly
1               5                   10                  15
Val His Ser Glu Val Gln Leu Val Glu Ser Gly Gly Gly Leu Val Gln
            20                  25                  30
Pro Gly Gly Ser Leu Arg Leu Ser Cys Ala Ala Ser Gly Phe Asn Ile
        35                  40                  45
Lys Asp Thr Tyr Ile His Trp Val Arg Gln Ala Pro Gly Lys Gly Leu
    50                  55                  60
```

```
Glu Trp Val Ala Arg Ile Tyr Pro Thr Asn Gly Tyr Thr Arg Tyr Ala
 65                  70                  75                  80

Asp Ser Val Lys Gly Arg Phe Thr Ile Ser Ala Asp Thr Ser Lys Asn
                 85                  90                  95

Thr Ala Tyr Leu Gln Met Asn Ser Leu Arg Ala Glu Asp Thr Ala Val
            100                 105                 110

Tyr Tyr Cys Ser Arg Trp Gly Asp Gly Phe Tyr Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Ser Cys Ala Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Val Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465
```

```
<210> SEQ ID NO 21
<211> LENGTH: 234
<212> TYPE: PRT
<213> ORGANISM: Artificial Sequence
<220> FEATURE:
<223> OTHER INFORMATION: Anti-Her2(T)-Fc1 light chain amino acid
      sequence

<400> SEQUENCE: 21

Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln His Tyr
            100                 105                 110

Thr Thr Pro Pro Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 22
<211> LENGTH: 468
<212> TYPE: PRT
<213> ORGANISM: Artificial Sequence
<220> FEATURE:
<223> OTHER INFORMATION: Anti-Her2(P)-Fc1 heavy chain amino acid
      sequence

<400> SEQUENCE: 22

Met Glu Trp Ser Trp Val Phe Leu Phe Phe Leu Ser Val Thr Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Asp Tyr Thr Met Asp Trp Val Arg Gln Ala Pro Gly Lys Gly Leu
    50                  55                  60

Glu Trp Val Ala Asp Val Asn Pro Asn Ser Gly Gly Ser Ile Tyr Asn
```

```
              65                  70                  75                  80
         Gln Arg Phe Lys Gly Arg Phe Thr Leu Ser Val Asp Arg Ser Lys Asn
                         85                  90                  95
         Thr Leu Tyr Leu Gln Met Asn Ser Leu Arg Ala Glu Asp Thr Ala Val
                         100                 105                 110
         Tyr Tyr Cys Ala Arg Asn Leu Gly Pro Ser Phe Tyr Phe Asp Tyr Trp
                         115                 120                 125
         Gly Gln Gly Thr Leu Val Thr Val Ser Ser Ala Ser Thr Lys Gly Pro
                         130                 135                 140
         Ser Val Phe Pro Leu Ala Pro Ser Ser Lys Ser Thr Ser Gly Gly Thr
         145                 150                 155                 160
         Ala Ala Leu Gly Cys Leu Val Lys Asp Tyr Phe Pro Glu Pro Val Thr
                         165                 170                 175
         Val Ser Trp Asn Ser Gly Ala Leu Thr Ser Gly Val His Thr Phe Pro
                         180                 185                 190
         Ala Val Leu Gln Ser Ser Gly Leu Tyr Ser Leu Ser Ser Val Val Thr
                         195                 200                 205
         Val Pro Ser Ser Ser Leu Gly Thr Gln Thr Tyr Ile Cys Asn Val Asn
                         210                 215                 220
         His Lys Pro Ser Asn Thr Lys Val Asp Lys Lys Val Glu Pro Lys Ser
         225                 230                 235                 240
         Cys Asp Lys Thr His Thr Cys Pro Pro Cys Pro Ala Pro Glu Leu Leu
                         245                 250                 255
         Gly Gly Pro Ser Val Phe Leu Phe Pro Pro Lys Pro Lys Asp Thr Leu
                         260                 265                 270
         Met Ile Ser Arg Thr Pro Glu Val Thr Cys Val Val Val Asp Val Ser
                         275                 280                 285
         His Glu Asp Pro Glu Val Lys Phe Asn Trp Tyr Val Asp Gly Val Glu
                         290                 295                 300
         Val His Asn Ala Lys Thr Lys Pro Arg Glu Glu Gln Tyr Asn Ser Thr
         305                 310                 315                 320
         Tyr Arg Val Val Ser Val Leu Thr Val Leu His Gln Asp Trp Leu Asn
                         325                 330                 335
         Gly Lys Glu Tyr Lys Cys Lys Val Ser Asn Lys Ala Leu Pro Ala Pro
                         340                 345                 350
         Ile Glu Lys Thr Ile Ser Lys Ala Lys Gly Gln Pro Arg Glu Pro Gln
                         355                 360                 365
         Val Tyr Thr Leu Pro Pro Ser Arg Asp Glu Leu Thr Lys Asn Gln Val
                         370                 375                 380
         Ser Leu Ser Cys Ala Val Lys Gly Phe Tyr Pro Ser Asp Ile Ala Val
         385                 390                 395                 400
         Glu Trp Glu Ser Asn Gly Gln Pro Glu Asn Asn Tyr Lys Thr Thr Pro
                         405                 410                 415
         Pro Val Leu Asp Ser Asp Gly Ser Phe Phe Leu Val Ser Lys Leu Thr
                         420                 425                 430
         Val Asp Lys Ser Arg Trp Gln Gln Gly Asn Val Phe Ser Cys Ser Val
                         435                 440                 445
         Met His Glu Ala Leu His Asn His Tyr Thr Gln Lys Ser Leu Ser Leu
                         450                 455                 460
         Ser Pro Gly Lys
         465

<210> SEQ ID NO 23
```

```
<211> LENGTH: 234
<212> TYPE: PRT
<213> ORGANISM: Artificial Sequence
<220> FEATURE:
<223> OTHER INFORMATION: Anti-Her2(P)-Fc1 light chain amino acid
      sequence

<400> SEQUENCE: 23

Met Ser Val Pro Thr Gln Val Gly Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Val Ser Ile Gly Val Ala Trp Tyr Gln Gln Lys Pro Gly Lys Ala Pro
    50                  55                  60

Lys Leu Leu Ile Tyr Ser Ala Ser Tyr Arg Tyr Thr Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Tyr Tyr
            100                 105                 110

Ile Tyr Pro Tyr Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 24
<211> LENGTH: 467
<212> TYPE: PRT
<213> ORGANISM: Artificial Sequence
<220> FEATURE:
<223> OTHER INFORMATION: Anti-PD-L1(Ate)-Fc1 heavy chain amino acid
      sequence

<400> SEQUENCE: 24

Met Glu Trp Ser Trp Val Phe Leu Phe Phe Leu Ser Val Thr Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asp Ser Trp Ile His Trp Val Arg Gln Ala Pro Gly Lys Gly Leu
    50                  55                  60

Glu Trp Val Ala Trp Ile Ser Pro Tyr Gly Gly Ser Thr Tyr Tyr Ala
65                  70                  75                  80
```

```
Asp Ser Val Lys Gly Arg Phe Thr Ile Ser Ala Asp Thr Ser Lys Asn
                85                  90                  95
Thr Ala Tyr Leu Gln Met Asn Ser Leu Arg Ala Glu Asp Thr Ala Val
            100                 105                 110
Tyr Tyr Cys Ala Arg Arg His Trp Pro Gly Gly Phe Asp Tyr Trp Gly
        115                 120                 125
Gln Gly Thr Leu Val Thr Val Ser Ser Ala Ser Thr Lys Gly Pro Ser
    130                 135                 140
Val Phe Pro Leu Ala Pro Ser Ser Lys Ser Thr Ser Gly Gly Thr Ala
145                 150                 155                 160
Ala Leu Gly Cys Leu Val Lys Asp Tyr Phe Pro Glu Pro Val Thr Val
                165                 170                 175
Ser Trp Asn Ser Gly Ala Leu Thr Ser Gly Val His Thr Phe Pro Ala
            180                 185                 190
Val Leu Gln Ser Ser Gly Leu Tyr Ser Leu Ser Ser Val Val Thr Val
        195                 200                 205
Pro Ser Ser Ser Leu Gly Thr Gln Thr Tyr Ile Cys Asn Val Asn His
    210                 215                 220
Lys Pro Ser Asn Thr Lys Val Asp Lys Val Glu Pro Lys Ser Cys
225                 230                 235                 240
Asp Lys Thr His Thr Cys Pro Pro Cys Pro Ala Pro Glu Leu Leu Gly
                245                 250                 255
Gly Pro Ser Val Phe Leu Phe Pro Pro Lys Pro Lys Asp Thr Leu Met
            260                 265                 270
Ile Ser Arg Thr Pro Glu Val Thr Cys Val Val Val Asp Val Ser His
        275                 280                 285
Glu Asp Pro Glu Val Lys Phe Asn Trp Tyr Val Asp Gly Val Glu Val
    290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
            340                 345                 350
Glu Lys Thr Ile Ser Lys Ala Lys Gly Gln Pro Arg Glu Pro Gln Val
        355                 360                 365
Tyr Thr Leu Pro Pro Ser Arg Asp Glu Leu Thr Lys Asn Gln Val Ser
    370                 375                 380
Leu Ser Cys Ala Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Val Ser Lys Leu Thr Val
            420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
    450                 455                 460
Pro Gly Lys
465

<210> SEQ ID NO 25
<211> LENGTH: 1641
```

<210> SEQ ID NO 25
<211> LENGTH: 1641
<212> TYPE: DNA
<213> ORGANISM: Artificial Sequence
<220> FEATURE:
<223> OTHER INFORMATION: D1-D2-D3-Fc2 DNA sequence

<400> SEQUENCE: 25

```
atggaatgga gctgggtgtt cctgttcttt ctgtccgtga ccacaggcgt gcattctgaa      60
gaggagctgc aggtcatcca gcccgataag agcgtgtccg tggccgcagg agaatctgcc    120
atcctgcatt gcaccgtgac ctctctgatc ccgtgggcc caatccagtg gttcagagga     180
gccggaccag ctagagagct gatctacaac agaaggagg ccacttccc cagagtgaca      240
accgtgtccg agtctaccaa gcgggagaac atggacttct ccatctccat ctccgccatc    300
acaccagccg acgccggcac ctactattgc gtgaagttcc ggaagggctc cccagatacc    360
gagtttaaga gcggcgccgg aacagagctg agcgtgcggg ctaagccttc tgctccagtg    420
gtgtcaggac cagcagctag agctacccct cagcacaccg tgtccttcac ctgcgagtct    480
cacggcttct cccctagaga catcacctc aagtggttca gaacggcaa cgagctgtcc      540
gacttccaga ccaacgtgga tccagtgggc gagagcgtgt cttactccat ccactccacc    600
gccaaggtgg tgctgacaag ggaggacgtg cactcccagg tcatttgcga ggtggcacac    660
gtgacattgc agggcgaccc cctgagaggc acagcaaact tgagcgagac aattagagtg    720
ccccccaccc tggaagttac acagcagccc gttagagccg agaaccaggt caacgtcacc    780
tgccaggtca gaaagtttta ccacagaga ctgcagctga cctggctcga aacggaaac     840
gtgagcagaa cagagaccgc cagcaccgtg acagagaaca aggacgggac ctacaactgg    900
atgagttggc tgctggtgaa cgtcagcgcc cacagagacg acgtcaagct gacctgcgac    960
aagacccaca cctgtccccc ttgtcctgcc cctgaactgc tgggcggacc ttccgtgttc   1020
ctgttccccc caaagcccaa ggacaccctg atgatctccc ggaccccga agtgacctgc    1080
gtggtggtgg atgtgtccca cgaggaccct gaagtgaagt tcaattggta cgtggacggc   1140
gtggaagtgc acaacgccaa gaccaagcct agagaggaac agtacaactc cacctaccgg   1200
gtggtgtccg tgctgaccgt gctgcaccag gattggctga acggcaaaga gtacaagtgc   1260
aaggtgtcca acaaggccct gcctgccccc atcgaaaaga ccatctccaa ggccaagggc   1320
cagccccggg aacccagt gtacacactg ccctagca gggacgagct gaccaagaac      1380
caggtgtccc tgtggtgtct cgtgaaaggc ttctacccct ccgacattgc cgtggaatgg   1440
gagtccaacg gccagcctga gaacaactac aagaccaccc ccctgtgct ggactccgac    1500
ggctcattct tcctgtacag caagctgaca gtggacaagt cccggtggca gcagggcaac   1560
gtgttctcct gctccgtgat gcacgaggcc ctgcacaacc actacaccca gaagtccctg   1620
tccctgagcc ccggcaaatg a                                             1641
```

<210> SEQ ID NO 26
<211> LENGTH: 363
<212> TYPE: PRT
<213> ORGANISM: Artificial Sequence
<220> FEATURE:
<223> OTHER INFORMATION: D1-Fc2 amino acid sequence

<400> SEQUENCE: 26

Met Glu Trp Ser Trp Val Phe Leu Phe Phe Leu Ser Val Thr Thr Gly
 1               5                  10                  15

Val His Ser Glu Glu Glu Leu Gln Val Ile Gln Pro Asp Lys Ser Val
            20                  25                  30

```
Ser Val Ala Ala Gly Glu Ser Ala Ile Leu His Cys Thr Val Thr Ser
         35                  40                  45
Leu Ile Pro Val Gly Pro Ile Gln Trp Phe Arg Gly Ala Gly Pro Ala
 50                  55                  60
Arg Glu Leu Ile Tyr Asn Gln Lys Glu Gly His Phe Pro Arg Val Thr
 65                  70                  75                  80
Thr Val Ser Glu Ser Thr Lys Arg Glu Asn Met Asp Phe Ser Ile Ser
                 85                  90                  95
Ile Ser Ala Ile Thr Pro Ala Asp Ala Gly Thr Tyr Tyr Cys Val Lys
                100                 105                 110
Phe Arg Lys Gly Ser Pro Asp Thr Glu Phe Lys Ser Gly Ala Gly Thr
            115                 120                 125
Glu Leu Ser Val Arg Ala Lys Pro Asp Lys Thr His Thr Cys Pro Pro
130                 135                 140
Cys Pro Ala Pro Glu Leu Leu Gly Gly Pro Ser Val Phe Leu Phe Pro
145                 150                 155                 160
Pro Lys Pro Lys Asp Thr Leu Met Ile Ser Arg Thr Pro Glu Val Thr
                165                 170                 175
Cys Val Val Val Asp Val Ser His Glu Asp Pro Glu Val Lys Phe Asn
                180                 185                 190
Trp Tyr Val Asp Gly Val Glu Val His Asn Ala Lys Thr Lys Pro Arg
            195                 200                 205
Glu Glu Gln Tyr Asn Ser Thr Tyr Arg Val Val Ser Val Leu Thr Val
210                 215                 220
Leu His Gln Asp Trp Leu Asn Gly Lys Glu Tyr Lys Cys Lys Val Ser
225                 230                 235                 240
Asn Lys Ala Leu Pro Ala Pro Ile Glu Lys Thr Ile Ser Lys Ala Lys
                245                 250                 255
Gly Gln Pro Arg Glu Pro Gln Val Tyr Thr Leu Pro Pro Ser Arg Asp
            260                 265                 270
Glu Leu Thr Lys Asn Gln Val Ser Leu Trp Cys Leu Val Lys Gly Phe
            275                 280                 285
Tyr Pro Ser Asp Ile Ala Val Glu Trp Glu Ser Asn Gly Gln Pro Glu
290                 295                 300
Asn Asn Tyr Lys Thr Thr Pro Pro Val Leu Asp Ser Asp Gly Ser Phe
305                 310                 315                 320
Phe Leu Tyr Ser Lys Leu Thr Val Asp Lys Ser Arg Trp Gln Gln Gly
                325                 330                 335
Asn Val Phe Ser Cys Ser Val Met His Glu Ala Leu His Asn His Tyr
            340                 345                 350
Thr Gln Lys Ser Leu Ser Leu Ser Pro Gly Lys
            355                 360

<210> SEQ ID NO 27
<211> LENGTH: 462
<212> TYPE: PRT
<213> ORGANISM: Artificial Sequence
<220> FEATURE:
<223> OTHER INFORMATION: D1-D2-Fc2 amino acid sequence

<400> SEQUENCE: 27

Met Glu Trp Ser Trp Val Phe Leu Phe Phe Leu Ser Val Thr Thr Gly
 1               5                  10                  15
Val His Ser Glu Glu Glu Leu Gln Val Ile Gln Pro Asp Lys Ser Val
             20                  25                  30
```

```
Ser Val Ala Ala Gly Glu Ser Ala Ile Leu His Cys Thr Val Thr Ser
         35                  40                  45

Leu Ile Pro Val Gly Pro Ile Gln Trp Phe Arg Gly Ala Gly Pro Ala
 50                  55                  60

Arg Glu Leu Ile Tyr Asn Gln Lys Glu Gly His Phe Pro Arg Val Thr
 65                  70                  75                  80

Thr Val Ser Glu Ser Thr Lys Arg Glu Asn Met Asp Phe Ser Ile Ser
                 85                  90                  95

Ile Ser Ala Ile Thr Pro Ala Asp Ala Gly Thr Tyr Tyr Cys Val Lys
                100                 105                 110

Phe Arg Lys Gly Ser Pro Asp Thr Glu Phe Lys Ser Gly Ala Gly Thr
            115                 120                 125

Glu Leu Ser Val Arg Ala Lys Pro Ser Ala Pro Val Val Ser Gly Pro
        130                 135                 140

Ala Ala Arg Ala Thr Pro Gln His Thr Val Ser Phe Thr Cys Glu Ser
145                 150                 155                 160

His Gly Phe Ser Pro Arg Asp Ile Thr Leu Lys Trp Phe Lys Asn Gly
                165                 170                 175

Asn Glu Leu Ser Asp Phe Gln Thr Asn Val Asp Pro Val Gly Glu Ser
            180                 185                 190

Val Ser Tyr Ser Ile His Ser Thr Ala Lys Val Val Leu Thr Arg Glu
        195                 200                 205

Asp Val His Ser Gln Val Ile Cys Glu Val Ala His Val Thr Leu Gln
210                 215                 220

Gly Asp Pro Leu Arg Gly Thr Ala Asn Leu Ser Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Trp Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
```

<210> SEQ ID NO 28
<211> LENGTH: 546
<212> TYPE: PRT
<213> ORGANISM: Artificial Sequence
<220> FEATURE:
<223> OTHER INFORMATION: D1-D2-D3-Fc2 amino acid sequence

<400> SEQUENCE: 28

Met Glu Trp Ser Trp Val Phe Leu Phe Phe Leu Ser Val Thr Thr Gly
1               5                   10                  15

Val His Ser Glu Glu Glu Leu Gln Val Ile Gln Pro Asp Lys Ser Val
            20                  25                  30

Ser Val Ala Ala Gly Glu Ser Ala Ile Leu His Cys Thr Val Thr Ser
        35                  40                  45

Leu Ile Pro Val Gly Pro Ile Gln Trp Phe Arg Gly Ala Gly Pro Ala
    50                  55                  60

Arg Glu Leu Ile Tyr Asn Gln Lys Glu Gly His Phe Pro Arg Val Thr
65                  70                  75                  80

Thr Val Ser Glu Ser Thr Lys Arg Glu Asn Met Asp Phe Ser Ile Ser
                85                  90                  95

Ile Ser Ala Ile Thr Pro Ala Asp Ala Gly Thr Tyr Tyr Cys Val Lys
            100                 105                 110

Phe Arg Lys Gly Ser Pro Asp Thr Glu Phe Lys Ser Gly Ala Gly Thr
        115                 120                 125

Glu Leu Ser Val Arg Ala Lys Pro Ser Ala Pro Val Val Ser Gly Pro
130                 135                 140

Ala Ala Arg Ala Thr Pro Gln His Thr Val Ser Phe Thr Cys Glu Ser
145                 150                 155                 160

His Gly Phe Ser Pro Arg Asp Ile Thr Leu Lys Trp Phe Lys Asn Gly
                165                 170                 175

Asn Glu Leu Ser Asp Phe Gln Thr Asn Val Asp Pro Val Gly Glu Ser
            180                 185                 190

Val Ser Tyr Ser Ile His Ser Thr Ala Lys Val Val Leu Thr Arg Glu
        195                 200                 205

Asp Val His Ser Gln Val Ile Cys Glu Val Ala His Val Thr Leu Gln
    210                 215                 220

Gly Asp Pro Leu Arg Gly Thr Ala Asn Leu Ser Glu Thr Ile Arg Val
225                 230                 235                 240

Pro Pro Thr Leu Glu Val Thr Gln Gln Pro Val Arg Ala Glu Asn Gln
                245                 250                 255

Val Asn Val Thr Cys Gln Val Arg Lys Phe Tyr Pro Gln Arg Leu Gln
            260                 265                 270

Leu Thr Trp Leu Glu Asn Gly Asn Val Ser Arg Thr Glu Thr Ala Ser
        275                 280                 285

Thr Val Thr Glu Asn Lys Asp Gly Thr Tyr Asn Trp Met Ser Trp Leu
    290                 295                 300

Leu Val Asn Val Ser Ala His Arg Asp Asp Val Lys Leu Thr Cys Asp
305                 310                 315                 320

Lys Thr His Thr Cys Pro Pro Cys Pro Ala Pro Glu Leu Leu Gly Gly
                325                 330                 335

Pro Ser Val Phe Leu Phe Pro Pro Lys Pro Lys Asp Thr Leu Met Ile
            340                 345                 350

Ser Arg Thr Pro Glu Val Thr Cys Val Val Val Asp Val Ser His Glu

-continued

```
                355                 360                 365
Asp Pro Glu Val Lys Phe Asn Trp Tyr Val Asp Gly Val Glu Val His
370                 375                 380
Asn Ala Lys Thr Lys Pro Arg Glu Glu Gln Tyr Asn Ser Thr Tyr Arg
385                 390                 395                 400
Val Val Ser Val Leu Thr Val Leu His Gln Asp Trp Leu Asn Gly Lys
                405                 410                 415
Glu Tyr Lys Cys Lys Val Ser Asn Lys Ala Leu Pro Ala Pro Ile Glu
                420                 425                 430
Lys Thr Ile Ser Lys Ala Lys Gly Gln Pro Arg Glu Pro Gln Val Tyr
                435                 440                 445
Thr Leu Pro Pro Ser Arg Asp Glu Leu Thr Lys Asn Gln Val Ser Leu
                450                 455                 460
Trp Cys Leu Val Lys Gly Phe Tyr Pro Ser Asp Ile Ala Val Glu Trp
465                 470                 475                 480
Glu Ser Asn Gly Gln Pro Glu Asn Asn Tyr Lys Thr Thr Pro Pro Val
                485                 490                 495
Leu Asp Ser Asp Gly Ser Phe Phe Leu Tyr Ser Lys Leu Thr Val Asp
                500                 505                 510
Lys Ser Arg Trp Gln Gln Gly Asn Val Phe Ser Cys Ser Val Met His
                515                 520                 525
Glu Ala Leu His Asn His Tyr Thr Gln Lys Ser Leu Ser Leu Ser Pro
530                 535                 540

Gly Lys
545

<210> SEQ ID NO 29
<211> LENGTH: 369
<212> TYPE: PRT
<213> ORGANISM: Artificial Sequence
<220> FEATURE:
<223> OTHER INFORMATION: D1m-Fc2 amino acid sequence

<400> SEQUENCE: 29

Met Glu Trp Ser Trp Val Phe Leu Phe Phe Leu Ser Val Thr Thr Gly
1               5                   10                  15
Val His Ser Glu Glu Glu Leu Gln Ile Ile Gln Pro Asp Lys Ser Val
                20                  25                  30
Ser Val Ala Ala Gly Glu Ser Ala Ile Leu His Cys Thr Ile Thr Ser
                35                  40                  45
Leu Phe Pro Val Gly Pro Ile Gln Trp Phe Arg Gly Ala Gly Pro Ala
                50                  55                  60
Arg Val Leu Ile Tyr Asn Gln Arg Gln Gly Pro Phe Pro Arg Val Thr
65                  70                  75                  80
Thr Val Ser Glu Thr Thr Lys Arg Glu Asn Met Asp Phe Ser Ile Ser
                85                  90                  95
Ile Ser Asn Ile Thr Pro Ala Asp Ala Gly Thr Tyr Tyr Cys Ile Lys
                100                 105                 110
Phe Arg Lys Gly Ser Pro Asp Thr Glu Phe Lys Ser Gly Ala Gly Thr
                115                 120                 125
Glu Leu Ser Val Arg Ala Lys Pro Ser Glu Pro Lys Ser Ser Asp Lys
                130                 135                 140
Thr His Thr Cys Pro Pro Cys Pro Ala Pro Glu Leu Leu Gly Gly Pro
145                 150                 155                 160
Ser Val Phe Leu Phe Pro Pro Lys Pro Lys Asp Thr Leu Met Ile Ser
```

```
                    165                 170                 175
Arg Thr Pro Glu Val Thr Cys Val Val Asp Val Ser His Glu Asp
            180                 185                 190

Pro Glu Val Lys Phe Asn Trp Tyr Val Asp Gly Val Glu Val His Asn
            195                 200                 205

Ala Lys Thr Lys Pro Arg Glu Glu Gln Tyr Asn Ser Thr Tyr Arg Val
            210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Ala Pro Ile Glu Lys
                245                 250                 255

Thr Ile Ser Lys Ala Lys Gly Gln Pro Arg Glu Pro Gln Val Tyr Thr
                260                 265                 270

Leu Pro Pro Ser Arg Asp Glu Leu Thr Lys Asn Gln Val Ser Leu Trp
                275                 280                 285

Cys Leu Val Lys Gly Phe Tyr Pro Ser Asp Ile Ala Val Glu Trp Glu
290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
                340                 345                 350

Ala Leu His Asn His Tyr Thr Gln Lys Ser Leu Ser Leu Ser Pro Gly
                355                 360                 365

Lys

<210> SEQ ID NO 30
<211> LENGTH: 117
<212> TYPE: PRT
<213> ORGANISM: Artificial Sequence
<220> FEATURE:
<223> OTHER INFORMATION: D1 amino acid sequence

<400> SEQUENCE: 30

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
50              55                  60

Glu Ser Thr Lys Arg Glu Asn Met Asp Phe Ser Ile Ser Ile Ser Ala
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro
        115

<210> SEQ ID NO 31
<211> LENGTH: 216
<212> TYPE: PRT
<213> ORGANISM: Artificial Sequence
```

```
<220> FEATURE:
<223> OTHER INFORMATION: D1-D2 amino acid sequence

<400> SEQUENCE: 31

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
                20                  25                  30

Val Gly Pro Ile Gln Trp Phe Arg Gly Ala Gly Pro Ala Arg Glu Leu
            35                  40                  45

Ile Tyr Asn Gln Lys Glu Gly His Phe Pro Arg Val Thr Thr Val Ser
        50                  55                  60

Glu Ser Thr Lys Arg Glu Asn Met Asp Phe Ser Ile Ser Ile Ser Ala
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Ala Pro Val Val Ser Gly Pro Ala Ala Arg
        115                 120                 125

Ala Thr Pro Gln His Thr Val Ser Phe Thr Cys Glu Ser His Gly Phe
    130                 135                 140

Ser Pro Arg Asp Ile Thr Leu Lys Trp Phe Lys Asn Gly Asn Glu Leu
145                 150                 155                 160

Ser Asp Phe Gln Thr Asn Val Asp Pro Val Gly Glu Ser Val Ser Tyr
                165                 170                 175

Ser Ile His Ser Thr Ala Lys Val Val Leu Thr Arg Glu Asp Val His
            180                 185                 190

Ser Gln Val Ile Cys Glu Val Ala His Val Thr Leu Gln Gly Asp Pro
        195                 200                 205

Leu Arg Gly Thr Ala Asn Leu Ser
    210                 215

<210> SEQ ID NO 32
<211> LENGTH: 300
<212> TYPE: PRT
<213> ORGANISM: Artificial Sequence
<220> FEATURE:
<223> OTHER INFORMATION: D1-D2-D3 amino acid sequence

<400> SEQUENCE: 32

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
                20                  25                  30

Val Gly Pro Ile Gln Trp Phe Arg Gly Ala Gly Pro Ala Arg Glu Leu
            35                  40                  45

Ile Tyr Asn Gln Lys Glu Gly His Phe Pro Arg Val Thr Thr Val Ser
        50                  55                  60

Glu Ser Thr Lys Arg Glu Asn Met Asp Phe Ser Ile Ser Ile Ser Ala
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Ala Pro Val Val Ser Gly Pro Ala Ala Arg
```

```
                  115                 120                 125
Ala Thr Pro Gln His Thr Val Ser Phe Thr Cys Glu Ser His Gly Phe
    130                 135                 140

Ser Pro Arg Asp Ile Thr Leu Lys Trp Phe Lys Asn Gly Asn Glu Leu
145                 150                 155                 160

Ser Asp Phe Gln Thr Asn Val Asp Pro Val Gly Glu Ser Val Ser Tyr
                165                 170                 175

Ser Ile His Ser Thr Ala Lys Val Val Leu Thr Arg Glu Asp Val His
                180                 185                 190

Ser Gln Val Ile Cys Glu Val Ala His Val Thr Leu Gln Gly Asp Pro
            195                 200                 205

Leu Arg Gly Thr Ala Asn Leu Ser Glu Thr Ile Arg Val Pro Pro Thr
    210                 215                 220

Leu Glu Val Thr Gln Gln Pro Val Arg Ala Glu Asn Gln Val Asn Val
225                 230                 235                 240

Thr Cys Gln Val Arg Lys Phe Tyr Pro Gln Arg Leu Gln Leu Thr Trp
                245                 250                 255

Leu Glu Asn Gly Asn Val Ser Arg Thr Glu Thr Ala Ser Thr Val Thr
                260                 265                 270

Glu Asn Lys Asp Gly Thr Tyr Asn Trp Met Ser Trp Leu Leu Val Asn
            275                 280                 285

Val Ser Ala His Arg Asp Asp Val Lys Leu Thr Cys
    290                 295                 300

<210> SEQ ID NO 33
<211> LENGTH: 123
<212> TYPE: PRT
<213> ORGANISM: Artificial Sequence
<220> FEATURE:
<223> OTHER INFORMATION: D1m amino acid sequence

<400> SEQUENCE: 33

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Glu Pro Lys Ser Ser
        115                 120

<210> SEQ ID NO 34
<211> LENGTH: 1416
<212> TYPE: DNA
<213> ORGANISM: Artificial Sequence
<220> FEATURE:
<223> OTHER INFORMATION: Ofa-Fc1 heavy chain DNA sequence

<400> SEQUENCE: 34
```

| | |
|---|---:|
| atggaatgga gctgggtgtt cctgttcttt ctgtccgtga ccacaggcgt gcattctgaa | 60 |
| gtgcagctgg tggaatctgg cggcggactg gtgcagcctg gcagatccct gagactgtct | 120 |
| tgtgccgcct ccggcttcac cttcaacgac tacgccatgc actgggtgcg acaggcccct | 180 |
| ggcaaaggcc tggaatgggt gtccaccatc agctggaact ccggctccat cggctacgcc | 240 |
| gactccgtga agggccggtt caccatctcc cgggacaacg ccaagaagtc cctgtacctg | 300 |
| cagatgaact ccctgcgggc cgaggacacc gccctgtact actgtgccaa ggacatccag | 360 |
| tacggcaact actactacgg catggacgtg tggggccagg gcaccacagt gaccgtgtca | 420 |
| tctgcttcta ccaagggccc ctccgtgttt cctctggccc cttccagcaa gtccacctct | 480 |
| ggcggaacag ccgctctggg ctgcctcgtg aaggactact ccccgagcc tgtgaccgtg | 540 |
| tcctggaact ctggcgctct gacatccggc gtgcacacct tccctgctgt gctgcagtct | 600 |
| agcggcctgt actccctgtc ctccgtcgtg accgtgcctt ccagctctct gggcacccag | 660 |
| acctacatct gcaacgtgaa ccacaagccc tccaacacca aggtggacaa gaaggtggaa | 720 |
| cccaagtcct gcgacaagac ccacacctgt cccccttgtc ctgcccctga actgctgggc | 780 |
| ggaccttccg tgttcctgtt cccccccaaag cccaaggaca ccctgatgat ctcccggacc | 840 |
| cccgaagtga cctgcgtggt ggtggatgtg tcccacgagg accctgaagt gaagttcaat | 900 |
| tggtacgtgg acggcgtgga agtgcacaac gccaagacca gcctagaga ggaacagtac | 960 |
| aactccacct accgggtggt gtccgtgctg accgtgctgc accaggattg gctgaacggc | 1020 |
| aaagagtaca gtgcaaggt gtccaacaag gccctgcctg cccccatcga aaagaccatc | 1080 |
| tccaaggcca agggccagcc ccgggaaccc caggtgtaca cactgccccc tagcagggac | 1140 |
| gagctgacca gaaccaggt gtccctgagc tgtgcagtga aggcttcta ccctccgac | 1200 |
| attgccgtgg aatgggagtc caacggccag cctgagaaca actacaagac cacccccct | 1260 |
| gtgctggact ccgacggctc attcttcctg gtgagcaagc tgacagtgga caagtcccgg | 1320 |
| tggcagcagg gcaacgtgtt ctcctgctcc gtgatgcacg aggccctgca caaccactac | 1380 |
| acccagaagt ccctgtccct gagccccggc aaatga | 1416 |

<210> SEQ ID NO 35
<211> LENGTH: 705
<212> TYPE: DNA
<213> ORGANISM: Artificial Sequence
<220> FEATURE:
<223> OTHER INFORMATION: Ofa-Fc1 light chain DNA sequence

<400> SEQUENCE: 35

| | |
|---|---:|
| atgtctgtgc ctacccaggt gctgggactg ctgctgctgt ggctgacaga cgcccgctgt | 60 |
| gagatcgtgc tgacccagtc tcctgccacc ctgtctctga ccctggcga gagagctacc | 120 |
| ctgtcctgca gagcctccca gtccgtgtcc tcttacctgg cctggtatca gcagaagccc | 180 |
| ggccaggctc cccggctgct gatctacgat gcctccaata gagccaccgg catccctgcc | 240 |
| agattctccg gctctggctc tggcaccgac tttaccctga ccatctccag cctggaaccc | 300 |
| gaggacttcg ccgtgtacta ctgccagcag cggtccaact ggcccatcac ctttggccag | 360 |
| ggcacccggc tggaaatcaa agaaccgtg gccgctccct ccgtgttcat cttcccacct | 420 |
| tccgacgagc agctgaagtc cggcaccgct tctgtcgtgt gcctgctgaa caacttctac | 480 |
| ccccgcgagg ccaaggtgca gtggaaggtg gacaacgccc tgcagtccgg caactcccag | 540 |
| gaatccgtga ccgagcagga ctccaaggac agcacctact ccctgtcctc caccctgacc | 600 |
| ctgtccaagg ccgactacga aaagcacaag gtgtacgcct gcgaagtgac ccaccagggc | 660 |

```
ctgtctagcc ccgtgaccaa gtctttcaac cggggcgagt gctga              705
```

<210> SEQ ID NO 36
<211> LENGTH: 1407
<212> TYPE: DNA
<213> ORGANISM: Artificial Sequence
<220> FEATURE:
<223> OTHER INFORMATION: Obi-Fc1 heavy chain DNA sequence

<400> SEQUENCE: 36

```
atggaatgga gctgggtgtt cctgttcttt ctgtccgtga ccacaggcgt gcattctcag    60
gtgcagctgg tgcagtctgg cgccgaagtg aagaaacccg gctcctccgt gaaggtgtcc   120
tgcaaggctt ccggctacgc cttctcctac cctggatca actgggtgcg acaggcccct    180
ggacagggcc tggaatggat gggcagaatc ttccctggcg acggcgacac cgactacaac   240
ggcaagttca agggcagagt gaccatcacc gccgacaagt ccacctccac cgcctacatg   300
gaactgtcct ccctgcggag cgaggacacc gccgtgtact actgcgcccg gaacgtgttc   360
gacggctact ggctggtgta ttggggccag ggcaccctcg tgaccgtgtc ctctgcttct   420
accaagggcc cctccgtgtt cctctggcc ccttccagca gtccacctc tggcggaaca    480
gccgctctgg gctgcctcgt gaaggactac ttccccgagc ctgtgaccgt gcctggaac    540
tctggcgctc tgacatccgg cgtgcacacc ttccctgctg tgctgcagtc tagcggcctg   600
tactccctgt cctccgtcgt gaccgtgcct tccagctctc tgggcaccca gacctacatc   660
tgcaacgtga accacaagcc ctccaacacc aaggtggaca gaaaggtgga acccaagtcc   720
tgcgacaaga cccacacctg tccccttgt cctgccctg aactgctggg cggaccttcc    780
gtgttcctgt ccccccaaa gcccaaggac accctgatga tctcccggac ccccgaagtg   840
acctgcgtgg tggtggatgt gtcccacgag gaccctgaag tgaagttcaa ttggtacgtg   900
gacggcgtgg aagtgcacaa cgccaagacc aagcctagag aggaacagta caactccacc   960
tacaggtgg tgtccgtgct gaccgtgctg caccaggatt ggctgaacgg caaagagtac  1020
aagtgcaagg tgtccaacaa ggcctgcct gcccccatcg aaaagaccat ctccaaggcc  1080
aagggccagc ccgggaacc ccaggtgtac acactgcccc tagcaggga cgagctgacc   1140
aagaaccagg tgtccctgtc ctgtgctgtg aaaggcttct acccctccga cattgccgtg  1200
gaatgggagt ccaacggcca gcctgagaac aactacaaga ccacccccc tgtgctggac   1260
tccgacggct cattcttcct ggtgagcaag ctgacagtgg acaagtcccg gtggcagcag   1320
ggcaacgtgt tctcctgctc cgtgatgcac gaggccctgc acaaccacta cacccagaag   1380
tccctgtccc tgagccccgg caaatga                                       1407
```

<210> SEQ ID NO 37
<211> LENGTH: 1407
<212> TYPE: DNA
<213> ORGANISM: Artificial Sequence
<220> FEATURE:
<223> OTHER INFORMATION: Anti-EGFR-Fc1 heavy chain DNA sequence

<400> SEQUENCE: 37

```
atggaatgga gctgggtgtt cctgttctt ctgtccgtga ccacaggcgt gcattctcag     60
gtccagctcc aggaaagcgg ccccggcctc gtcaaaccct ccgagacact ctccctcaca   120
tgcacagtct ccggcttctc cctcagcaac tacgacgtcc actgggtcag acaggccccc   180
ggcaaaggac tggaatggct cggcgtcatc tggtccggcg gaaacaccga ctacaacacc  240
```

```
ccattcacct ccaggctcac catctccgtg gacacctcca agaaccagtt ctccctcaaa    300
ctgagctccg tgaccgccgc cgacaccgct gtctattatt gcgccagagc cctcgactac    360
tacgactacg aattcgccta ctggggccag ggcaccctgg tgaccgtgtc atctgcttct    420
accaagggcc cctccgtgtt tcctctggcc ccttccagca agtccacctc tggcggaaca    480
gccgctctgg gctgcctcgt gaaggactac ttccccgagc ctgtgaccgt gtcctggaac    540
tctggcgctc tgacatccgg cgtgcacacc ttccctgctg tgctgcagtc tagcggcctg    600
tactccctgt cctccgtcgt gaccgtgcct tccagctctc tgggcaccca gacctacatc    660
tgcaacgtga accacaagcc ctccaacacc aaggtggaca gaaaggtgga acccaagtcc    720
tgcgacaaga cccacacctg tcccccttgt cctgcccctg aactgctggg cggaccttcc    780
gtgttcctgt ccccccaaa gcccaaggac accctgatga tctcccggac ccccgaagtg    840
acctgcgtgg tggtggatgt gtcccacgag gaccctgaag tgaagttcaa ttggtacgtg    900
gacggcgtgg aagtgcacaa cgccaagacc aagcctagag aggaacagta caactccacc    960
taccgggtgg tgtccgtgct gaccgtgctg caccaggatt ggctgaacgg caaagagtac   1020
aagtgcaagg tgtccaacaa ggcccctgcct gccccccatcg aaaagaccat ctccaaggcc   1080
aagggccagc cccgggaacc ccaggtgtac acactgcccc ctagcaggga cgagctgacc   1140
aagaaccagg tgtccctgag ctgtgcagtg aaaggcttct acccctccga cattgccgtg   1200
gaatgggagt ccaacggcca gcctgagaac aactacaaga ccacccccc tgtgctggac   1260
tccgacggct cattcttcct ggtgagcaag ctgacagtgg acaagtcccg gtggcagcag   1320
ggcaacgtgt tctcctgctc cgtgatgcac gaggccctgc acaaccacta cacccagaag   1380
tccctgtccc tgagccccgg caaatga                                       1407
```

<210> SEQ ID NO 38
<211> LENGTH: 1410
<212> TYPE: DNA
<213> ORGANISM: Artificial Sequence
<220> FEATURE:
<223> OTHER INFORMATION: Anti-Her2(T)-Fc1 heavy chain DNA sequence

<400> SEQUENCE: 38

```
atggaatgga gctgggtgtt cctgttcttt ctgtccgtga ccacaggcgt gcattctgag     60
gtgcagttgg tggagagcgg ggggggggctg gtgcagcctg gaggaagttt gaggttgagc    120
tgtgccgcaa gcgggttcaa cattaaggac acatacattc actgggtgag gcaggcaccc    180
ggaaagggac tggagtgggt ggctaggatc taccccacca acggctacac aaggtacgcc    240
gacagtgtga agggccggtt caccatttcc gccgacacct ccaagaacac cgcctacctg    300
cagatgaaca gcctgagggc cgaggacacc gccgtctact actgctccag gtggggagga    360
gacggattct atgctatgga ctactgggga cagggcaccc tggtgaccgt gtcatctgct    420
tctaccaagg gccctccgt gtttcctctg ccccttcca gcaagtccac ctctggcgga    480
acagccgctc tgggctgcct cgtgaaggac tacttccccg agcctgtgac cgtgtcctgg    540
aactctggcg ctctgacatc cggcgtgcac accttccctg ctgtgctgca gtctagcggc    600
ctgtactccc tgtcctccgt cgtgaccgtg ccttccagct ctctgggcac ccagacctac    660
atctgcaacg tgaaccacaa gccctccaac accaaggtgg acaagaaggt ggaacccaag    720
tcctgcgaca agacccacac ctgtccccct tgtcctgccc ctgaactgct gggcggacct    780
tccgtgttcc tgttccccccc aaagcccaag gacaccctga tgatctcccg gacccccgaa    840
gtgacctgcg tggtggtgga tgtgtcccac gaggaccctg aagtgaagtt caattggtac    900
```

| | |
|---|---|
| gtggacggcg tggaagtgca caacgccaag accaagccta gagaggaaca gtacaactcc | 960 |
| acctaccggg tggtgtccgt gctgaccgtg ctgcaccagg attggctgaa cggcaaagag | 1020 |
| tacaagtgca aggtgtccaa caaggccctg cctgccccca tcgaaaagac catctccaag | 1080 |
| gccaagggcc agccccggga accccaggtg tacacactgc cccctagcag ggacgagctg | 1140 |
| accaagaacc aggtgtccct gagctgtgca gtgaaaggct tctacccctc cgacattgcc | 1200 |
| gtggaatggg agtccaacgg ccagcctgag aacaactaca agaccacccc ccctgtgctg | 1260 |
| gactccgacg gctcattctt cctggtgagc aagctgacag tggacaagtc ccggtggcag | 1320 |
| cagggcaacg tgttctcctg ctccgtgatg cacgaggccc tgcacaacca ctacacccag | 1380 |
| aagtccctgt ccctgagccc cggcaaatga | 1410 |

<210> SEQ ID NO 39
<211> LENGTH: 705
<212> TYPE: DNA
<213> ORGANISM: Artificial Sequence
<220> FEATURE:
<223> OTHER INFORMATION: Anti-Her2(T)-Fc1 light chain DNA sequence

<400> SEQUENCE: 39

| | |
|---|---|
| atgtctgtgc ctacccaggt gctgggactg ctgctgctgt ggctgacaga cgcccgctgt | 60 |
| gacattcaga tgacccagag ccctcctcc ctctccgcct ccgtgggaga cagagttacc | 120 |
| atcacctgca gggcctccca ggacgtgaac accgccgtgg cctggtacca gcagaaaccc | 180 |
| ggcaaagccc ccaaactgct catctactcc gcctcatttc tgtacagcgg cgtgccctcc | 240 |
| cgcttctccg gttccagatc cggcaccgac ttcaccctga ctatctcctc cctccagccc | 300 |
| gaagacttcg ccacctacta ctgccagcag cactacacca cccccccac cttcggccag | 360 |
| ggcacaaagg tcgaaatcaa gagaaccgtg gccgctccct ccgtgttcat cttcccacct | 420 |
| tccgacgagc agctgaagtc cggcaccgct tctgtcgtgt gcctgctgaa caacttctac | 480 |
| ccccgcgagg ccaaggtgca gtggaaggtg gacaacgccc tgcagtccgg caactcccag | 540 |
| gaatccgtga ccgagcagga ctccaaggac agcacctact ccctgtcctc caccctgacc | 600 |
| ctgtccaagg ccgactacga aagcacaag gtgtacgcct gcgaagtgac ccaccagggc | 660 |
| ctgtctagcc ccgtgaccaa gtctttcaac cggggcgagt gctga | 705 |

<210> SEQ ID NO 40
<211> LENGTH: 1407
<212> TYPE: DNA
<213> ORGANISM: Artificial Sequence
<220> FEATURE:
<223> OTHER INFORMATION: Anti-Her2(P)-Fc1 heavy chain DNA sequence

<400> SEQUENCE: 40

| | |
|---|---|
| atggaatgga gctgggtgtt cctgttcttt ctgtccgtga ccacaggcgt gcattctgag | 60 |
| gtgcagttgg tggagagcgg ggggggctg gtgcagcctg gaggaagttt gaggttgagc | 120 |
| tgtgccgcaa gcgggttcac atttacagac tacaatgg actgggtgag gcaggcaccc | 180 |
| ggaaagggac tggagtgggt ggctgatgtg aatcccaata gcggagggag catttacaac | 240 |
| cagagattca ggggcggtt caccttgtcc gtggacagga gcaagaacac actgtacctg | 300 |
| cagatgaaca gcctgagggc cgaggatacc gccgtctact attgcgccag gaacctcgga | 360 |
| ccctccttct attttgacta ctggggccag ggaaccctgg tgaccgtgtc atctgcttct | 420 |
| accaagggcc cctccgtgtt tcctctggcc ccttccagca gtccaccctc tggcggaaca | 480 |

| | |
|---|---|
| gccgctctgg gctgcctcgt gaaggactac ttccccgagc ctgtgaccgt gtcctggaac | 540 |
| tctggcgctc tgacatccgg cgtgcacacc ttccctgctg tgctgcagtc tagcggcctg | 600 |
| tactccctgt cctccgtcgt gaccgtgcct tccagctctc tgggcaccca gacctacatc | 660 |
| tgcaacgtga accacaagcc ctccaacacc aaggtggaca agaaggtgga acccaagtcc | 720 |
| tgcgacaaga cccacacctg tccccttgt cctgcccctg aactgctggg cggaccttcc | 780 |
| gtgttcctgt tccccccaaa gcccaaggac accctgatga tctcccggac ccccgaagtg | 840 |
| acctgcgtgg tggtggatgt gtcccacgag gaccctgaag tgaagttcaa ttggtacgtg | 900 |
| gacggcgtgg aagtgcacaa cgccaagacc aagcctagag aggaacagta caactccacc | 960 |
| taccgggtgg tgtccgtgct gaccgtgctg caccaggatt ggctgaacgg caaagagtac | 1020 |
| aagtgcaagg tgtccaacaa ggccctgcct gcccccatcg aaaagaccat ctccaaggcc | 1080 |
| aagggccagc cccgggaacc ccaggtgtac acactgcccc ctagcaggga cgagctgacc | 1140 |
| aagaaccagg tgtccctgag ctgtgcagtg aaaggcttct accctccga cattgccgtg | 1200 |
| gaatgggagt ccaacggcca gcctgagaac aactacaaga ccaccccccc tgtgctggac | 1260 |
| tccgacggct cattcttcct ggtgagcaag ctgacagtgg acaagtcccg gtggcagcag | 1320 |
| ggcaacgtgt tctcctgctc cgtgatgcac gaggccctgc acaaccacta cacccagaag | 1380 |
| tccctgtccc tgagccccgg caaatga | 1407 |

<210> SEQ ID NO 41
<211> LENGTH: 705
<212> TYPE: DNA
<213> ORGANISM: Artificial Sequence
<220> FEATURE:
<223> OTHER INFORMATION: Anti-Her2(P)-Fc1 light chain DNA sequence

<400> SEQUENCE: 41

| | |
|---|---|
| atgtctgtgc tacccaggt gctgggactg ctgctgctgt ggctgacaga cgcccgctgt | 60 |
| gacattcaga tgacccagag ccccctcctcc ctctccgcct ccgtgggaga cagagttacc | 120 |
| atcacctgca aagccagcca ggacgtgagc atcggcgtgg cctggtacca gcagaaaccc | 180 |
| ggcaaagccc ccaaactgct catttactcc gcctcatacc gttacaccgg cgttccctcc | 240 |
| cgcttcagcg gatccggctc cggaaccgac ttcaccctga ctatctcctc cctccagccc | 300 |
| gaagacttcg ccacctacta ctgccagcag tactacattt accccctacac cttcggccag | 360 |
| ggcaccaagg tggaaatcaa gagaaccgtg gccgctccct ccgtgttcat cttcccacct | 420 |
| tccgacgagc agctgaagtc cggcaccgct tctgtcgtgt gcctgctgaa caacttctac | 480 |
| cccccgcgagg ccaaggtgca gtggaaggtg gacaacgccc tgcagtccgg caactcccag | 540 |
| gaatccgtga ccgagcagga ctccaaggac agcacctact ccctgtcctc caccctgacc | 600 |
| ctgtccaagg ccgactacga aagcacaag gtgtacgcct gcgaagtgac ccaccagggc | 660 |
| ctgtctagcc ccgtgaccaa gtctttcaac cggggcgagt gctga | 705 |

<210> SEQ ID NO 42
<211> LENGTH: 1404
<212> TYPE: DNA
<213> ORGANISM: Artificial Sequence
<220> FEATURE:
<223> OTHER INFORMATION: Anti-PD-L1(Ate)-Fc1 heavy chain DNA sequence

<400> SEQUENCE: 42

| | |
|---|---|
| atggaatgga gctgggtgtt cctgttctt ctgtccgtga ccacaggcgt gcattctgaa | 60 |
| gtgcagctgg tggaaagcgg cggcggcctg gtgcagccgg gcggcagcct gcgcctgagc | 120 |

```
tgcgcggcga gcggctttac ctttagcgat agctggattc attgggtgcg ccaggcgccg      180
ggcaaaggcc tggaatgggt ggcgtggatt agcccgtatg gcggcagcac ctattatgcg      240
gatagcgtga aaggccgctt taccattagc gcggatacca gcaaaaacac cgcgtatctg      300
cagatgaaca gcctgcgcgc ggaagatacc gcggtgtatt attgcgcgcg ccgccattgg      360
ccgggcggct ttgattactg gggccagggc accctggtga ccgtgtcatc tgcttctacc      420
aagggcccct ccgtgtttcc tctggcccct ccagcaagt ccacctctgg cggaacagcc       480
gctctgggct gcctcgtgaa ggactacttc cccgagcctg tgaccgtgtc ctggaactct      540
ggcgctctga catccggcgt gcacaccttc cctgctgtgc tgcagtctag cggcctgtac      600
tccctgtcct ccgtcgtgac cgtgccttcc agctctctgg cacccagac ctacatctgc       660 aacgtgaacc acaagccctc caacaccaag gtggacaaga aggtggaacc caagtcctgc     720
gacaagaccc acacctgtcc cccttgtcct gcccctgaac tgctgggcgg accttccgtg      780
ttcctgttcc ccccaaagcc caaggacacc ctgatgatct cccggacccc cgaagtgacc      840
tgcgtggtgg tggatgtgtc ccacgaggac cctgaagtga agttcaattg gtacgtggac      900
ggcgtggaag tgcacaacgc caagaccaag cctagagagg aacagtacaa ctccacctac     960
cgggtggtgt ccgtgctgac cgtgctgcac caggattggc tgaacggcaa agagtacaag     1020
tgcaaggtgt ccaacaaggc cctgcctgcc cccatcgaaa agaccatctc caaggccaag     1080
ggccagcccc gggaacccca ggtgtacaca ctgcccccta gcagggacga gctgaccaag     1140
aaccaggtgt ccctgagctg tgcagtgaaa ggcttctacc cctccgacat tgccgtggaa     1200
tgggagtcca acggccagcc tgagaacaac tacaagacca ccccccctgt gctggactcc     1260
gacggctcat tcttcctggt gagcaagctg acagtggaca agtccggtg gcagcagggc     1320 aacgtgttct cctgctccgt gatgcacgag gccctgcaca accactacac ccagaagtcc     1380
ctgtccctga gccccggcaa atga                                            1404

<210> SEQ ID NO 43
<211> LENGTH: 1110
<212> TYPE: DNA
<213> ORGANISM: Artificial Sequence
<220> FEATURE:
<223> OTHER INFORMATION: D1m-Fc2 DNA sequence

<400> SEQUENCE: 43
atggagtgga gctgggtgtt cttgttcttc ttgtccgtga ccaccggggt gcacagcgag       60
gaggagttgc agatcatcca gcctgacaag agcgtgagcg tggccgccgg ggagagcgct     120
attctgcact gtaccatcac ctccctcttc cccgtgggcc ccattcagtg gttcaggga     180 gccgggcccg ccagagttct gatttacaac cagaggcagg ccccctttcc ccgggttacc     240
actgtctctg agaccaccaa gcgggagaac atggatttca gcatctccat cagcaacatt     300
actcccgccg acgccggcac ctactactgc atcaaattca gaaagggctc tcccgacacc     360
gaattcaaaa gcggcgccgg caccgaactg tccgtgcgag ctaagccctc cgagcccaaa     420
tcctcagaca gacccacac ctgtcccct tgtcctgccc ctgaactgct gggcggacct       480
tccgtgttcc tgttcccccc aaagcccaag gacaccctga tgatctcccg gacccccgaa     540
gtgacctgcg tggtggtgga tgtgtcccac gaggaccctg aagtgaagtt caattggtac     600
gtggacggcg tggaagtgca caacgccaag accaagccta gagaggaaca gtacaactcc     660
acctaccggg tggtgtccgt gctgaccgtg ctgcaccagg attggctgaa cggcaaagag     720
```

| | | |
|---|---|---|
| tacaagtgca aggtgtccaa caaggccctg cctgccccca tcgaaaagac catctccaag | 780 | |
| gccaagggcc agccccggga accccaggtg tacacactgc ccctagcag ggacgagctg | 840 | |
| accaagaacc aggtgtccct gtggtgtctc gtgaaaggct ctacccctc cgacattgcc | 900 | |
| gtggaatggg agtccaacgg ccagcctgag aacaactaca agaccacccc ccctgtgctg | 960 | |
| gactccgacg gctcattctt cctgtacagc aagctgacag tggacaagtc ccggtggcag | 1020 | |
| cagggcaacg tgttctcctg ctccgtgatg cacgaggccc tgcacaacca ctacacccag | 1080 | |
| aagtccctgt ccctgagccc cggcaaatga | 1110 | |

<210> SEQ ID NO 44
<211> LENGTH: 462
<212> TYPE: PRT
<213> ORGANISM: Artificial Sequence
<220> FEATURE:
<223> OTHER INFORMATION: D1m-D2-Fc2 amino acid sequence

<400> SEQUENCE: 44

```
Met Glu Trp Ser Trp Val Phe Leu Phe Leu Ser Val Thr Thr Gly
1               5                   10                  15

Val His Ser Glu Glu Leu Gln Ile Ile Gln Pro Asp Lys Ser Val
            20                  25                  30

Ser Val Ala Ala Gly Glu Ser Ala Ile Leu His Cys Thr Ile Thr Ser
        35                  40                  45

Leu Phe Pro Val Gly Pro Ile Gln Trp Phe Arg Gly Ala Gly Pro Ala
    50                  55                  60

Arg Val Leu Ile Tyr Asn Gln Arg Gln Gly Pro Phe Pro Arg Val Thr
65                  70                  75                  80

Thr Val Ser Glu Thr Thr Lys Arg Glu Asn Met Asp Phe Ser Ile Ser
                85                  90                  95

Ile Ser Asn Ile Thr Pro Ala Asp Ala Gly Thr Tyr Tyr Cys Ile Lys
            100                 105                 110

Phe Arg Lys Gly Ser Pro Asp Thr Glu Phe Lys Ser Gly Ala Gly Thr
        115                 120                 125

Glu Leu Ser Val Arg Ala Lys Pro Ser Glu Pro Lys Ser Ser Gly Pro
    130                 135                 140

Ala Ala Arg Ala Thr Pro Gln His Thr Val Ser Phe Thr Cys Glu Ser
145                 150                 155                 160

His Gly Phe Ser Pro Arg Asp Ile Thr Leu Lys Trp Phe Lys Asn Gly
                165                 170                 175

Asn Glu Leu Ser Asp Phe Gln Thr Asn Val Asp Pro Val Gly Glu Ser
            180                 185                 190

Val Ser Tyr Ser Ile His Ser Thr Ala Lys Val Val Leu Thr Arg Glu
        195                 200                 205

Asp Val His Ser Gln Val Ile Cys Glu Val Ala His Val Thr Leu Gln
    210                 215                 220

Gly Asp Pro Leu Arg Gly Thr Ala Asn Leu Ser Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
```

```
                    290                 295                 300
Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
                340                 345                 350

Lys Ala Lys Gly Gln Pro Arg Glu Pro Gln Val Tyr Thr Leu Pro Pro
            355                 360                 365

Ser Arg Asp Glu Leu Thr Lys Asn Gln Val Ser Leu Trp Cys Leu Val
        370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
450                 455                 460
```